US005227292A

United States Patent [19]

White et al.

[11] Patent Number: 5,227,292

[45] Date of Patent: Jul. 13, 1993

[54] NEUROFIBROMATOSIS TYPE 1 GENE

[75] Inventors: Raymond L. White, Salt Lake City; Peter O'Connell, Midvale; David H. Viskochil; Richard M. Cawthon, both of Salt Lake City, all of Utah

[73] Assignee: University of Utah, Salt Lake City, Utah

[21] Appl. No.: 551,531

[22] Filed: Jul. 12, 1990

[51] Int. Cl.$^5$ ........................ C12Q 1/68; C12P 21/06; C12N 15/00; C07H 15/12

[52] U.S. Cl. ................................ 435/69.1; 435/240.1; 435/252.3; 435/320.1; 436/23.5

[58] Field of Search ............... 435/6, 29, 320.1, 240.1, 435/252.3, 69.1; 536/27

[56] References Cited

PUBLICATIONS

Hadfield C. *Focus* 5(4):1-5 (1983).
O'Connell et al. *Am. J. Hum. Gen.* 44:51-57 (1989).
Fain et al. *Am. J. Hum. Gen.* 45:721-28 (1989).
Barker et al. *Science* 236:1100-02 (1987).
Cawthon et al. *Genomics.* 7:555-65 (1990).
O'Connell et al. *Genomics.* 7:547-554 (1990).
Cawthon et al. *Cell* 62:193-201 (1990).
Xu et al. *Cell* 62:599-608 (1990).
Wallace et al. *Science* 249:181-86 (1990).
Seizinger, B. R. et al. (1987). *Cell* 49:589-594.
Schmidt, M. A. et al. (1987). *Am. J. Med. Genet.* 28:771-777.
Fountain, J. W. et al. (1989). *Science* 244:1085-1087.
O'Connell, P. et al. (1989a). *Science* 224: 1087-1088.
Menon, A. G. et al. (1989). *Genomics* 5:245-249.
Collins, F. S. et al. (1989). *Am. J. Human Genet.* 44:1-5.
Golgar, D. E. et al. (1989). *Am. J. Human Genet.* 44:6-12.
Stephens, K. et al. (1989). *Am. J. Human Genet.* 44:13-19.
Ledbetter, D. H. et al. (1989). *Am. J. Human Genet.* 44:20-24.
Vance, J. M. et al. (1989). *Am. J. Human Genet.* 44:25-29.
Seizinger, B. R. et al. (1989). *Am. J. Human Genet.* 44:30-32.
Diehl, S. R. et al. (1989). *Am. J. Human Genet.* 44:33-37.
Mathew, C. G. P. et al. (1989). *Am. J. Human Genet.* 44:33-37.
Upadahyaya, M. et al. (1989). *Am. J. Human Genet.* 44:41-47.
Kittur, S. D. et al. (1989). *Am. J. Human Genet.* 44:48-50.
O'Connell, P. et al. (1989b). *Am. J. Human Genet.* 44:51-57.
Fain, P. R. et al. (1989). *Am. J. Human Genet.* 44:68-74.

*Primary Examiner*—Robert A. Wax
*Assistant Examiner*—Miguel Escallon
*Attorney, Agent, or Firm*—Venable, Baetjer, Howard & Civiletti

[57] ABSTRACT

The present invention relates to the neurofibromatosis type 1 (NF1) gene and its gene product. The invention further relates to methods for the detection in and treatment of humans having defective NF1 genes and for detection of tumors caused by a defective NF1 gene.

24 Claims, 16 Drawing Sheets

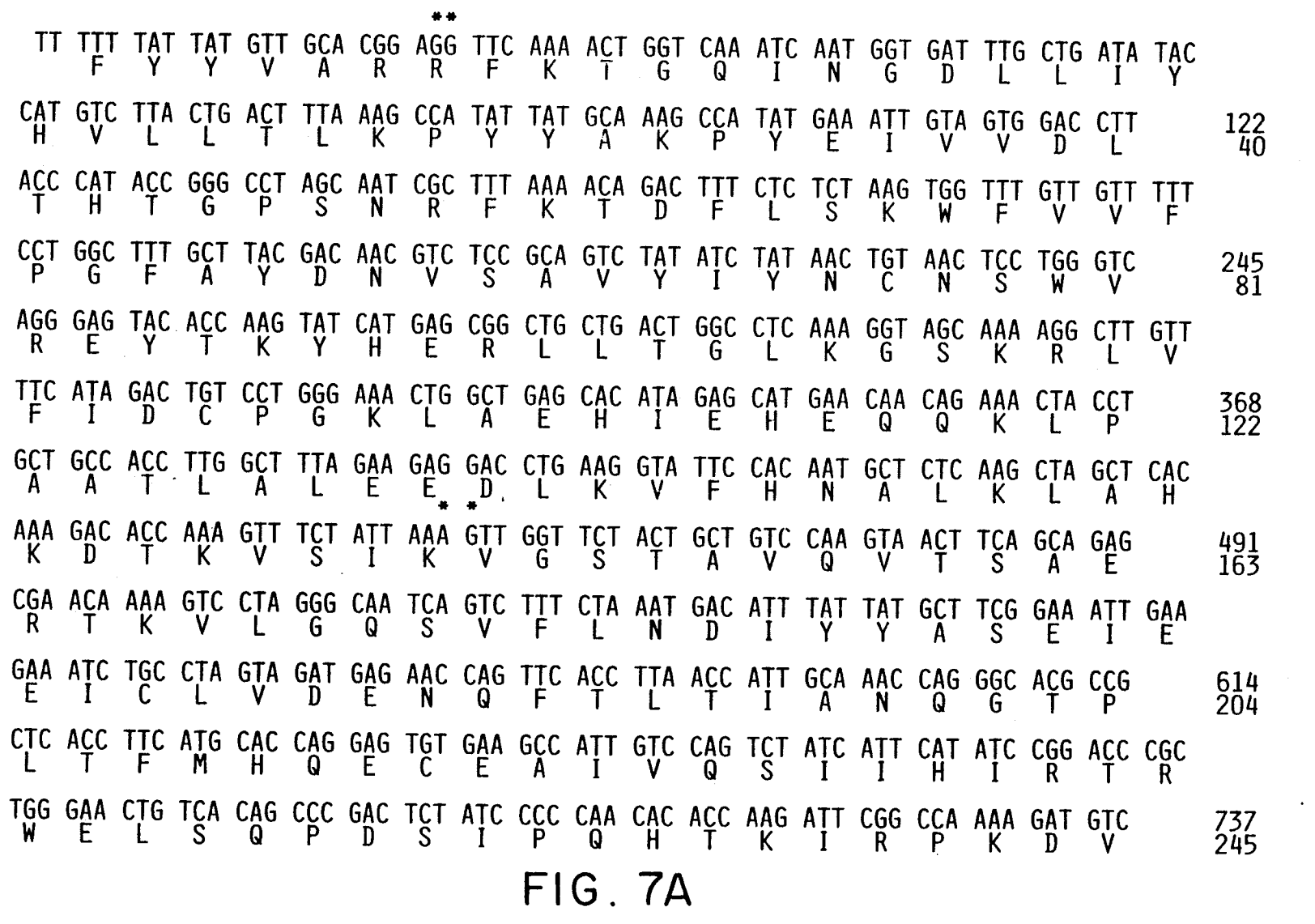

```
                               **
 TT TTT TAT TAT GTT GCA CGG AGG TTC AAA ACT GGT CAA ATC AAT GGT GAT TTG CTG ATA TAC
     F   Y   Y   V   A   R   R   F   K   T   G   Q   I   N   G   D   L   L   I   Y

CAT GTC TTA CTG ACT TTA AAG CCA TAT TAT GCA AAG CCA TAT GAA ATT GTA GTG GAC CTT      122
 H   V   L   L   T   L   K   P   Y   Y   A   K   P   Y   E   I   V   V   D   L        40

ACC CAT ACC GGG CCT AGC AAT CGC TTT AAA ACA GAC TTT CTC TCT AAG TGG TTT GTT GTT TTT
 T   H   T   G   P   S   N   R   F   K   T   D   F   L   S   K   W   F   V   V   F

CCT GGC TTT GCT TAC GAC AAC GTC TCC GCA GTC TAT ATC TAT AAC TGT AAC TCC TGG GTC      245
 P   G   F   A   Y   D   N   V   S   A   V   Y   I   Y   N   C   N   S   W   V        81

AGG GAG TAC ACC AAG TAT CAT GAG CGG CTG CTG ACT GGC CTC AAA GGT AGC AAA AGG CTT GTT
 R   E   Y   T   K   Y   H   E   R   L   L   T   G   L   K   G   S   K   R   L   V

TTC ATA GAC TGT CCT GGG AAA CTG GCT GAG CAC ATA GAG CAT GAA CAA CAG AAA CTA CCT      368
 F   I   D   C   P   G   K   L   A   E   H   I   E   H   E   Q   Q   K   L   P       122

GCT GCC ACC TTG GCT TTA GAA GAG GAC CTG AAG GTA TTC CAC AAT GCT CTC AAG CTA GCT CAC
 A   A   T   L   A   L   E   E   D   L   K   V   F   H   N   A   L   K   L   A   H
                             *   *
AAA GAC ACC AAA GTT TCT ATT AAA GTT GGT TCT ACT GCT GTC CAA GTA ACT TCA GCA GAG      491
 K   D   T   K   V   S   I   K   V   G   S   T   A   V   Q   V   T   S   A   E       163

CGA ACA AAA GTC CTA GGG CAA TCA GTC TTT CTA AAT GAC ATT TAT TAT GCT TCG GAA ATT GAA
 R   T   K   V   L   G   Q   S   V   F   L   N   D   I   Y   Y   A   S   E   I   E

GAA ATC TGC CTA GTA GAT GAG AAC CAG TTC ACC TTA ACC ATT GCA AAC CAG GGC ACG CCG      614
 E   I   C   L   V   D   E   N   Q   F   T   L   T   I   A   N   Q   G   T   P       204

CTC ACC TTC ATG CAC CAG GAG TGT GAA GCC ATT GTC CAG TCT ATC ATT CAT ATC CGG ACC CGC
 L   T   F   M   H   Q   E   C   E   A   I   V   Q   S   I   I   H   I   R   T   R

TGG GAA CTG TCA CAG CCC GAC TCT ATC CCC CAA CAC ACC AAG ATT CGG CCA AAA GAT GTC      737
 W   E   L   S   Q   P   D   S   I   P   Q   H   T   K   I   R   P   K   D   V       245
```

FIG. 7A

```
                                                                       **
CCT GGG ACA CTG CTC AAT ATC GCA TTA CTT AAT TTA GGC AGT TCT GAC CCG AGT TTA CGG TCA
 P   G   T   L   L   N   I   A   L   L   N   L   G   S   S   D   P   S   L   R   S

GCT GCC TAT AAT CTT CTG TGT GCC TTA ACT TGT ACC TTT AAT TTA AAA ATC GAG GGC CAG      860
 A   A   Y   N   L   L   C   A   L   T   C   T   F   N   L   K   I   E   G   Q       286

TTA CTA GAG ACA TCA GGT TTA TGT ATC CCT GCC AAC AAC ACC CTC TTT ATT GTC TCT ATT AGT
 L   L   E   T   S   G   L   C   I   P   A   N   N   T   L   F   I   V   S   I   S

AAG ACA CTG GCA GCC AAT GAG CCA CAC CTC ACG TTA GAA TTT TTG GAA GAG TGT ATT TCT      983
 K   T   L   A   A   N   E   P   H   L   T   L   E   F   L   E   E   C   I   S       327
                    **
GGA TTT AGC AAA TCT AGT ATT GAA TTG AAA CAC CTT TGT TTG GAA TAC ATG ACT CCA TGG CTG
 G   F   S   K   S   S   I   E   L   K   H   L   C   L   E   Y   M   T   P   W   L

TCA AAT CTA GTT CGT TTT TGC AAG CAT AAT GAT GAT GCC AAA CGA CAA AGA GTT ACT GCT     1106
 S   N   L   V   R   F   C   K   H   N   D   D   A   K   R   Q   R   V   T   A       368

ATT CTT GAC AAG CTG ATA ACA ATG ACC ATC AAT GAA AAA CAG ATG TAC CCA TCT ATT CAA GCA
 I   L   D   K   L   I   T   M   T   I   N   E   K   Q   M   Y   P   S   I   Q   A
                              *  *
AAA ATA TGG GGA AGC CTT GGG CAG ATT ACA GAT CTG CTT GAT GTT GTA CTA GAC AGT TTC     1229
 K   I   W   G   S   L   G   Q   I   T   D   L   L   D   V   V   L   D   S   F       409

ATC AAA ACC AGT GCA ACA GGT GGC TTG GGA TCA ATA AAA GCT GAG GTG ATG GCA GAT ACT GCT
 I   K   T   S   A   T   G   G   L   G   S   I   K   A   E   V   M   A   D   T   A
                                                  *  *
GTA GCT TTG GCT TCT GGA AAT GTG AAA TTG GTT TCA AGC AAG GTT ATT GGA AGG ATG TGC     1352
 V   A   L   A   S   G   N   V   K   L   V   S   S   K   V   I   G   R   M   C       450

AAA ATA ATT GAC AAG ACA TGC TTA TCT CCA ACT CCT ACT TTA GAA CAA CAT CTT ATG TGG GAT
 K   I   I   D   K   T   C   L   S   P   T   P   T   L   E   Q   H   L   M   W   D

GAT ATT GCT ATT TTA GCA CGC TAC ATG CTG ATG CTG TCC TTC AAC AAT TCC CTT GAT GTG     1475
 D   I   A   I   L   A   R   Y   M   L   M   L   S   F   N   N   S   L   D   V       491
```

FIG. 7B

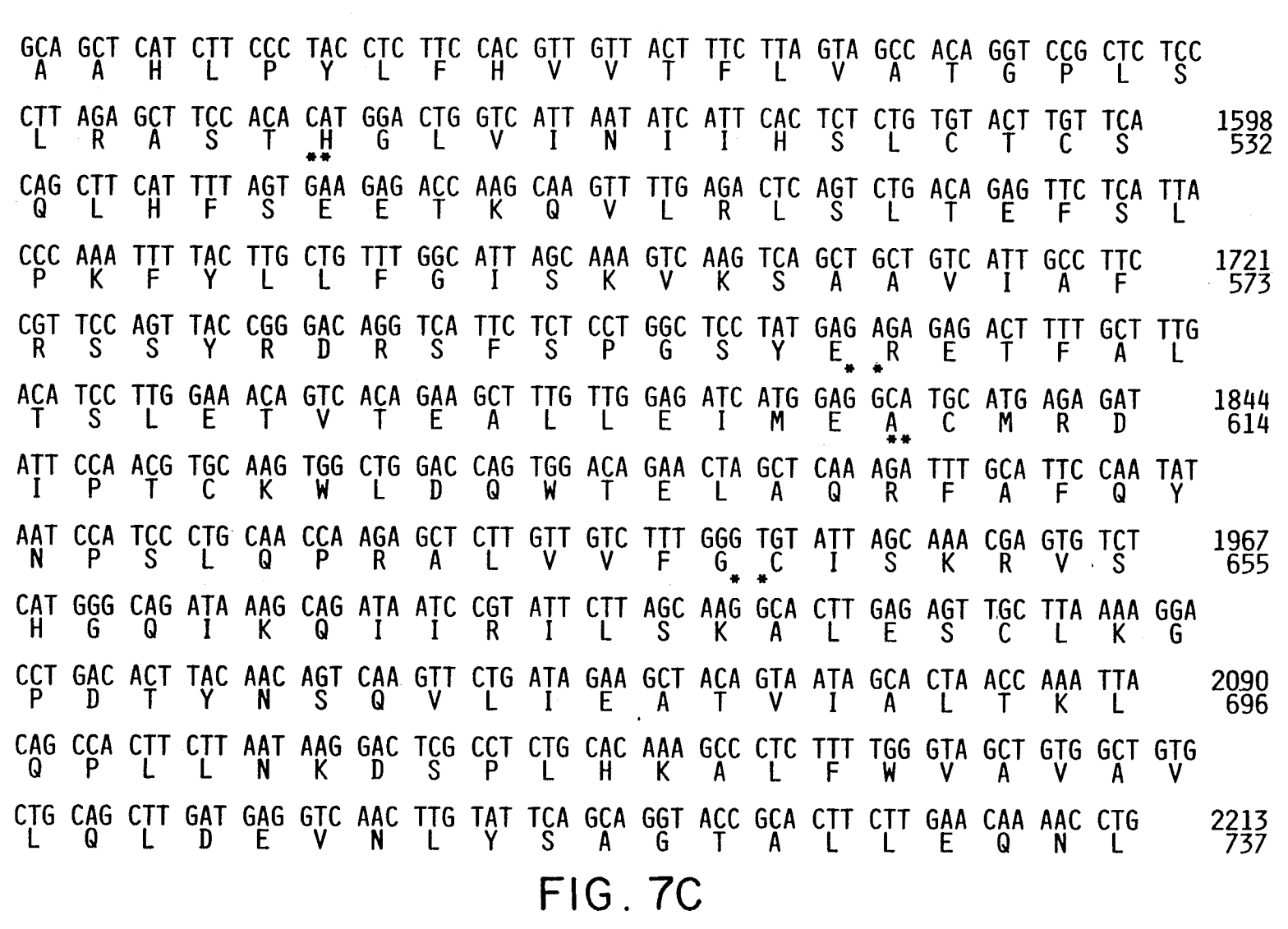

```
GCA GCT CAT CTT CCC TAC CTC TTC CAC GTT GTT ACT TTC TTA GTA GCC ACA GGT CCG CTC TCC
 A   A   H   L   P   Y   L   F   H   V   V   T   F   L   V   A   T   G   P   L   S

CTT AGA GCT TCC ACA CAT GGA CTG GTC ATT AAT ATC ATT CAC TCT CTG TGT ACT TGT TCA      1598
 L   R   A   S   T   H   G   L   V   I   N   I   I   H   S   L   C   T   C   S        532
                     **
CAG CTT CAT TTT AGT GAA GAG ACC AAG CAA GTT TTG AGA CTC AGT CTG ACA GAG TTC TCA TTA
 Q   L   H   F   S   E   E   T   K   Q   V   L   R   L   S   L   T   E   F   S   L

CCC AAA TTT TAC TTG CTG TTT GGC ATT AGC AAA GTC AAG TCA GCT GCT GTC ATT GCC TTC      1721
 P   K   F   Y   L   L   F   G   I   S   K   V   K   S   A   A   V   I   A   F        573

CGT TCC AGT TAC CGG GAC AGG TCA TTC TCT CCT GGC TCC TAT GAG AGA GAG ACT TTT GCT TTG
 R   S   S   Y   R   D   R   S   F   S   P   G   S   Y   E   R   E   T   F   A   L
                                                         *   *
ACA TCC TTG GAA ACA GTC ACA GAA GCT TTG TTG GAG ATC ATG GAG GCA TGC ATG AGA GAT      1844
 T   S   L   E   T   V   T   E   A   L   L   E   I   M   E   A   C   M   R   D        614
                                                             **
ATT CCA ACG TGC AAG TGG CTG GAC CAG TGG ACA GAA CTA GCT CAA AGA TTT GCA TTC CAA TAT
 I   P   T   C   K   W   L   D   Q   W   T   E   L   A   Q   R   F   A   F   Q   Y

AAT CCA TCC CTG CAA CCA AGA GCT CTT GTT GTC TTT GGG TGT ATT AGC AAA CGA GTG TCT      1967
 N   P   S   L   Q   P   R   A   L   V   V   F   G   C   I   S   K   R   V   S        655
                                                 *   *
CAT GGG CAG ATA AAG CAG ATA ATC CGT ATT CTT AGC AAG GCA CTT GAG AGT TGC TTA AAA GGA
 H   G   Q   I   K   Q   I   I   R   I   L   S   K   A   L   E   S   C   L   K   G

CCT GAC ACT TAC AAC AGT CAA GTT CTG ATA GAA GCT ACA GTA ATA GCA CTA ACC AAA TTA      2090
 P   D   T   Y   N   S   Q   V   L   I   E   A   T   V   I   A   L   T   K   L        696

CAG CCA CTT CTT AAT AAG GAC TCG CCT CTG CAC AAA GCC CTC TTT TGG GTA GCT GTG GCT GTG
 Q   P   L   L   N   K   D   S   P   L   H   K   A   L   F   W   V   A   V   A   V

CTG CAG CTT GAT GAG GTC AAC TTG TAT TCA GCA GGT ACC GCA CTT CTT GAA CAA AAC CTG      2213
 L   Q   L   D   E   V   N   L   Y   S   A   G   T   A   L   L   E   Q   N   L        737
```

FIG. 7C

```
CAT ACT TTA GAT AGT CTC CGT ATA TTC AAT GAC AAG AGT CCA GAG GAA GTA TTT ATG GCA ATC
 H   T   L   D   S   L   R   I   F   N   D   K   S   P   E   E   V   F   M   A   I

CGG AAT CCT CTG GAG TGG CAC TGC AAG CAA ATG GAT CAT TTT GTT GGA CTC AAT TTC AAC      2336
 R   N   P   L   E   W   H   C   K   Q   M   D   H   F   V   G   L   N   F   N        778

TCT AAC TTT AAC TTT GCA TTG GTT GGA CAC CTT TTA AAA GGG TAC AGG CAT CCT TCA CCT GCT
 S   N   F   N   F   A   L   V   G   H   L   L   K   G   Y   R   H   P   S   P   A

ATT GTT GCA AGA ACA GTC AGA ATT TTA CAT ACA CTA CTA ACT CTG GTT AAC AAA CAC AGA      2459
 I   V   A   R   T   V   R   I   L   H   T   L   L   T   L   V   N   K   H   R        819

AAT TGT GAC AAA TTT GAA GTG AAT ACA CAG AGC GTG GCC TAC TTA GCA GCT TTA CTT ACA GTG
 N   C   D   K   F   E   V   N   T   Q   S   V   A   Y   L   A   A   L   L   T   V

TCT GAA GAA GTT CGA AGT CGC TGC AGC CTA AAA CAT AGA AAG TCA CTT CTT CTT ACT GAT      2582
 S   E   E   V   R   S   R   C   S   L   K   H   R   K   S   L   L   L   T   D        860

ATT TCA ATG GAA AAT GTT CCT ATG GAT ACA TAT CCC ATT CAT CAT GGT GAC CCT TCC TAT AGG
 I   S   M   E   N   V   P   M   D   T   Y   P   I   H   H   G   D   P   S   Y   R

ACA CTA AAG GAG ACT CAG CCA TGG TCC TCT CCC AAA GGT TCT GAA GGA TAC CTT GCA GCC      2705
 T   L   K   E   T   Q   P   W   S   S   P   K   G   S   E   G   Y   L   A   A        901

ACC TAT CCA ACT GTC GGC CAG ACC AGT CCC CGA GCC AGG AAA TCC ATG AGC CTG GAC ATG GGG
 T   Y   P   T   V   G   Q   T   S   P   R   A   R   K   S   M   S   L   D   M   G

CAA CCT TCT CAG GCC AAC ACT AAG AAG TTG CTT GGA ACA AGG AAA AGT TTT GAT CAC TTG      2828
 Q   P   S   Q   A   N   T   K   K   L   L   G   T   R   K   S   F   D   H   L        942

ATA TCA GAC ACA AAG GCT CCT AAA AGG CAA GAA ATG GAA TCA GGG ATC ACA ACA CCC CCC AAA
 I   S   D   T   K   A   P   K   R   Q   E   M   E   S   G   I   T   T   P   P   K

ATG AGG AGA GTA GCA GAA ACT GAT TAT GAA ATG GAA ACT CAG AGG ATT TCC TCA TCA CAA      2951
 M   R   R   V   A   E   T   D   Y   E   M   E   T   Q   R   I   S   S   S   Q        983
```

FIG. 7D

```
CAG CAC CCA CAT TTA CGT AAA GTT TCA GTG TCT GAA TCA AAT GTT CTC TTG GAT GAA GAA GTA
 Q   H   P   H   L   R   K   V   S   V   S   E   S   N   V   L   L   D   E   E   V

CTT ACT GAT CCG AAG ATC CAG GCG CTG CTT CTT ACT GTT CTA GCT ACA CTG GTA AAA TAT      3074
 L   T   D   P   K   I   Q   A   L   L   L   T   V   L   A   T   L   V   K   Y       1024

ACC ACA GAT GAG TTT GAT CAA CGA ATT CTT TAT GAA TAC TTA GCA GAG GCC AGT GTT GTG TTT
 T   T   D   E   F   D   Q   R   I   L   Y   E   Y   L   A   E   A   S   V   V   F

CCC AAA GTC TTT CCT GTT GTG CAT AAT TTG TTG GAC TCT AAG ATC AAC ACC CTG TTA TCA      3197
 P   K   V   F   P   V   V   H   N   L   L   D   S   K   I   N   T   L   L   S       1065

TTG TGC CAA GAT CCA AAT TTG TTA AAT CCA ATC CAT GGA ATT GTG CAG AGT GTG GTG TAC CAT
 L   C   Q   D   P   N   L   L   N   P   I   H   G   I   V   Q   S   V   V   Y   H

GAA GAA TCC CCA CCA CAA TAC CAA ACA TCT TAC CTG CAA AGT TTT GGT TTT TAA TGGCTTG      3321
 E   E   S   P   P   Q   Y   Q   T   S   Y   L   Q   S   F   G   F                   1103

TGGCGGTTTGCAGGACCGTTTTCAAAGCAAACACAAATTCCAGACTATGCTGAGCTTATTGTTAAGTTTCTTGATGCCTTGATT

GACACGTACCTGCCTGGAATTGATGAAGAAACCAGTGAAGAATCCCTCCTGACTCCCACATCTCCTTACCCTCCTGCAC      3484

TGCAGAGCCAGCTTAGTATCACTGCCAACCTTAACCTTTCTAATTCCATGACCTCACTTGCAACTTCCCAGCATTCCCCAGGAA

TCGACAAGGAGAACGTTGAACTCTCCCCTACCACTGGCCACTGTAACAGTGGACGAACTCGCCACGGATCCGCAAGCCA      3647

AGTGCAGAAGCAAAGAAGCGCTGGCAGTTTCAAACGTAATAGCATTAAGAAGATCGTGTGAAGCTTGCTTGCTTTCTTTTTTAA

AATCAACTTAACATGGGCTCTTCACTAGTGACCCCTTCCCTGTCCTTGCCCTTTCCCCCCATGTTGTAATGCTGCACTT      3810

CCTGTTTTATAATGAACCCATCCGGTTTGCCATGTTGCCAGATGATCAACTCTTCGAAGCCTTGCCTAAATTTAATGCTGCCTT

TTCTTTAACTTTTTTTCTTCTACTTTTGGCGTGTATCTGGTATATGTAAGTGTTCAGAACAACTGCAAAGAAAGTGGGA      3973

GGTCAGGAAACTT                                                                          3986
```

FIG. 7E

5'- TTTATTTTAAACACTGCTAATAATCTTTGTCTTTTTGTCATTTCCTTAG [ exon1 433 nt. ]

TAAAGAGTTTAATTCTTCCACTTCACCCGTCACCACTTTCCAG [ exon2 341 nt. ]

TGGAACTTATAAGGATCGTTAAAACAACTTCATTTGTGTTTCTCCTAG [ exon3 203 nt. ]

TGATGTGATTTTCATTGACCACCATCACATGCTAATAGTGTATTTTTTCCAG [ exon4 193 nt. ]

AATTAAAATTGGTAGAGTGATTAAAACATGTTATTTCCTCTCAACTAG [ exon5 141 nt. ]

AGTCCCATGTTTTTTTAAAAAAAAAAAATCCGCTCTTTACAG [ exon6 282 nt. ]

AATTAAAAAAGTAATATTTCGTCTTTACTGTCCTTTATTCTCTTACAG [ exon7 216 nt. ]

TCTAAAAACATTTATGTACAATATGTATTCAGAGTATCCCCTTTTTTAG [ exon8 62 nt. ]

ATATATAAACACAAAGGTTTTTATAAGTTCTGTGGATCTTTTAATTGCAG [ exon9 120 nt. ]

FIG. 8B

| exon1 433 nt. | GTAAGTTCCAGTCTGTGTTTGTAAACGATTCATTGCTTTCTGACTAA -3' |
| exon2 341 nt. | GTAGGTTTTTAAAATTCTCTCAGTTGATTGGGGTTGTTGCTTTAA |
| exon3 203 nt. | GTAAGTAATGATAATTTCTTAATACTAACAATTATTCTAAGAGAATTC |
| exon4 193 nt. | GTATTGAGTTTGCTCAAATATTTATCTAGTATCTCCTTGTGCACATATT |
| exon5 141 nt. | GTAATCACTTTTCTTTGCCTTCTGTACTATAGCATATCTGTTTTATCAT |
| exon6 282 nt. | GTAAGTTCTAGGAAAGGAATTGTGTTTACCAGTTCCTTTCTCCATTTTA |
| exon7 216 nt. | GTATAGAAGCCAAAATGATAAGAAACTAAGTTAAAATCTTTTTAAAAA |
| exon8 62 nt. | GTATGTCCTAAATTAAAATATAAGTTGTAAAATATGCATATTGTTGAAAAT |
| exon9 120 nt. | GTACCTGTTCCGCCCTCACTTCTCCCAAATATTTATGGTTCTCAAGTTGT |

FIG. 8C

NEUROFIBROMATOSIS TYPE 1 GENE

BACKGROUND OF THE INVENTION

The present invention relates to the neurofibromatosis type 1 (NF1) gene and its gene product. The invention further relates to methods for the detection and treatment of humans having defective NF1 genes.

The publications and other materials used herein to illuminate the background of the invention and in particular cases to provide additional details respecting its practice are incorporated by reference and for convenience are numerically referenced in the following text and respectively grouped in the appended bibliography.

The neurofibromatoses are genetic disorders that primarily affect cell growth of neural tissues. These disorders can cause tumors to grow on the nerves at any location and at any time. Some manifestations are progressive, and may result in significant morbidity or mortality. Two distinctive forms are recognized, but variant forms may exist.

The most common type, neurofibromatosis type 1 or NF1 (previously known as von Recklinghausen's neurofibromatosis or peripheral neurofibromatosis), is an autosomal dominant disorder affecting about 1 in 3500 individuals (1).

The spontaneous mutation rate is quite high, with 30%-50% of NF1 affected individuals representing new mutations. This leads to a calculated mutation rate of about 1/10,000, which is about 100-fold higher than the usual mutation rate for a single locus. One explanation for such a high mutation rate is that the NF1 gene is a megagene analogous to the Duchenne muscular dystrophy gene.

The clinical features of the disorder are startlingly variable, even within the same family, indicating that other events must play a role in the eventual phenotype of the disease. The diagnostic criteria for NF1 include the presence of two or more of the following: (1) six or more cafê-au-lait macules more than 15 mm in greatest diameter in postpubertal individuals, or 5 mm in prepubertal individuals; (2) two or more neurofibromas of any type, or one plexiform neurofibroma; (3) freckling in the axillary or inguinal regions; (4) optic glioma; (5) two or more Lisch nodules (iris hamartomas); (6) a distinctive bony lesion such as sphenoid dysplasia or thinning of long-bone cortex, with or without pseudoarthrosis; (7) a first-degree relative with NF1 (1). The penetrance of NF1 is extremely high if individuals are carefully examined, including the use of a slit-lamp to detect Lisch nodules. Under those circumstances, it is rare to identify an adult obligate gene carrier who does not meet the criteria listed above (2).

Mapping of the NF1 gene to human chromosome 17q has involved the use of linkage analysis on NF1 families (3-5) and physical mapping using somatic cell hybrids and pulsed-field gel electrophoresis (PFGE) (6-8). Two NF1 translocation have been identified within 17q11.2, t(1;17) and t(17;22) (9,7). The portion of chromosome 17 containing these translocations has sometimes been referred to as the translation breakpoint region (TBR). Although significant progress has been made in mapping the NF1 gene, the gene has not been identified, cloned or sequenced prior to the present invention.

SUMMARY OF THE INVENTION

The present invention is directed to an isolated DNA sequence encoding the NF1 gene or fragments thereof. The NF1 gene or fragments may be a synthetic gene, e.g., cDNA, or genomic DNA. The invention is also directed to vectors containing the DNA sequence or fragments thereof and to cells transformed by the DNA sequence or fragments thereof. The invention is further directed to polypeptides encoded by the NF1 gene or fragments thereof, antibodies (monoclonal or polyclonal) to these polypeptides or to naturally occurring NF1 polypeptide. NF1 polypeptide is the polypeptide encoded by the native NF1 gene or the isolated DNA sequence described herein. The invention is also directed to a composition, suitable for treating a human having a defective NF1 gene, containing NF1 polypeptide or a fragment thereof, in a pharmacologically acceptable carrier.

In addition, the present invention is directed to methods of screening humans to determine those at risk of developing neurofibromatosis type 1 by a DNA diagnostic test in which the nucleic acid of the human is analyzed. An immunological diagnostic test in which a tumor is analyzed to identify those tumors caused by a defect in the NF1 gene.

Finally, the invention is directed to a method of treating a human with NF1 polypeptide.

BRIEF DESCRIPTION OF THE DRAWINGS

FIGS. 7(A-E) is a nucleic acid sequence with corresponding amino acid sequence of a cDNA sequence of a normal (i.e., non-defective) NF1 gene. The 3986 nucleotides of DNA sequence generated from the overlapping st of cDNA clones defining the TBR (NF1) gene is shown with translation of the 1103 amino acid open reading frame. The known exon splice junctions for exons 1 through 9 are indicated by double dots at the exon boundaries. Nucleotides 1-780 are from cDNA FB37, 942-1190 from FB9, 1120-1890 from FB20, 1190-1610 from FB16, 1792-1968 from FB6, 1886-3238 from FB18, 1969-3373 from FB4, 2877-3020 from FB9, 2886-3163 from FB35, 3020-3310 from FB38, 2554-3986 from FB13, and 1930-3986 from FB8. A gap in contiguous sequence between nucleotides 824 and 942 is spanned by genomic sequence from cEVI20. FB13 contains an additional 54 nucleotide. sequence (AGCTTCTCTGCCTTGCT-CTAACTCAG-CAGTTTTCATGCAGCTGTTCCCTCATCA) inserted at nucleotide 3563 of the sequence.

DETAILED DESCRIPTION OF THE INVENTION

Figure 1:
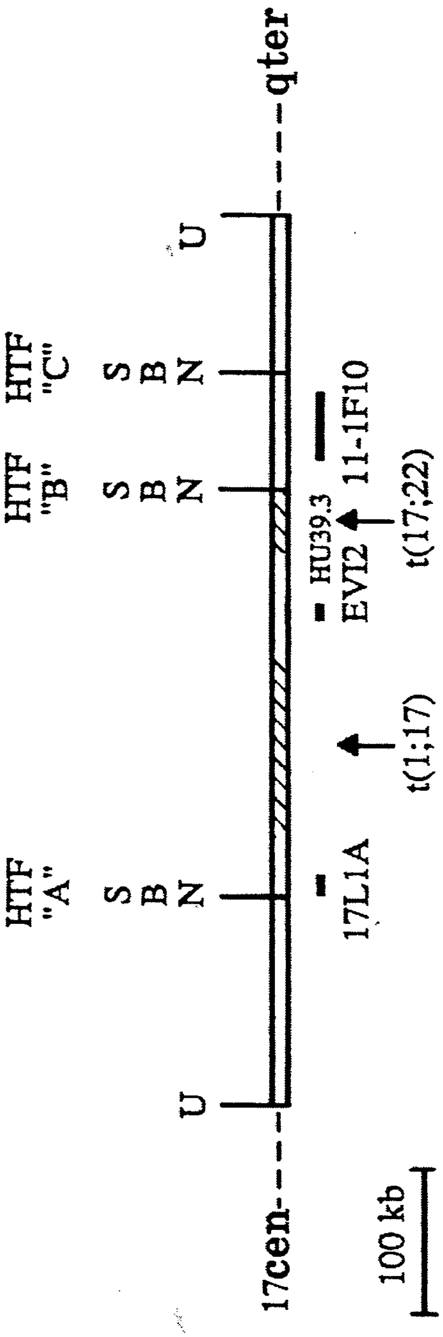
FIG. 1 is a diagrammatic representation of the PFGE map for the 600 kb NruI fragment that encompasses the NF1 translocation breakpoints. Cleavage sites: B=BssHII; N=NotI; S=SacII; U=NruI. Cross-hatching indicates where the translocation breakpoints are localized. The HTF "B" island may contain more than one set of CpG enzyme sites.

The present invention is directed to an isolated DNA sequence encoding the NF1 gene or DNA fragments thereof, polypeptides encoded by this DNA, antibodies to the polypeptides and compositions for treating humans having NF1. The invention is further directed to methods of screening humans for defective NF1 genes, diagnosing tumors to identify those tumors caused by a defective NF1 gene and treating a human having NF1.

Neurofibromatosis Type 1 Polypeptide

The NF1 polypeptide is the specific amino acid chain encoded by the nucleic acid sequence of the normal NF1 gene. The NF1 polypeptide of this invention includes: (1) naturally occurring NF1 protein; (2) synthetically produced NF1 polypeptide; and (3) NF1 polypeptide produced from purified nucleic acid (e.g., cDNA or genomic DNA) via an in vitro expression system. Also included are biologically active fragments of NF1 polypeptide or epitopes of these polypeptides. In addition, biologically active polypeptides or fragments thereof of transcripts within the NF1 gene such as EVI2, RC1 and the like, or include an epitope of these polypeptides and thus are suitable for production of specific antibodies. EVI2 and RC1 are located within the large introns of the NF1 gene.

As is the case for all proteins, the precise chemical structure depends on a number of factors. As ionizable amino and carboxyl groups are present in the molecule, a particular protein may be obtained as an acidic or basic salt, or in neutral form. All such preparations which retain their activity when placed in suitable environmental conditions are included in the definition. Further, the primary amino acid sequence may be augmented by derivatization using sugar moieties (glycosylation) or by other supplementary molecules such as lipids, phosphate, acetyl groups and the like, more commonly by conjugation with saccharides. The primary amino acid structure may also aggregate to form complexes, most frequently dimers. Certain aspects of such augmentation are accomplished through post-translational processing systems of the producing host; other such modifications may be introduced in vitro. In any event, such modifications are included in the definition so long as the activity of the protein, as defined above, is not destroyed. It is expected, of course, that such modifications may quantitatively or qualitatively affect the activity, either by enhancing or diminishing the activity of the protein in the various assays.

Further, individual amino acid residues in the chain may be modified by oxidation, reduction, or other derivatization., and the protein may be cleaved to obtain fragments which retain activity. Such alterations which do not destroy activity do not remove the protein sequence from the definition.

Modifications to the primary structure itself by deletion, addition, or alteration of the amino acids incorporated into the sequence during translation can be made without destroying the activity of the protein. Such substitutions or other alterations result in proteins having an amino acid sequence which falls within the definition of proteins "having an amino acid sequence substantially equivalent to that of NF1"

Neurofibromatosis Type 1 Gene

The NF1 gene is that distinct nucleic acid sequence in the human genome, the absence or mutation of which predisposes one to neurofibromatosis type 1. The NF1 gene as it exists in the human genome is a megagene having a size greater than 100 Kb and comprising many exons and introns spread out over the gene. The NF1 gene produces a transcript of approximately 11 Kb which codes for the NF1 polypeptide and which is spliced from more than 9 exons. Some of the introns have been found to contain open reading frames often found in the opposite orientation as the NF1 coding sequence. Fragments of the NF1 gene are intended to include any DNA sequence comprising 15 or more bases which are unique to the NF1 gene. The purified nucleic acid sequence containing or encoding the NF1 gene can be carried on vectors which can be propagated in cells. For the purposes of this invention, isolated nucleic acid encoding the NF1 gene is defined as nucleic acid isolated from its natural environment (e.g. cDNA or a fragment of genomic DNA) which hybridizes specifically to the NF1 gene under hybridizing conditions. This definition includes DNA which binds to the specific coding regions (exons) of the NF1 gene as well as DNA which binds to the non-coding regions (introns) of the gene. In addition to the NF1 gene, several open reading frames are present which code for other polypeptides. These open reading frames include EV12, RC1 and others described further below. In connection with the cloning of the NF1 gene, the following definitions are provided.

"Operably linked" refers to juxtaposition such that the normal function of the components can be performed. Thus, a coding sequence "operably linked" to control sequences refers to a configuration wherein the coding sequence can be expressed under the control of these sequences.

"Control sequences" refers to DNA sequences necessary for the expression of an operably linked coding sequence in a particular host organism. The control sequences which are suitable for procaryotes, for example, include a promoter, optionally an operator sequence, a ribosome binding site, and possibly, other as yet poorly understood, sequences. Eucaryotic cells are known to utilize promoters, polyadenylation signals, and enhancers.

"Expression system" refers to DNA sequences containing a desired coding sequence and control sequences in operable linkage, so that hosts transformed with these sequences are capable of producing the encoded proteins. In order to effect transformation, the expression system may be included on a vector; however, the relevant DNA may then also be integrated into the host chromosome.

As used herein "cell", "cell line", and "cell culture" are used interchangeably and all such designations include progeny. Thus "transformants" or "transformed cells" includes the primary subject cell and cultures derived therefrom without regard for the number of transfers. It is also understood that all progeny may not be precisely identical in DNA content, due to deliberate or inadvertent mutations. Mutant progeny which have the same functionality as screened for in the originally transformed cell, are included. Where distinct designations are intended, it will be clear from the context.

In general terms, the production of a recombinant form of NF1 typically involves the following:

First a DNA encoding the mature (used here to include all muteins) protein, the preprotein, or a fusion of the NF1 protein to an additional sequence cleavable under controlled conditions (such as treatment with peptidase to give an active protein, is obtained. If the sequence is uninterrupted by introns it is suitable for expression in any host. If there are introns, expression is obtainable in mammalian or other eucaryotic systems capable of processing them. This sequence should be in excisable and recoverable form. The excised or recovered coding sequence is then placed in operable linkage with suitable control sequences in a replicable expression vector. The vector is used to transform a suitable host and the transformed host culture under favorable conditions to effect the production of the recombinant NF1. Optionally the NF1 is isolated from the medium or from the cells and purified.

Each of the foregoing steps can be done in a variety of ways. For example, the desired coding sequences can be obtained by preparing suitable cDNA from cellular messenger and manipulating the cDNA to obtain the complete sequence. Alternatively, genomic fragments may be obtained and used directly in appropriate hosts. The constructions for expression vectors operable in a variety of hosts are made using appropriate replicons and control sequences, as set forth below. Suitable restriction sites can if not normally available, be added to the ends of the coding sequence so as to provide an excisable gene to insert into these vectors.

The control sequences, expression vectors, and transformation methods are dependent on the type of host cell used to express the gene. Generally, procaryotic, yeast, or mammalian cells are presently useful as hosts. Procaryotic hosts are in general the most efficient and convenient for the production of recombinant proteins. However, eucaryotic cells, and, in particular, mammalian cells are sometimes used for their processing capacity.

Procaryots most frequently are represented by various strains of *E. coli.* However, other microbial strains may also be used, such as bacilli, for example *Bacillus subtilis*, various species of Pseudomonas, or other bacterial strains. In such procaryotic systems, plasmid or bacteriophage vectors which contain replication sites and control sequences derived from a species compatible with the host are used. A wide variety of vectors for many procaryotes are known (12-14, 49). Commonly used procaryotic control sequences which are defined herein to include promoters for transcription initiation, optionally with an operator, along with ribosome binding site sequences, include such commonly used promoters as the beta-lactamas (penicillinase) and lactose (lac) promoter systems, the tryptophan (trp) promoter system and the lambda derived PL promoter and N-gene ribosome binding site, which has been made useful as a portable control cassette (50). However, any available promoter system compatible with procaryotes can be used (12–14,49).

In addition to bacteria, eucaryotic microbes, such yeast, may also be used as hosts. Laboratory strains of *Saccharomyces cerevisiae,* Baker's yeast, are most used although a number of other strains are commonly available. Vectors employing the 2 micron origin of replication and, other plasmid vectors suitable for yeast expression are known (12–14, 49). Control sequences for yeast vectors include promoters for the synthesis of glycolytic enzymes. Additional promoters known in the art include the promoter for 3-phosphoglycerate kinase, and those for other glycolytic enzymes, such as glyceraldehyde-3-phosphate dehydrogenase, hexokinase, pyruvate decarboxylase, phosphofructokinase , glucose-6-phosphate isomerase, 3-phosphoglycerate mutase, pyruvate kinase, triosephosphate isomerase, 3-phosphoglycerate mutase, pyruvate kinase, triosephosphate isomerase, phosphoglucose isomerase, and glucokinase. Other promoters, which have the additional advantage of transcription controlled by growth conditions, are the promoter regions for alcohol dehydrogenase 2, isocytochrome C, acid phosphatase, degradative enzymes associated with nitrogen metabolism, and enzymes responsible for maltose and galactose utilization. (See 12–14, 49.) It is also believed terminator sequences are desirable at the 3′ end of the coding sequences. Such terminators are found in the 3′ untranslated region following the coding sequences in yeast-derived genes. Many of the vectors illustrated contain control sequences derived from the enolase gene containing plasmid peno46 or the LEU2 gene obtained from YEp13, however, any vector containing a yeast compatible promoter, origin of replication and other control sequences is suitable (12–14, 49).

It is also, of course, possible to express genes encoding polypeptides in eucaryotic host cell cultures derived from multicellular organisms (51–53). Useful host cell lines include murine myelomas N51, VERO and HeT cells, and Chinese hamster ovary (CHO) cells. Expression vectors for such cells ordinarily include promoters and control sequences compatible with mammalian cells such as, for example, the commonly used early and later promoters from Simian Virus 40 (SV 40), or other viral promoters such as those derived from polyoma, Adenovirus 2, bovine papilloma virus, or avian sarcoma viruses, or immunoglobulin promoters and heat shock promoters (12–14, 49). General aspects of mammalian cell host system transformations have been described by Axel. (54) It now appears also that "enhancer" regions are important in optimizing expression; these are, generally, sequences found upstream of the promoter region. Origins of replication may be obtained, if needed, from viral sources. However, integration into the chromosome is a common mechanism for DNA replication in eucaryotes. Plant cells are also now available as hosts, and control sequences compatible with plant cells such as the nopaline synthase promoter and polyadenylation signal sequences are available (49, 55, 56).

Depending on the host cell used, transformation is done using standard techniques appropriate to such cells (12–14, 54–56). Such techniques include, but is not limited to, calcium treatment employing calcium chloride for procaryotes or other cells which contain substantial cell wall barriers; infection with *Agrobacterium tumefaciens* for certain plant cells; calcium phosphate precipitation method for mammalian cells without cell walls; and, microprojectile bombardment for many cells including plant cells.

The identification of the native NF1 gene and sequencing involved conventional gene mapping and recombinant techniques including the use of linkage analysis, somatic cell hybrids, cosmid-walking, genomic and cDNA libraries, DNA sequencing and PCR. Genomic libraries are prepared from Sau3A partial digests of genomic DNA and cloned into bacteriophage or cosmid vectors after fractionation. cDNA libraries can be purchased commercially. For example, a normal adult made peripheral blood leukocyte oligo(dT)-primed cDNA library in λgt10 (catalogene number HL1062A, Clonetech Laboratories, Inc.) and a human fetal brain oligo(dT)- and random-primed cDNA in ZapII (catalogene number 936206, Stratagene) among others are available.

It was discovered that the two NF1 translocations (7,9) occurred within a 600 Kb NruI restriction fragment (10). By analysis of somatic cell hybrids containing the derivative chromosomes, a murine oncogene, Evi-2, was located between the translocation breakpoints, suggesting a role for the human homologue, EVI2, in NF1. However, analysis of the DNA sequence of the human gene from a number of unrelated NF1 patients revealed no NF1-specific mutations.

Figure 3A:
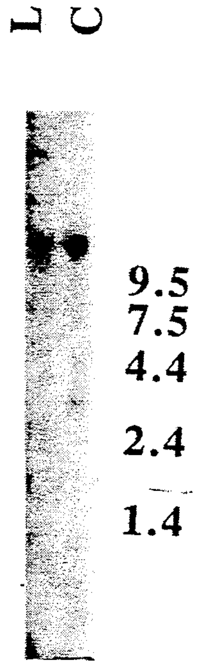
FIG. 3 show the characterization of TBR (NF1) cDNA clones. A Northern blot hybridization of TBR cDNA. cDNA FB4 and FB18 were radiolabelled and hybridized to a Northern blot of 5 μg total RNA from an EBV-transformed lymphoblastiod cell line (L) or choriocarcinoma cell line (C). Molecular weight standards are indicated in kilobases. B. Mapping of TBR cDNA FB17 to NF1 region cosmids. The autoradiographs show that FB17 spans the region from the proximal 9 kb EcoRI fragment in cEVI20 to the 14 kb EcoRI fragment in cT311. The unidentified cross-hybridizing EcoRI fragments represent the termini of the cosmid clones. C. Mapping of TBR cDNA FB8 to NF1 region cosmids. The autoradiographs show that FB8 (distal end of meld) identifies an EcoRI fragment in both cT316 and c7D5, and identifies two EcoRI fragments unique to c7D5, the most distal NF1 region cosmid. The exact positions of these EcoRI fragments are not known. D. The NF1 region cosmids are shown with an EcoRI restriction enzyme map of the NF1 region. Cross-hatching shows EcoRI fragment that cross-hybridize with TBR cDNAs. Stippling represents the positions of the translocation breakpoints.

To scan the region for additional genes, cosmids from the region were identified. A contiguous 130 kb genomic map of overlapping clones including cEVI20, cEVI36, cEVI37, cT311, cT315, cT316 and c7D5 (FIG. 3D) has been constructed and it encompasses both translocation breakpoints. By screening cDNA libraries with these cosmids, two additional genes were identified, RC1 and HB36, which were likewise found to lie between the two NF1 translocation breakpoints. A fourth locus, HB15, maps distal to both breakpoints. The predicted peptide derived from DNA sequence analysis indicate that both RC1 and VI2 are transmembrane proteins without specified function. HB15 is a pseudogene of the adenylate kinase 3 multigene family. HB36 matches the sequence of the oligodendrocyte-myelin glycoprotein (OMGP), a central nervous system cell surface peptide with properties of a cell adhesion molecule. Similar to EVI2, examination of the open reading frames of the RC1 and OMGP genes for point mutations revealed no NF1 mutations.

Additional NF1 patients were surveyed for new mutations that might either implicate one of these loci, or identify some other locus, as the NF1 gene. This screen has revealed three new NF1 deletions spanning 40 kb, 190 kb and 11 kb respectively. The 11 kb deletion does not remove sequences from any of the previously characterized genes, but it does delete part of a region conserved between mouse and human. A probe from the conserved region identified a clone from a murine macrophage cDNA library with which a number of human cDNA clones were identified. These clones define a new gene at the NF1 t(17;22) translocation breakpoint region (TBR), the NF1 gene. The terms TBR and NF1 gene will be used interchangeably herein and are to be understood to refer to the same locus.

The analysis of human fetal brain libraries resulted in the isolation of thirty cDNA clones reflecting sequences from the RNA transcript of the TBR gene. FIG. 7 shows the cDNA sequence obtained from the overlapping fetal brain clones FB4, FB6, FB8, FB9, FB13, FB16, FB18, FB20, FB35, FB37 and FB38. With one exception, DNA sequencing of overlapping fetal brain cDNAs has provided the continuous transcript sequence shown in FIG. 7. The exception is in one region of exon 3 where 118 bp of genomic sequence (see further below) is used to join two cDNA sequences. No intron-exon boundaries are seen within the 118 bp of genomic sequence. There are no stop codons in the open reading frame of the sequence from position 3 to position 3309. It should be noted that a second open reading frame, phase shifted; by one base, starts approximately 100 bp upstream from this stop codon and continues for approximately 600 bp past the stop codon. In addition, in one of the cDNA clones there is a 54 bp insertion between positions 3563 and 3564, downstream of the stop codon but suggesting inclusion of an additional exon through an alternate splicing of the message. None of the cDNA clones sequenced have a poly(A) tract at the cloning site and no two clones end with identical sequences. The 4 kb cDNA meld is likely internal to the transcript that may be as large as 11 kb. The sequence of the NP1 coding region is shown in Table 2 below.

The predicted amino acid sequence of the large open reading frame found in the TBR cDNA is used to search for homology to known DNA and protein sequence. No significant homologies have been detected thus far.

Use

The cDNA and genomic sequences, are used, according to the invention, to screen individuals for the presence of a mutated allele of the NF1 gene, and to detect defective NF1 genes in tumors, and the NF1 polypeptide is used therapeutically. The screening procedure will allow the identification of individuals having neurofibromatosis type 1. There is no limit on the type of tissue which may be analyzed. For example, the tissue can be tumor, blood, fibroblasts, skin or other normal tissue, and can be taken from fetal to adult tissue.

Screening

The screening procedure according to the invention includes: (1) testing a nucleic acid sample of a patient for large deletions in the NF1 gene locus and (2) testing a nucleic acid sample of a patient for small deletions or point mutations in the NF1 gene locus.

1. Detection of Large Deletions in the NF1 Gene

The availability of DNA probes from the NF1 gene provides a means of directly detecting genetic lesions that create neurofibromatosis type 1 alleles. Suitable probes include the entire normal (native) NF1 gene sequence, or fragments thereof consisting of 15 or more bases encoding a specific portion of the NF1 gene. The probes may be based on the NF1 coding sequence or on the genomic sequence, i.e., the sequence containing coding and non-coding sequence. When performed by Southern blot and dot blot procedures, this analysis is generally limited to the study of those lesions that create gross structural changes in the NF1 gene, such as deletion of many hundreds of base pairs.

The DNA for a Southern Blot or dot blot analysis is isolated from peripheral leucocytes or other suitable sample. To examine leucocyte DNA, a blood sample is obtained from the individual, and the genomic DNA is isolated from the leucocytes in the sample, according to standard techniques. This DNA is digested with a restriction endonuclease, and the resulting fragments are separated on an agarose electrophoresis gel according to a physical property such as molecular shape or molecular weight. For the purposes of this invention, molecular shape is defined as the structural configuration of the molecule (e.g., linear, circular, double-stranded or single-stranded). The DNA in the gel is transferred to a nitrocellulose filter by blotting. The filter is then probed with the appropriate cDNA or genomic sequences, such as those described herein. In order to more precisely define the location of any abnormalities detected, two or more subfragment probes can be used separately. The autoradiograms of the probed filter generate the data necessary to construct a restriction map of the NF1 locus in the somatic DNA of the tested individual.

This restriction map is compared with a control restriction map, determined by using the same restriction enzymes for digestion and the same probe. A suitable control is DNA obtained from an leucocyte DNA from a set of normal individuals. If the tested individual has an NF1 allele containing a significantly large deletion, a restriction map of his DNA, compared with the control, will contain an additional band or bands, and/or a band or bands that have lost 50% of their intensity, caused by a change in the size, or total elimination, of one or more restriction fragments by the deletion in one allele at the NF1 locus.

This screening procedure by Southern analysis will detect the existence of NF1 alleles which have large deletions. If this analysis indicates that the tested DNA from an individual has a restriction map which is different from the control map, there is a high probability that the individual contains a mutant NF1 allele.

If the test restriction map appears identical to the control, a different screening procedure can be performed to determine if the individual possesses an NF1 allele having a small deletion or point mutation. Small deletions and point mutations may be sufficient to render the allele defective, but not prevent hybridization with a probe. An example of this screening procedure is outlined below.

2. Detection of Other Mutations in the NF1 Gene

To examine a DNA sample of an individual for small deletions or point mutations in the NF1 locus, both homologs of the NF1 gene from said individual are cloned. The cloned alleles then can be tested for the presence of nucleic acid sequence differences from the normal allele by one of the following two methods: (1) the nucleotide sequence of both the cloned alleles and normal NF1 gene or appropriate fragment (coding sequence or genomic sequence) are determined and then compared, or (2) the RNA transcriptions of the NF1 gene or gene fragment are hybridized to single stranded whole genomic DNA from an individual to be tested, and the resulting heteroduplex is treated with Ribonuclease A (RNase A) and run on a denaturing gel to detect the location of any mismatches. In more detail, these methods can be carried out according to the following procedure.

The alleles of the NF1 gene in an individual to be tested are cloned using conventional techniques. (12–14) For example, a blood sample is obtained from the individual. The genomic DNA isolated from the cells in this sample is partially digested to an average fragment size of approximately 20 kb. Fragments in the range from 18–21 kb are isolated. The resulting fragments are ligated into an appropriate vector. The sequences of the clones are then determined and compared to the normal NF1 gene.

Figure 8A:
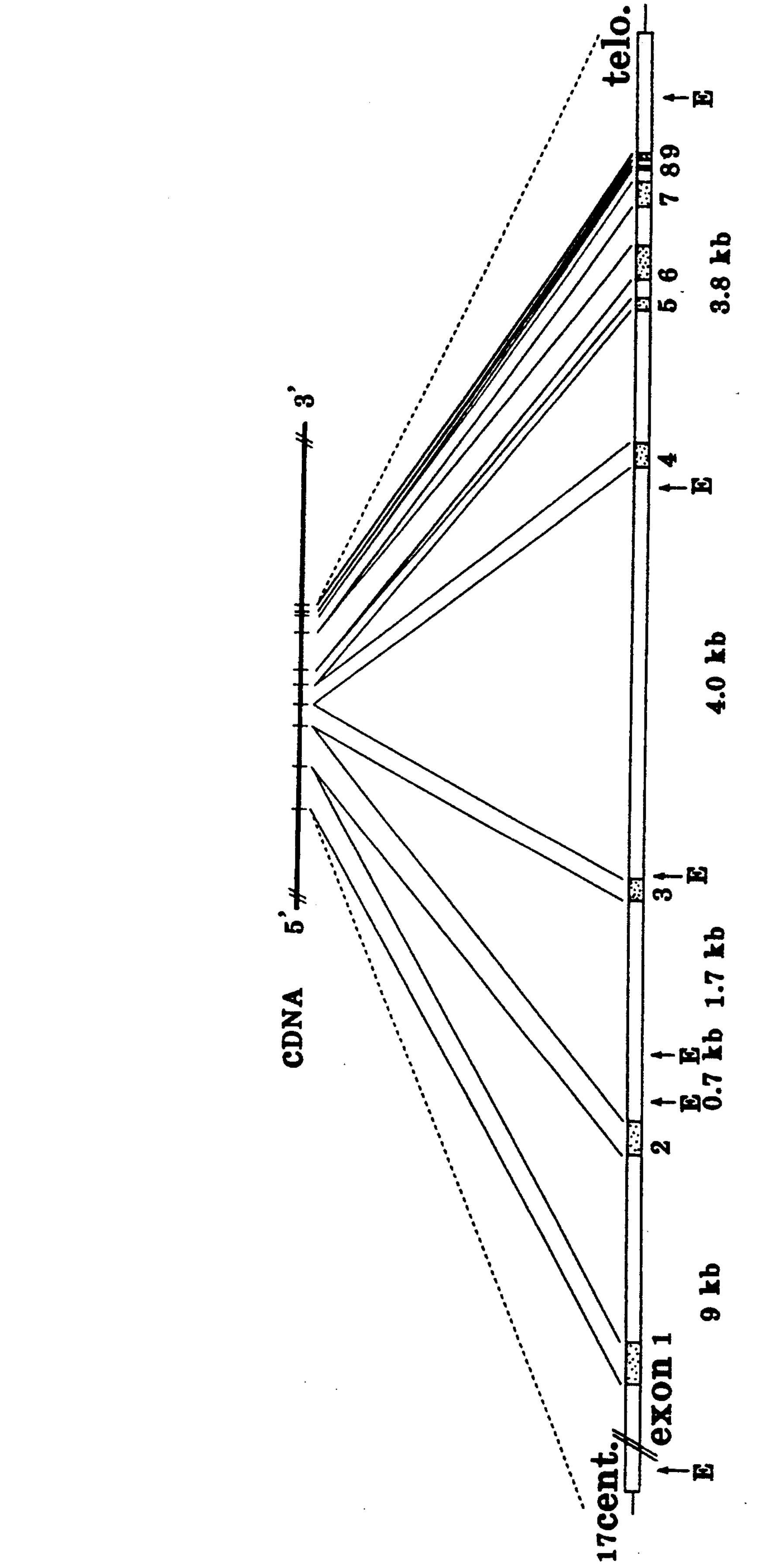
FIGS. 8(A-C) shows the intron-exon boundaries of TBR exons 1 to 9. 50 nucleotides of intronic sequence flanking each of the nine exons are shown in the centromeric to telomeric orientation. These sequences were derived from cEVI20 and the 3.8 kb EcoRI fragment from cT311. The length of each exon is shown, as well as their schematic location within the TBR composite cDNA and the EcoR1 contig mapped from cEVI20 and cT311. The actual sizes of the 9 and 3.8 kb EcoRI fragments are 8840 and 3889 nucleotides, respectively, by sequence determination.

Alternatively, PCRs are performed (59, 60) with primer pairs hat flank the NF1 Exons (sequences shown in FIG. 8). Example of such primer pairs are set forth in Table 1.

TABLE 1

Sequences of Primers Used for PCR-SSCP Analyses

| Primer Pair | Exon(s) Flanked | Sequence |
|---|---|---|
| A | 4 | 5'-ATAATTGTTGATGTGATTTTCATTG-3' |
| | | 5'-AATTTTGAACCAGATGAAGAG-3' |
| B | 5 | 5'-ATCTAGTATTTTTGAGGCCTCAG-3' |
| | | 5'-CAGATATGCTATAGTACAGAAGG-3' |
| C | 6 | 5'-CATATCTGTTTTATCATCAGGAGG-3' |
| | | 5'-AAGTAAAATGGAGAAAGGAACTGG-3' |
| D | 7 | 5'-CAAAATGAAACATGGAACTTTAGA-3' |
| | | 5'-TAAGCATTAAGTACAAATAGCACA-3' |
| E | 7, 8, 9 | 5'- TTTATGTTTGTGCTCTAACACCAAGT-3' |
| | | 5'-ATAAATGCTAGAATGATTTCTCATGCT-3' |

The first primer in each pair lies 5' of the exon or set of exons that it amplifies.

PCRs can also be performed with primer pairs based on any sequence of the normal NF1 gene. For example, primer pairs for the large intron can be prepared and utilized. Finally, PCR can also be performed on the mRNA. The amplified products are then analyzed by single stranded conformation polymorphisms (SSCP) (15,16) to identify any differences and these are then sequenced and compared to the normal NF1 gene sequence.

The second method employs RNase A to assist in the detection of differences between the normal NF1 gene and defective genes. This comparison is performed in steps using small (~500 bp) restriction fragments of the NF1 gene as the probe. First, the NF1 gene is digested with a restriction enzyme(s) that cuts the NF1 gene sequence into fragments of approximately 500 bp. These fragments are separated on an electrophoresis gel, purified from the gel and cloned individually, in both orientations, into an SP6 vector (e.g., pSP64 or pSP65; 57). The SP6-based plasmid containing inserts of the NF1 gene fragments are transcribed in vitro using the SP6 transcription system, well known in the art, in the presence of [$\alpha$-$^{32}$P]GTP, generating radiolabeled RNA transcripts of both strands of the NF1 gene.

Individually, these RNA transcripts are used to form heteroduplexes with the allelic DNA, as described by Myers et al., (58). Mismatches that occur in the RNA:DNA heteroduplex, owing to sequence differences between the NF1 fragment and the NF1 allele subclone from the individual, result in cleavage in the RNA strand when treated with RNase A. Such mismatches can be the result of point mutations or small deletions in the individual's NF1 allele. Cleavage of the RNA strand yields two or more small RNA fragments, which run faster on the denaturing gel than the RNA probe itself.

Any differences, small deletions or point mutations which are found, will identify an individual as either having a defective NF1 gene leading to neurofibromatosis (on the basis of prior known mutations) or being at risk of having a defective NF1 gene which could lead to neurofibromatosis.

Treatment of Patients Having a Defective NF1 Gene

In addition to screening, the invention includes polypeptide therapy for those individuals determined to contain a defective NF1 allele, and who therefore will develop neurofibromatosis type 1.

To prevent the formation of NF1 in these individuals, the NF1 polypeptide, or polypeptides of other transcripts described herein (in this description, references to NF1 polypeptide is intended to include any polypeptide of the transcripts of the NF1 gene locus), is administered therapeutically in an amount sufficient to inhibit NF1 clinical symptoms such as presence of cafê-au-lait macules, neurofibromatosis, freckling, etc. (termed herein as an anti-neurofibromatosis type 1-forming amount). An anti-NF1-forming dosage of the NF1 polypeptide is 1 to 500 μg/kilogram of body weight/day. The NF1 protein can be formulated in conventional ways standard in the art for the administration of protein substances. Administration by injection with a pharmacologically acceptable carrier, either alone or in combination with another agent, is preferred. Suitable formulations include solutions or suspensions, emulsions or solid compositions for reconstitution into injectables. Acceptable pharmacological carriers are those which dissolve the NF1 polypeptide or hold it in suspension, and which are not toxic to the extent of permanently harming the patient. Preferred are aqueous solutions of salts or non-ionic compounds such as sodium chloride, glycerol, glucose, or dextrose, most preferably at an isotonic concentration. Suitable examples are Ringer's solution and Hank's solution. Other agents may be present provided that they do not interfere with the action the NF1 polypeptide. Those skilled in the art will know, or will be able to ascertain with no more than routine experimentation, particular pharmacological carriers for this composition.

NF1 polypeptide suitable for therapy can be prepared by any one of the following three conventional procedures. First, the NF1 polypeptide can be produced by cloning the NF1 cDNA into an appropriate expression vector, expressing the NF1 gene product from this vector in an in vitro expression system, and isolating the NF1 polypeptide from the medium or cells of the expression system. General expression vectors and systems are well known in the art.

Second, the NF1 polypeptide can be produced using protein chemistry techniques, wherein the specific amino acid residues are joined together synthetically in the appropriate sequence.

Third, naturally occurring NF1 protein can be isolated from total protein samples by affinity chromatography. Antibodies specific for the NF1 protein are prepared by standard procedures and coupled to an inert matrix, which is then used to selectively bind the NF1 proteins.

Immunodiagnosis of NF1

This invention also includes methods for determining whether a particular clinical symptom such as noted above is the result of an NF1 gene abnormality. Immunodiagnosis can be used to aid in the diagnosis of patients at risk for NF1 or to determine whether a particular tumor is the result of a defective NF1 gene.

In order to produce anti-NF1 antibody, a rabbit is immunized with either naturally occurring NF1 protein or NF1 polypeptide produced as described above. Alternatively, a monoclonal anti-NF1 antibody is produced using conventional techniques (17, 17*a*). The anti-FI antibody generated is then labeled, e.g., radioactively, fluorescently, or with an enzyme such as alkaline phosphatase. The labeled antibody is used to determine whether there is a defective NF1 gene product or whether a tumor is of a defective NF1 gene origin. This can be carried out using any conventional technique. For example, a tissue sample can be liquified and tested against the labeled antibody using a conventional ELISA (enzyme-linked immunosorbent assay) format. Alternatively, human tissue samples (e.g., biopsy samples) can be tested for expression of the NF1 protein by other immunological techniques (17).

Immune complexes will be detected in normal samples which have antigens (e.g., NF1 polypeptide) reactive with anti-NF1 antibody. Samples which lack these antigens presumptively have a defect (e.g., mutation or a deletion) in the NF1 gene.

The present invention is further detailed in the following examples, which are offered by way of illustration and are not intended to limit the invention in any manner. Standard techniques well known in the art are utilized or the techniques specifically described below.

EXAMPLE 1

General Materials and Methods

A. Cell Lines

Epstein-Barr virus-transformed lymphoblastoid cell lines from normal and NF1 individuals were suspension-cultured in RPMI1640 medium (Cellgro/Mediatech), with 1% Nutridoma (Boehringer Mannheim), 5% bovine calf serum (Hyclone), and 50 units/ml gentamicin sulfate. The somatic cell hybrids used in this study were cultured in D-MEM media (Cellgro/ Mediatech) containing 10% fetal bovine serum (Hyclone), supplemented with hypoxanthine, aminopterin, and thymidine (HAT, Boehringer Mannheim) to selectively retain chromosome 17, except that hybrid 123B was cultured without HAT.

B. Genetic Linkage Analysis

Genotypic data were entered into a computer data base, and the output listings were checked against the autoradiograms to avoid clerical errors. In addition, all data for recombination of closely linked markers were re-inspected to determine whether misidentification of parents or grandparents was inflating recombination estimates.

Linkage analysis was performed with the LINKAGE program, which provides an iterative method for determining a probable gene order and likely alternatives (18).

C. Genomic Libraries

Genomic libraries were prepared from Sau3A partial digests of genomic DNA, fractionated on 10–40% sucrose gradients (19) and cloned into bacteriophage or cosmid vectors. Phage lifts were carried out with 0.45-μM Biotrans filters (Pall Biodyne) by the method of Benton and Davis (20). Cosmid colonies were lifted onto 1.2-μM Biotrans filters (Pall Biodyne) by the method of Grunstein and Hogness (21).

D. Southern Analysis

Restriction enzyme digests were carried out according to instructions supplied by the manufacturer (Molecular Biology Resources), except that units were used in two-fold excess. Restriction enzyme-digested samples were fractionated on 1% agarose gels in Tris-Acetate buffer. Gels were denatured in 0.4N NaOH for 30 minutes, neutralized in 2×SSC, 0.2M Tris pH 7.5 for 20 minutes and transferred to Gelman Biotrace RP filters in 50 mM Sodium Phosphate. Membranes were UV crosslinked immediately after transfer.

DNAs for PFGE analysis were prepared in low-melting-point agarose (22), and analyzed by transverse alternating field electrophoresis. PFGE took place in 1.0% agarose gels in 0.5X TBE buffer; DNA gels were depurinated by two 5 min washes in 0.25M HCl immediately before transfer, soaked 30 minutes in 0.4N NaOH, transferred 6–16 hours on Hybond N+, washed twice in 2×SSC 15 minutes ×2 and air dried.

Radiolabeling of DNA probes was done according to Feinberg and Vogelstein (24). Blots were prehybridized in 10% polyethylene glycol (PEG), 8% SDS and 500 μg/ml of total human DNA for two to 12 hours prior to hybridization with probe that was also prehybridized. In addition to total human DNA the probe was prehybridized with vector DNA to decrease background. When genomic cosmids were used as probes, the membranes were washed in 2×SSC, 0.1% SDS at room temperature for 30 to 120 minutes before exposure to X-Omat AR film with an intensifying screen at −70°. When cDNAs were used as probes, the membranes were washed in 0.1×SSC, 0.1% 505 at 55°–65° C.

E. cDNA Libraries and Plaque Screening

A normal adult male peripheral blood leukocyte oligo-(dT)-primed cDNA library in gt10, catalogue number HL1062A, was purchased from Clonetech Laboratories, Inc., (Palo Alto, Calif.) A human fetal brain oligo(dT)- and random-primed cDNA library in lambda Zap II, catalogue number 936206, from a 17–18 week late abortion normal female and a mouse macrophage WEHI-3 cell line oligo dT-primed cDNA library in Zap II, catalogue number 936304 were purchased from Stratagene (San Diego, Calif.). A fetal brain oligo dT-primed λgt10 size-selected cDNA library from Genentech was also screened. Phage from the libraries were incubated with *E. coli* strain LE392 and plated according to the manufacturer's instructions. Duplicate plaque lifts were made with 0.2-micron pore size Biotrans filters (Pall Biodyne) by the method of Benton and Davis (20).

Radiolabeling of DNA probes was done according to Feinberg and Vogelstein (24). First, cosmid and cDNA insert were separated from vector by restriction enzyme digestion and gel electrophoresis in low melting agarose (NuSieve GTG agarose, FMC Bioproducts, Rockland, Me.). DNA in gel slices was used directly for radiolabeling. The cDNA library filters were prehybridized in 50% formamide, 5×SSC, 50 mM sodium phoshate (pH6.5), 2× Denhardt's solution and 500 μg/ml sheared, denatured human DNA a 42° C. for two hours. Separate prehybridization of the radiolabeled probes was simultaneously carried out in a solution of the same composition except 50 μg/ml of DNA from the vector used to clone the probe was included. After prehybridization the probe and the filters were combined and hybridization was carried out for 4–16 hours at 42° C. Washes were in 2×SSC, 0.1% SDS at room temperature for 30 minutes three times. The mouse cDNA library was screened in aqueous hybridization conditions, 5×SSCP, 0.1% SDS at 65° C. and washed with 1×SSCP, 0.1% SDS at 65° C. After washing, filters were placed in Saran wrap and exposed on X-Omat AR film with an intensifying screen at −70° C.

F. PCR Amplification cDNA clone inserts were amplified in the polymerase chain reaction under standard conditions (25). The λ Zap clones were amplified with the −21M13 universal primer (GTAAAACGACGGCCAGT) and the reverse primer from Bluescript polylinker sequence (AACAGCTATGACCATG). The λgt10 clones were amplified with vector based primers GT10FP (AGCAAGTTCAGCTGGTTAAGT) and GT10RP (TTATGAGTATTTCTTCCAGGGT) synthesized by E. Meenen, Howard Hughes Medical Institute. Purified plaque suspensions were diluted 1:70, heated to 70° C. for 10 minutes and 10 μl was used in a 50 μl reaction volume. The amplification conditions were 50° C. annealing for 1 minute, 72° C. extension for 3.5 minutes and 94° C. for 1 minute for 30 cycles. Products were either digested with EcoRI and electrophoresed through low melting agarose or ultrafiltrated with Centricon 100 centrifuge columns prior to radiolabelling.

G. RNA Preparation and Northern Analysis

RNA was extracted from tissue by guanidinium-acid-phenol method as described by Chomczynski and Sacchi (26). Total RNA was electrophoresed through 1% agarose gels containing 0.37M formaldehyde (27) and blotted overnight onto uncharged nylon membrane. Probe preparation and hybridization was performed as per above methods.

H. cDNA Sequencing

All DNA sequencing was based on the dideoxy termination method of Sanger et al. (28). Double-stranded plasmid preparations of cDNA clones FB4, FB8, FB13, FB18 and FB20 in Bluescript SK(-) were made by the cesium chloride-ethidium bromide centrifugation method (12), denatured by treatment with 0.2N NaOH, neutralized, and sequenced from M13 and cDNA sequence-specific primers using the T7 polymerase sequencing kit 27-1682-01 (Pharmacia). DNA sequence was also generated on these cDNA clones from minilysate supercoiled preparations (29). cDNA clones FB35, FB37 and FB38 (in λgt10), and FB20 and FB4 (in λZap) were symmetrically amplified from plaques using specific vector-based forward and reverse primers with exon-specific primers generated from previous DNA sequence. The amplified products were asymmetrically amplified and the single strands were sequenced either manually or with fluorescently tagged M13 primers on an Applied Biosystems Inc. Model 370A DNA Sequencer (Applied Biosystems, Inc., Foster City, Calif.), using T7 DNA polymerase or Taq DNA polymerase. cDNA FB9 was symmetrically amplified with M13 primers and cDNA sequence specific primers for asymmetric PCR sequencing. DNA sequencing using the primer walk strategy gave overlapping clone cDNA sequence which was merged using the IntelliGenetics suite of programs (IntelliGenetics Inc., Mountain View, Calif.) running on a VAX computer. DNA sequences were aligned, examined for open reading frames and compared to DNA sequences in the EMBL and GENBANK databases and the PIR and SWISS protein databases.

Oligonucleotide primers for sequencing and enzymatic amplification were synthesized on an Applied Biosystems 380B DNA Synthesizer using 0.2 μmgl scale synthesis.

I. Sequencing of cosmid clones

DNA sequence from cosmid clone cEVI20 was obtained by multiplexed dideoxy sequencing of random subclones (30). cEVI20 DNA was sonicated, size fractionated (500–1000 bp) on agarose gels, and blunt-end ligated to a set of 10 vectors carrying multiplex identifier tag sequences (pKZ vectors). 720 primary clones were isolated (72/vector) and distributed into 72 mixtures, each containing 10 clones (one clone for each of the 10 vectors). Plasmid DNA pools were prepared and then sequenced as mixtures. Chain extension and termination with T7 DNA polymerase (Sequenase, U.S. Biochemicals) were primed simultaneously from two sites directly flanking the unique identifier tags and inserts, resulting in a mixture of 20 sequence ladders/reaction. These mixed sequences were electroblotted from standard sequencing gels onto GeneScreen nylon membranes, and probed sequentially with oligonucleotides complementary to the 20 nucleotide identifier tags. A total of 690 readable sequence ladders were recovered from twenty probings; these 125,172 nucleotides melded into 61 contigs (approximate total melded sequence=38,000 nucleotides), covering approx. 90% of cEVI20. The sequence of the 9 kb EcoR1 fragment containing the 5′ non-coding exon of EVI2 and exons 1 and 2 of the TBR cDNA was completed on both strands (actual size=8840 nucleotides) by augmenting the sequence data recovered from the sonicated clones with 27,335 nucleotides of sequence generated from 96 isolates of the 9 kb EcoRI fragment, each containing a random insert of a Tn3-based multiplexed transposable sequencing vector. The sequence of the 3.8 kb EcoRI fragment from cT311 was generated by a combination of random clones from the cEVI20 multiplexed pool and Tn3-based multiplexed sequencing vector inserts into a 3.8 kb EcoRI subclone. Gaps were closed in both of these case by selected primer walking.

Contigs were melded using the GEL program in IntelliGenetics package implemented on a VAX 8600. FASTA searches (31) of the National Biomedical Research Foundation (NBRF) protein sequence database (Release 19.0, 6/89) and translated GenBank (Release 61.0) and EMBL (Release 19.0) databases were performed with the conceptual translation of the TBR open reading frame. The PAM250 matrix was used in the second step of the comparison and the search was run using the UWGCG software package (32). FASTDB searches were also performed with the Intelligenetics package on GenBank (Release 62.0) and EMBL (Release 20.0) databases.

J. Patient Tissues

NF1 patients participating in this study met criteria agreed upon in a consensus conference at the National Institutes of Health (1). Lymphoblastoid cell lines from normal and NF1 individuals were established in the laboratory by transformation of peripheral blood mononuclear cells with Epstein-Barr-Virus. All human tissue samples used for research were obtained with the approval of the Institutional Review Board at the University of Utah Health Sciences Center.

K. Identification of SSCPs

PCRs were performed with the primer pairs listed in Table 1, with 100 ng of genomic DNA, 70 μM dNTPs, 0.5 μM primers, 1.5 mM $MgCl_2$, 10 mM Tris (pH 8.3), 50 mM KCl, 0.25 U of Taq polymerase, and 0.1 μl of [$\alpha$-$^{32}$P]dCTP (3000 Ci/mmole, 10 mCi/ml) in a volume of 10 μl. The product was then diluted 100 fold in 0.1% SDS, 10 mM EDTA, followed by a 1:1 dilution in 95% formamide, 20 mM EDTA, 0.05% bromphenol blue and 0.05% xylene cyanol. Once in this loading solution the samples were heated at 90° C. for 3 minutes to denature the DNA, then loaded onto 4.5% non-denaturing acrylamide gels (49:1 acrylamide: methylene-bis-acrylamide) measuring 38 cm×20 cm×0.4 mm, containing 90 mM Tris-borate (pH 8.3), 2 mM EDTA. Electrophoresis was carried out at 4° C. at 40 W, constant power. Samples were also screened under a second set of conditions, which consisted of the addition of 10% glycerol to the gel solution and performing the electrophoresis at room temperature.

After electrophoresis, the gel was transferred to 3 MM Whatman paper and dried on a vacuum slab gel dryer. Autoradiography with Kodak X-Omat AR film at −70° C., with an intensifying screen overnight was usually sufficient to allow detection of the PCR products.

L. Direct Sequencing of SSCP Alleles

Individual SSCP alleles were cut directly from the dried gel, placed in 100 μl of distilled water, incubated at 37° C. with shaking for one hour, and centrifuged briefly to pellet debris. An oliquat (10 μl) of the supernatant was then used directly in a 100 μl PCR reaction. The primers used in the original amplification were used in this amplification as well, except that the 5′ end of one primer contained additional sequence consisting of the universal sequencing primer from M13, and the 5′ end of the other primer included the sequence of the reverse sequencing primer.

The double-stranded PCR product resulting from this amplification was purified by two centrifugation-washes with a Centricon-100 column (Amicon), then sequenced following a test site protocol suggested by Applied Biosystems, Inc. (Foster City, Calif.). This involved performing the dideoxy-sequencing reactions with Taq polymerase in a thermal cycler, using fluorescently tagged M13 universal or reverse sequencing primers, followed by gel electrophoresis and data collection and analysis on an Applied Biosystems Model 373A automated sequencer.

M. Anchored-PCR cDNA Library

Anchored PCR, to obtain cDNA clones from the 5′ end of EVI2 mRNA, was performed as described by Lŏh et al. (41). For this purpose two oligonucleotide primers were constructed based on the furthest 5′ sequence shared by cDNA clones E-9 and E-34, and RNA was prepared from human brain frontal cortex. Following first-strand cDNA synthesis with the first EVI2-specific primer and addition of poly-dG tails with terminal transferase, the second, more 5′ primer was used for PCR together with an "anchored primer" containing poly-dC at its 3′ end. The amplified product was electrophoresed on a 2% low-melting agarose gel and visualized with ethidium bromide, revealing a heterogeneous set of products ranging from approximately 50 to 300 base pairs (bp). The gel lane was cut into slices 2 mm thick starting about cm above the region of highest molecular size that still contained visible product. 10 μl of each gel slice was subjected to PCR using the same pair or primers and analyzed by gel electrophoresis. The mobility of the products matched the order of the gel slices in the lane, and the first fraction showing visible product was cloned into Bluescript SK(+) (Stratagene, San Diego, Calif.) and transformed into DH5alphaF′ cells. Colonies were screened with an EVI2 probe still further 5′ in the known sequence; approximately 150 positive clones were identified in this way.

EXAMPLE 2

Mapping of the NF1 Locus to a 600 kb NruI Fragment

The NF1 gene was initially localized to chromosome 17 by linkage analysis (3,4) and to 17q11.2 by further linkage analysis with probe pHHH202 (6). Because intact chromosome 17 is too large (150,000,000 bp) for development of probes specifically targeted to the NF1 region, pHHH202 and other elements of a chromosome 17 map (33) were used to characterize a large number of human X rat microcell hybrids (34,35) that had been created by fusion of a somatic cell hybrid containing a neo-marked human chromosome 17 and a rat cell line (36). To avoid confusion caused by undetected deletions or rearrangements, new probes were searched for in cosmid libraries prepared from the two microcell hybrids that best represented the NF1 region, 7AE-11(6) and FTHB(17)L4. The FTH(17) series microcell hybrids were constructed by transferring human chromosome 17 from diploid fibroblasts into thymidine kinase-deficient (TK−) rat FT-1 cells (34) and selecting the $T^+$ phenotype in HAT (hypoxanthine, aminopterin thymidine) medium. One of these lines, FTH(17)L, was then cultured in bromodeoxyuridine (BrdU) (20 μg/ml) to select subclones in which TK-linked sequences were removed. Ten BrdU-resistant subclones were isolated from this primary clone, FTHB(17)L1 through L10. All cells were cultured in 1:1 Ham's F12:Dulbecco's modified Eagle's medium with 10% fetal bovine serum without antibiotics (34). The FTHB(17)L4 cell line, containing the pericentromeric region of chromosome 17, was propagated in medium supplemented with HAT.

Human cosmids identified by screening the microcell hybrid libraries with labeled human DNA were physically mapped by means of a panel that included somatic cell hybrids (37), the two chromosome 17 microcell hybrids AE-11 and FTHB(17)L4, and two cell lines with NF1 translocation break-points. One of the translocation cell lines, F13 (6,7), contains the derivative 22 der(22)] chromosome from a sporadic NF1 patient who carries a balanced translocation between chromosomes 17 and 22, t(17;22)(q11.2;q11.2). The other hybrid, designated DCR1, was isolated from a fusion of lymphoblasts from an NF1 patient with a balanced translocation between chromosomes 1 and 17, t(l;17)(p34.3;q11.2) (9) and contains the der(1) chromosome from this patient (11).

The relationship of clones in the NF1 region to NF1 was determined by a combination of genetic and physical mapping. A high-resolution genetic map for the NF1 region (6) indicated that two probes, pTH17.19 and c11-2C11, flank NF1 about 2 centimorgans apart. Given the density of cosmid probes within the target regions, it should be possible to detect abnormal pulsed-field fragments in the two NF1 patients with balanced translocations. DNA samples from normal individuals, patients with sporadic NF1 , the two patients with balanced translocations, and somatic cell hybrids were prepared in agarose blocks, digested with a number of rarely cutting enzymes, and subjected to pulsed-field gel electrophoresis (PFGE) (14).

One region 3 clone, c11-1F10, hybridized to a 600 kb NruI fragment. When tested on PFGE blots (15) prepared with DNA from the patients with translocations, the clone showed new, translocation-specific NruI fragments. The t(17;22) cell line showed the normal 600 kb NruI fragment plus a fragment of 390 kb. The t(1;17) cell line gave the normal 600 kb NruI fragment plus a fragment of 450 kb.

EXAMPLE 3

Mapping of the 600 kb NruI Fragment

Hybridization of a human genomic library with an evolutionarily well-conserved, unique-sequence murine genomic probe for the Evi-2 locus, pXS1.9, identified a human genomic DNA clone, phage HU39. A subclone of phage HU39, pHU39.3, revealed a two-allele EcoRI restriction fragment length polymorphism (RFLP) with a major allele of 8 kilobases (kb) and a minor allele of 5 kb. Following the conventions for human nomenclature, the human locus is referred to as EVI2. This locus is contained in the human genomic segment in a cosmid, cEVI36. This marker had an observed heterozygosity of 0.45 in 100 unrelated individuals typed. Linkage analysis gave a maximum Lod score of 16.1 at zero recombination between the locus identified by pHU39.3 and the locus defined by c11-2C11, a cosmid previously shown to be tightly linked to NF1 (6).

Somatic cell hybrid lines containing NF1 translocation chromosomes provide an independent means of precisely mapping genes that may be close to NF1. The cell line NF13 contains the derivative chromosome 22 [der(22)] from an NF1 patient with a balanced translocation, t(17;22) (q11.2; q11.2) (7). Cell line DCR1 contains the derivative chromosome 1 [der(1)] from an NF1 patient with a different balanced translocation, t(1;17) (p34.3;q11.2) (11).

The insert from cEVI36 was used to screen an oligo-(dT)-primed cDNA library from normal human bone marrow in λgt10. Thirteen positive clones (from 1 million plated plaques) were picked and plaque-purified; rescreening these 13 with the murine Evi-2 cDNA BK3 as probe identified four as being related to Evi-2. The largest of these four clones, cDNA E-9, contained a 5.1-kb insert. Clone E-9.4 is a 1.8 Kb subclone from the 31-end of clone E-9. Hybridization of the E-9 insert to genomic DNA detected a single, 15 kb BglII fragment, which maps between the translocation breakpoints of the two NF1 patients.

To identify additional EVI2 cDNA clones, fragment E-9.4 was used to screen an oligo-(dT)-primed cDNA library from normal human frontal cortex in λ Zap TM. Three independent positive clones were isolated, plaque-purified, and sequenced. The largest of these, E-34, is 1522 bp long and contains within it the 1110 bp of sequence at the 3′ end of the E-9 clone. The E-34 sequence continues 3′ of this shared region for another 146 bp, then terminates with a run of 12 A-residues. The 88-bp segment in E-34 just 5′ of the 1110 bp shared region, however, appears to be an inverse complement of the corresponding 88 bp in E-9 just 5′ of the shared region. The remaining sequence of 178 bp at the 5′ end of E-34 detected no transcript on RNA blots, showed no homology to any part of E-9, and did not hybridize to Southern transfers of chromosome 17 DNA.

To identify additional sequences from the 5′ end of the mRNA, the anchored polymerase chain reaction (PCR) (40,41) was used to construct a set of frontal-cortex cDNA clones enriched for the 5′ end of EVI2. We initiated first-strand cDNA synthesis on frontal-cortex RNA with a primer complementary to sense-strand sequence shared by E-34 and E-9. Three of the largest resulting cDNA clones were sequenced and found to be a nested overlapping set. The largest of these, 341 bp, is E-An7. The last 138 bp at its 5′ end is sequence not found in either E-9 or E-34; this sequence used as a probe detects the same 1.6 kb transcript that is detected by E-9.

It was determined that E-9 sequences are missing from the t(17:22) breakpoint chromosome (NF13) but are present in the t(1:17) breakpoint chromosome (DCR1). This single-copy human locus therefore maps to a region between the NF1 translocation breakpoints. This result also locates the t(17:22) breakpoint distal to the t(1:17) breakpoint FIG. 1 shows the PFGE-derived map of the region, deduced from the fragment mobilities of p17L1A, cEVI2 and c11-F10 after individual digestion with BsshII, ClaI, NotI, SacII, and with digestions with BsshII/NotI, ClaI/NotI, NruI/NotI and SacII/NotI. The approximate positions of the NF1 translocations are shown. Several HTF islands (39) are indicated by the clusters of restriction sites for enzymes with CpG dimers in their recognition sites. The order centromere—17L1A—t(1;17) t(17;22) 11-1F10—telomere is indicated by the mapping of between the EVI2 between the translocation breakpoints, with 17L1A proximal and 11-1F10 distal to both breakpoints.

Figure 2:
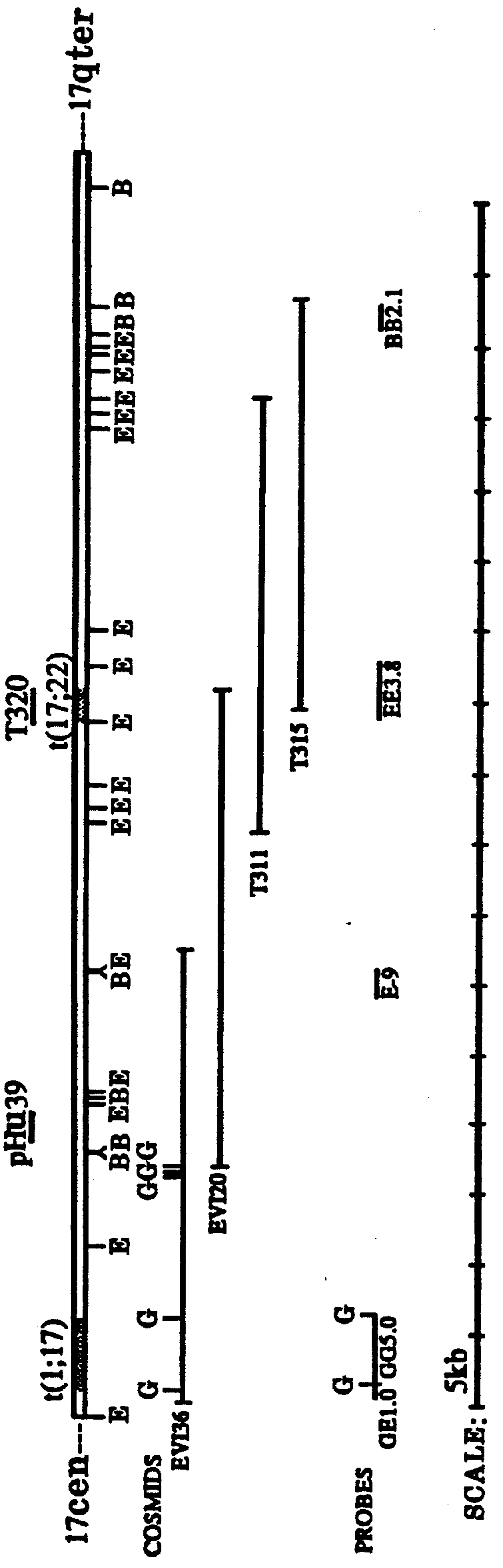
FIG. 2 is a cosmid contig and restriction enzyme map of the NF1 region. E=EcoRI; B=BamHI; G=BglII. Probes used to ascertain cosmid clones are shown above; probes used to test somatic cell hybrid panels are shown below.

In order to better localize the NF1 translocation breakpoints and provide probes for identifying transcribed regions, cosmid-walking experiments were undertaken. Radiolabelled pHU39.3 identified two contiguous human cosmid clones, designated cEVI20 and cEVI36, from human genomic library cloned in a derivative of pWE15. A second walk with a radiolabelled 2.1 kb EcoRI subclone (pT320) from the end of cEVI20 identified two additional overlapping cosmids, designated cT311 and cT315. Overlapping cosmids cEVI37, cT316 and c7D5 were also obtained. Restriction mapping experiments with these clones resulted in the cosmid contig map shown in FIGS. 2 and 3D, spanning approximately 80 kb and 130 kb of genomic DNA, respectively.

A series of probes spanning the cosmid contig were tested against DNA blots of the BamHI, BglII and EcoRI-digested DNA from a NF1 translocation somatic cell hybrid panel. Probe E-9, which is homologous to the 9-kb EcoRI fragment shown in FIG. 2, which reflects sequences found in both cEVI20 and cEVI36, maps between the translocation breakpoints because it is absent in hybrid NF13 and present in hybrid DCR1. Probe GE1.0 is a 1 kb BglII/EcoRI restriction fragment from cEVI36. It detects an 11.5 kb genomic EcoRI fragment that maps to chromosome 17q, but is absent in both translocation hybrids. Therefore, this fragment of cEVI36 must map proximal to both translocation breakpoints, which means that cEVI36 spans the t(1;17) breakpoint. Since probe BB2.1, a 2.1 kb genomic BamHl fragment contained within cT315, maps to chromosome 17q and also is present in both translocation hybrids, it is telomeric of both breakpoints. The contig, therefore, must span both NF1 translocations, and is oriented with cEVI36 closest to the centromere. The t(1;17) breakpoint is localized within the contig by probe GG5.0, a 5 kb BglII fragment from cEVI36, which is adjacent to probe GE1.0 and detects the same 11.5 kb genomic EcoRI fragment. Unlike probe GE1.0, probe GG5.0 is present in hybrid DCR1, but on a 7.8 kb derivative EcoRI fragment that resulted from the translocation event, and absent from NF13.

The t(17;22) breakpoint is localized by probe EE3.8, a 3.8 kb EcoRI fragment from cT311. In hybrid NF13, a 15 kb derivative fragment is present instead of the normal 3.8 kb EcoRI fragment. An identical result was obtained when this experiment was repeated with the most distal 2.3 kb EcoRI fragment from cEVI20, indicating the position of the t(17;22) breakpoint lies within cEVI20. The two NF1 translocation breakpoints thus define a candidate region for NF1 of some 60 kb. The strong cross-hybridization of probe EE3.8 with a 3.35 kb murine genomic fragment suggests an evolutionary conservation cf sequences in this region.

EXAMPLE 4

Identification of Interstitial Deletion Mutations

Figures 4A, 4B, 4C:
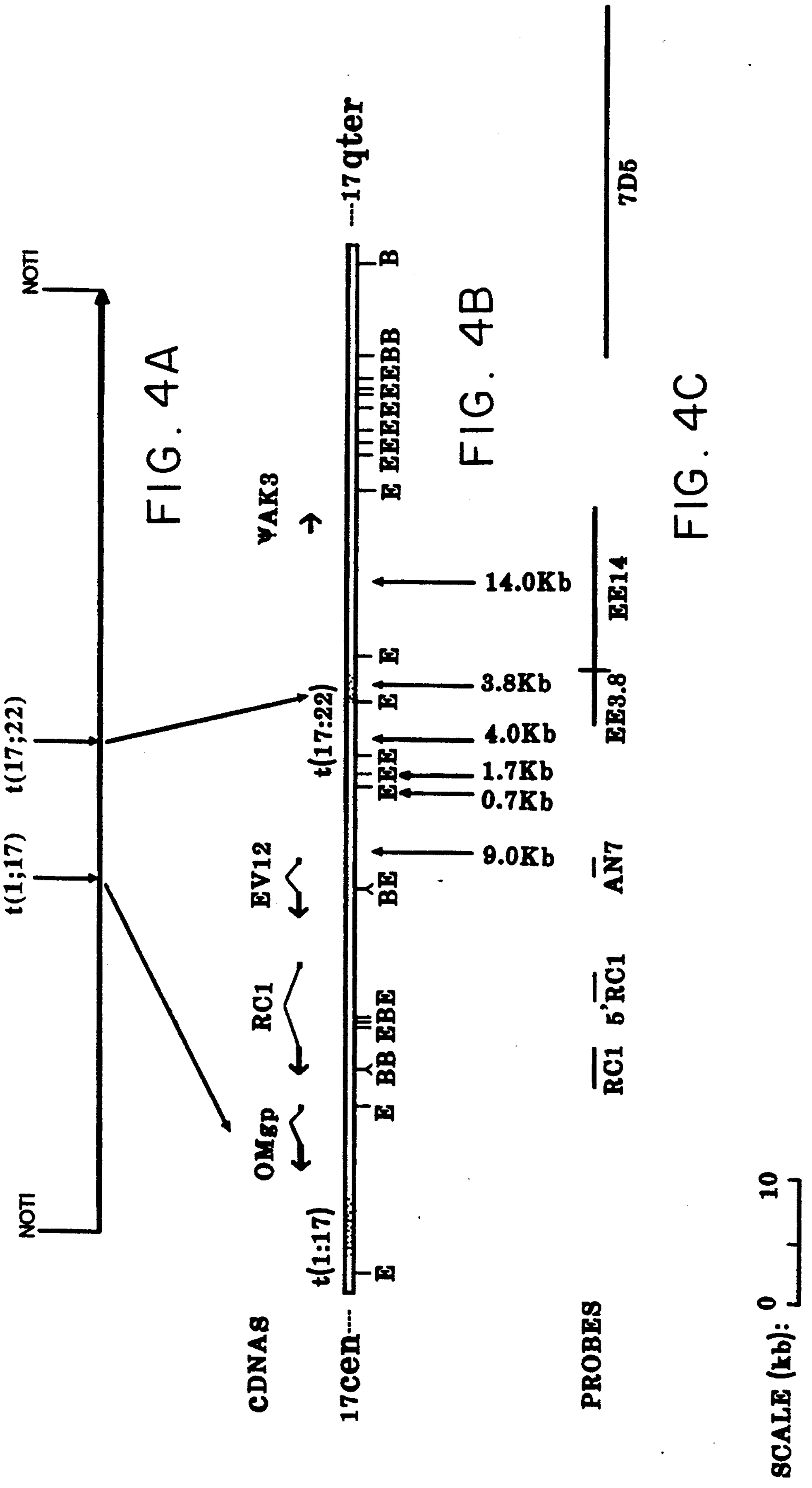
FIG. 4 is a diagrammatic representation of the NF1 translocation region. A. NotI PFGE fragment spanning the NF1 translocation region, showing the positions of the NF1 translocations. B. Detail of the NF1 translocation region. The sizes (in kb) of EcoRI fragments referred to in the text are shown below the restriction enzyme map, (E) EcoRI sites: (B) BamHI sites. C. Probes used in analysis of the NF1 patient deletions are shown according to their position on the NF1 region map.

Genomic DNA from NF1 individuals was examined both by pulsed field gel electrophoresis (PFGE, 22) and by standard Southern blotting. The map locations of the NF1 region cosmids and probes used for the deletion studies are presented in FIG. 4. A 390 kb NotI fragment spans two NF1 translocations (10,8). This Notl fragment had been previously examined in 38 NF1 patients, with no remarkable findings.

Figure 5A:
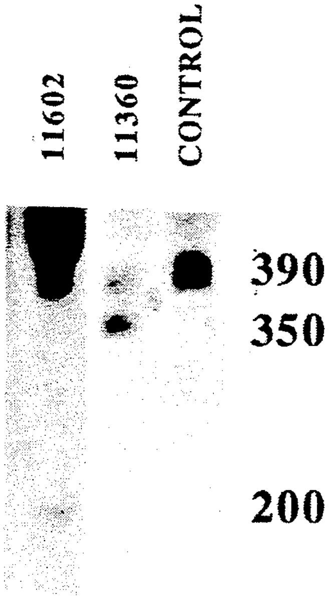
FIG. 5 illustrates a deletion analysis of NF1 patients. A. PFGE analysis of NotI digested NF1 patient DNA. The autoradiograph shows Southern blot of a control, NF1 patient 11360 and NF1 patient 11602 probed with radiolabelled cosmid 7D5. Mobilities of normal and abnormal NotI fragments are indicated in kb. B. PFGE characterization of NF1 patient 11360 deletion. The autoradiographs show a Southern blot of NotI digested NF1 patient 11360 DNA probed successively with probes RC1, 5'-RC1 and EE14. Mobilities of NotI fragments are indicated in kb. C. Deletion analysis of NF1 patient 11573. The autoradiographs show southern blots of EcoRI digested DNA from NF1 patient 11573 and a control successively probed with RC1, AN7 (the 5'-end of EVI2), and EE3.8. EcoRI fragment mobilities are indicated in kb.

For these experiments, the panel was expanded to 54 NF1 patients (including 30 patients previously examined), and the PFGE pulse time was reduced from 70 seconds to 20 seconds to maximize resolution in the lower molecular weight range. As can be seen in FIG. 5A, patient 11360 shows a novel NotI fragment not previously resolved and patient 11602, not previously screened, also shows a novel NotI fragment when probed with cosmid 7D5 from the distal end of the 390 kb NotI fragment. The new NotI fragments are of lengths 350 kb and 200 kb, consistent with deletions of the NF1 region of 40 and 190 kb, respectively. It is unlikely this site is polymorphic because these bands have not been observed in 52 other NF1 individuals.

The 190 kb deletion in patient 11602 has not been precisely mapped within the 390 kb NotI fragment. Preliminary experiments indicate a 50% reduction in intensity with each of the probes for OMGP, RC1, EVI2 and TBR, suggesting that this deletion spans the entire 60-kb region between the two translocation breakpoints. The endpoints of the deletion have not been defined. While this mutation helps define the NF1 locus, the size of the deletion precludes its use in specifically identifying the NF1 gene, as several known genes are included.

Figure 5B:
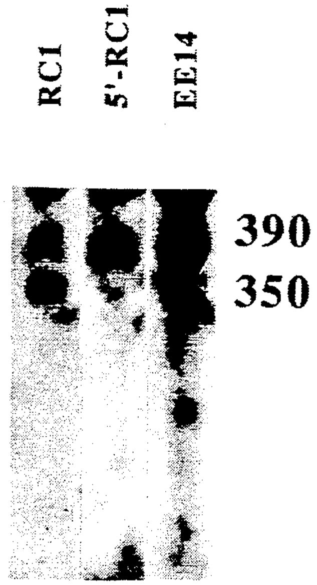

The 40 kb deletion in patient 11360 was more specifically localized to determine whether any of the known genes in the region were included. FIG. 5A shows NotI PFGE blots of patient 11360 tested with probes spanning the t(17;22) NF1 translocation. Probe RC1, containing the 3′ exon of this gene, detects the derivative NotI fragment from NF1 patient 11360 (FIG. 5B) and, therefore, does not lie within the deletion. A probe from the 5′-exon of RC1 (5′-RC1, FIG. 5B), however, does not reveal the derivative fragment and must be located within the deleted region. Probe EE3.8, which defines the TBR region, also does not detect the derivative NotI fragment of NF1 patient 11360, confirming its location within the deletion. Because probe EE14, just distal to probe EE3.8, does detect the derivative NotI fragment of patient 11360, its was concluded that the distal end-point of the deletion is in the 14 kb EcoRI fragment adjacent to the 3.8 kb translocation fragment, consistent with the estimated size of 40 kb for this deletion. Based on our previous mapping data, all of EVI2 must reside within the deleted region.

In order to search for deletions near the t(17;22) NF1 translocation breakpoint at greater resolution, EcoRI-digested DNA from patients and controls were probed with the 3.8 kb EcoRI fragment (EE3.8), previously shown to span the NF1 t(17;22) region. As seen in the right-hand panel of FIG. 5C, NF1 patient 11573 revealed an 8.8 kb derivative EcoRI fragment, in addition to the expected 3.8 kb EcoRI fragment, thus indicating the presence of a rearrangement. 80 other NF1 patient DNA blots were screened, and this 8.8 kb fragment was not observed therefore; it is unlikely that this derivative band is a polymorphism.

Figure 5C:
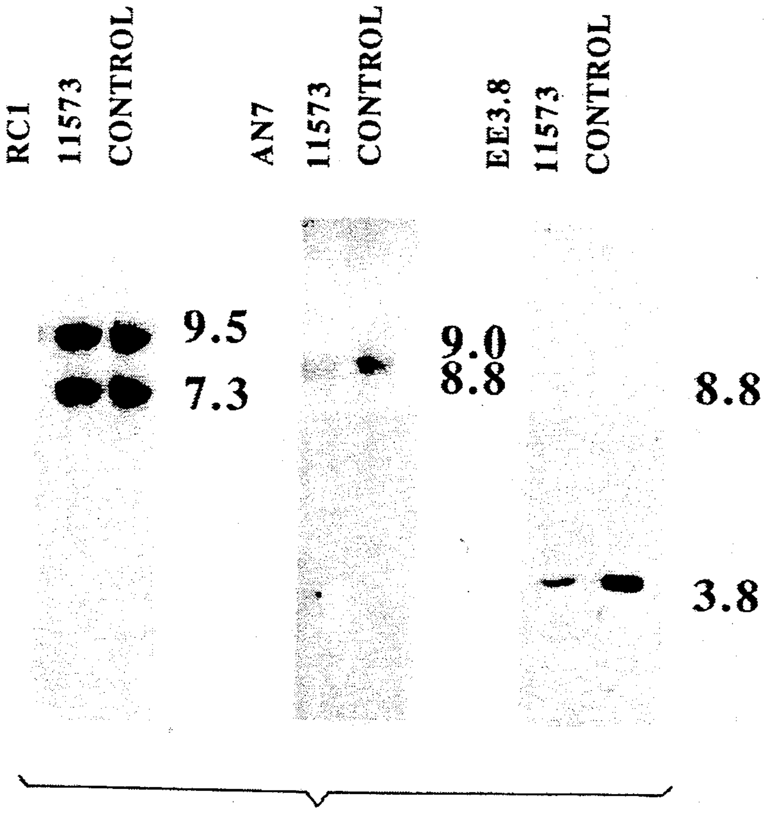

FIG. 5C shows the deletion analysis of patient 11573. Probes spanning the NF1 translocation region (see FIG. 4) were tested on Southern blots of EcoRI-digested DNA from patient 11573 and controls. Probe RC1 detects, and is wholly contained within, a previously characterized, polymorphic EcoRI fragment (A1=9.5 kb, A2=7.3 kb, the same as detected by probe HU39.3). Because patient 11573 shows both alleles (as does the control, left-hand panel of FIG. 5C), RC1 must lie outside the deletion. Probe An-7 contains the 5′ exon of the EVI2 gene and detects the same 8.8-kb derivative EcoRI fragment as probe EE3.8 (FIG. 5C, center panel), in addition to the normal 9 kb EcoRI fragment, consistent with a location outside the deletion. Therefore, the deletion is distal to EVI2, removing approximately 11 kb of genomic DNA, but none of the genes known for the region, and continues into the EcoRI fragment identified by probe EE3.8.

EXAMPLE 5

Identification of cDNAs

The 3.8 kb EcoRI fragment (probe EE3.8), which is partially deleted in patient 11573, spans the translocation breakpoint and strongly hybridizes to a 3.35 kb EcoRI mouse band on Southern blots of DNA from somatic cell hybrids. Because interspecific conservation often indicates the presence of a gene, probe EE3.8 was used to screen several cDNA libraries. A 2.1 kb TBR cDNA clone, mDVI, was obtained from a murine macrophage cDNA library. The EcoRI insert released from mDVI was then used to screen additional human cDNA libraries. Thirty TBR cDNA clones were identified from two human fetal brain cDNA libraries (Stratagene, λ zap and Genentech, λgt10) and 12 TBR cDNA clones were identified from a peripheral blood cDNA library (Clonetech, λgt10). The sizes of the TBR cDNA inserts range from 0.8 to 3.2 kb and there is an EcoRI site in a subset of clones. On Northern analysis, preliminary examination of total RNA from a choriocarcinoma cell line with TBR cDNAs as probes reveals an 11 kb (and potentially a 2.6 kb, [FIG. 3A]) mRNA.

EXAMPLE 6

Mapping of the cDNA Clones

Figure 3B:
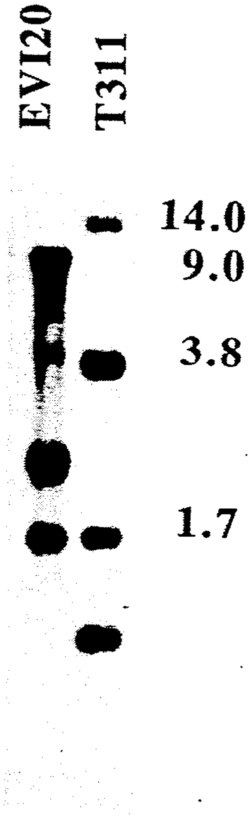
Figure 3C:
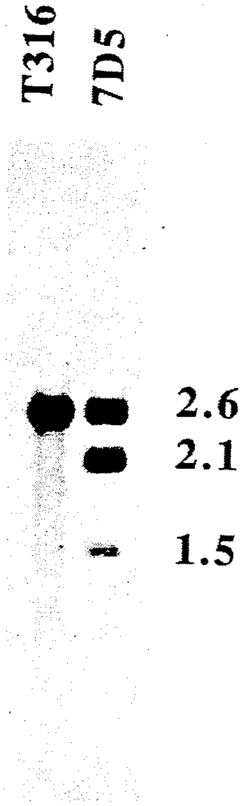
Figure 3D:
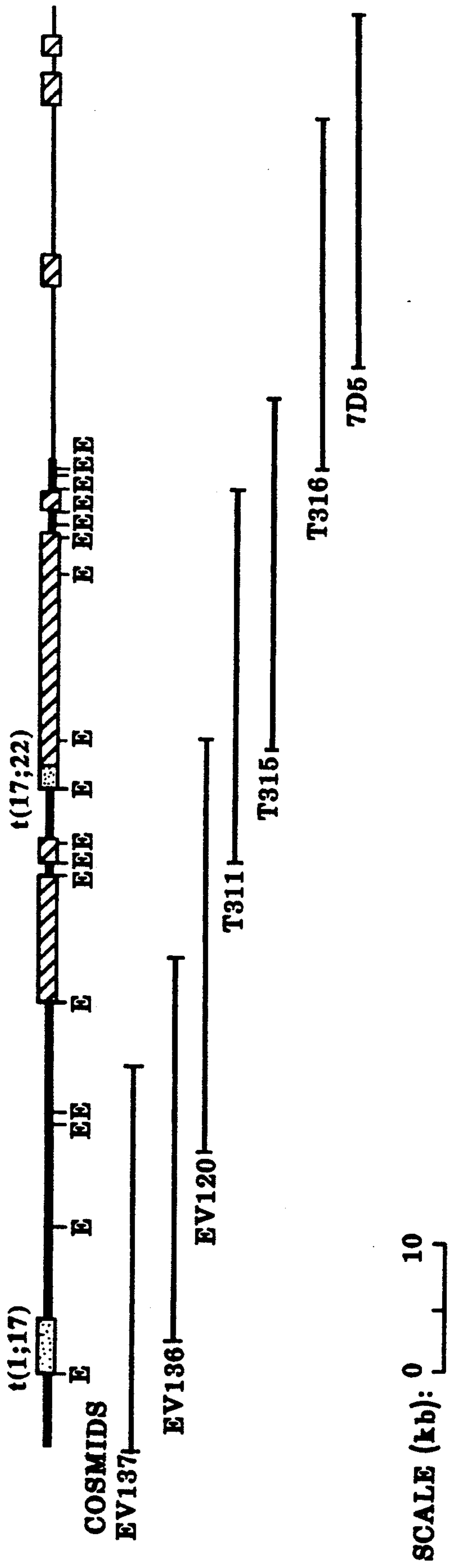

A meld of overlapping clones was constructed by Southern blot analysis. To generate probes, individual TBR cDNA clones were PCR amplified with insert-facing, vector-based primers. The PCR products were either labeled directly or were digested with EcoRI, subjected to electrophoresis in low-melting agarose, excised from the gel and radiolabeled. These inserts were hybridized to Southern blots of either cloned DNA from the genomic contig or amplification products of the other TBR cDNA inserts. Approximately 5 kb of overlapping cDNA sequence falls within a 100 kb genomic region spanned by overlapping cosmids and represented in our cosmid contig. FIGS. 3B and 3C are autoradiographs of Southern blot hybridizations showing the extent of the cDNA on the genomic map. The TBR fetal brain clone 17 (FB17) is 3.2 kb; it hybridizes to genomic EcoRI fragments of 9 kb and 1.7 kb in cosmid EVI20, and fragments of 3.8 kb and 14 kb in cosmid T311 The 2.3 kb fragment in cEVI20 and the 1.1 kb fragment in cT311 are truncated end fragments overlapping with the 3.8 kb and 9 kb genomic fragments, respectively. The 9 kb EcoRI fragment is the most centromeric fragment in the cosmid contig that hybridizes to the cDNA.

The telomeric extent of the TBR cDNA meld is defined by Southern blot analysis using an EcoRI fragment of the 2.1 kb TBR fetal brain cDNA clone 8 (FB8) as probe. This probe identifies three EcoRI fragments from cosmid clone 7D5 −2.6 kb, 2.1 kb and 1.5 kb- and one fragment of 2.6 kb from cosmid cT316 (see FIG. 3C). Cosmid 7D5 maps 30–35 kilobases telomeric of the t(17:22) NF1 translocation breakpoint and overlaps extensively with cT316 (see FIG. 3D). Because two of the three fragments identified by TBR cDNA FB8 are not contained in the overlapping T316 cosmid, they must map to the telomeric end of c7D5. This places the telomeric end of the TBR cDNA meld at least 60–65 kb telomeric of the t(17:22) translocation breakpoint.

Figure 6:
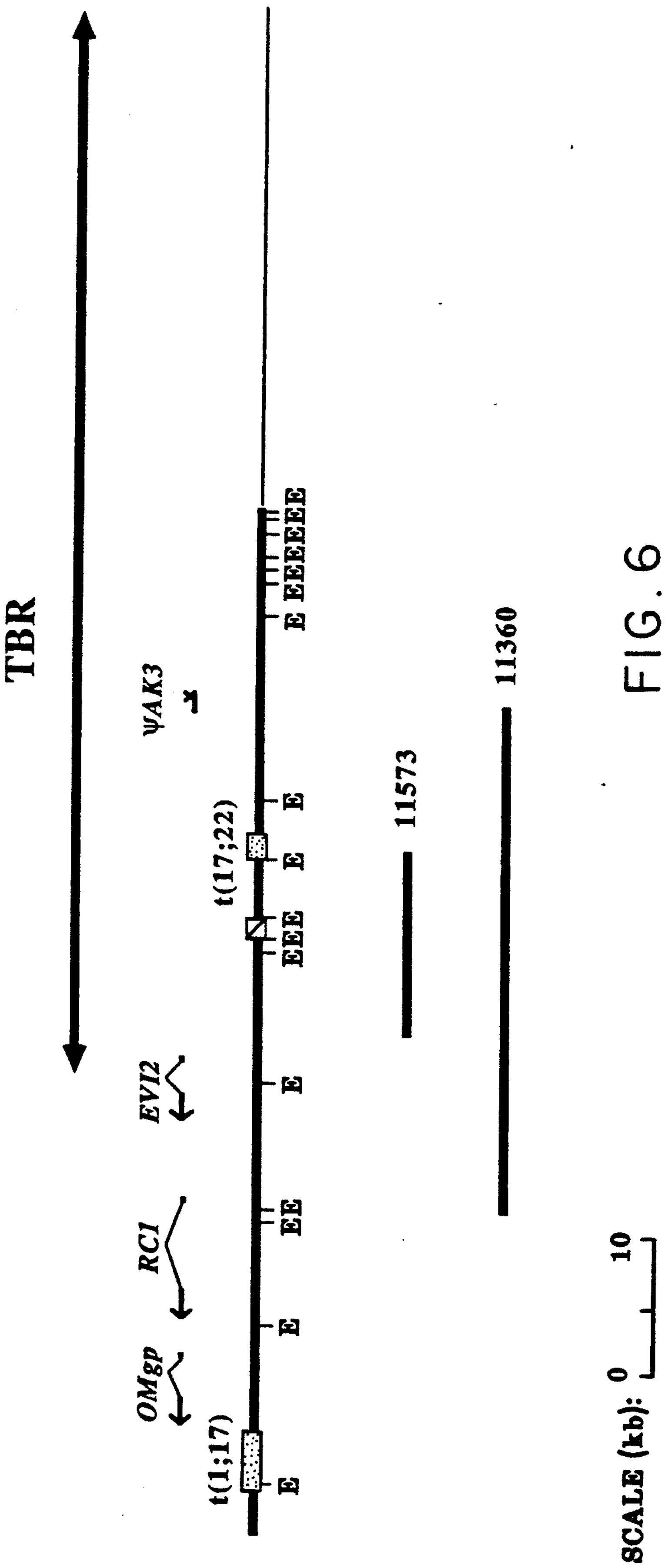
FIG. 6 diagrams the relationship of TBR to NF1 mutations. Map of the NF1 region showing the extent of deletions seen in NF1 patients 11360 and 11573 (horizontal lines, below), and the region of genomic DNA encompassed by the TBR cDNA clones analyzed herein. Note that the 1.7 kb EcoRI fragment in cEVI20 (cross-hatched) and the proximal end of the 3.8 kb EcoRI fragment spanning the t(17;22) translocation breakpoint (stippled), are within the NF1 patient 11573 deletion.

These results are consistent with the TBR gene mapping across the t(17;22) translocation breakpoint. It should be noted that the 1.7 kb genomic EcoRI fragment centromeric to the breakpoint fragment is deleted in patient 11573. The TBR cDNA mapping studies and the analysis of the NF1 deletions are summarized in FIG. 6.

EXAMPLE 7 cDNA Sequencing

Thirty cDNA clones reflecting sequences from the RNA transcript of the TBR gene had been previously isolated from human fetal brain libraries in the above examples. FIG. 7 shows the cDNA sequence obtained from the overlapping fetal brain clones FB4, FB6, FB8, FB9, FB13, FB16, FB18, FB20, FB35, FB37 and FB38. With one exception, DNA sequencing of overlapping fetal brain cDNAs has provided the continuous transcript sequence shown in FIG. 7. The exception is in one region of exon 3 where 118 bp of genomic sequence (see below) was used to join two cDNA sequences. No intron-exon boundaries were seen within the 118 bp of genomic sequence. There are no stop codons in the open reading frame of the sequence from position 3 to position 3309. It should be noted that a second open reading frame, phase shifted by one base, starts approximately 100 bp upstream from this stop codon and continues for approximately 600 bp past the stop codon. In addition, in one of the cDNA clones there is a 54 bp insertion between positions 3563 and 3564, downstream of the stop codon but suggesting inclusion of an additional exon through an alternate splicing of the message. None of the cDNA clones sequenced have a poly(A) tract at the cloning site and no two clones end with identical sequences. In addition, 22 bp at the 5' end of the merged DNA sequence shown in FIG. 7 is not found in exon 1 nor anywhere within the genomic sequence of the 9 Kb EcoRI fragment suggesting an exon located 51 of the EcoRI fragment. An approximate length of 11 Kb for the mRNA of the NF1 gene is suggested by preliminary Northern blot analysis. Consequently, the 4 kb cDNA meld is likely internal to the transcript that may be as large as 11 kb.

In view of the larger size of the mRNA, additional sequencing was performed. This sequencing yielded a total sequence of 6576 nucleotides as shown in Table 2. Table 2 shows the postulated amino acid sequences in each reading frame of this DNA sequence. There are no stop codons in the open reading frame of the sequence from position 142 to position 6285. The open reading frame beginning with methionine at position 166 of the DNA sequence is the NF1 gene, coding sequence. Although there is approximately 5 kb more DNA in the mRNA than in the sequence of Table 2 and it is possible that there could be additional coding sequence(s) within this DNA, there is currently no evidence of any. Thus, The DNA sequence of Table 2 is the coding sequence for the NF1 gene.

The predicted amino acid sequence of the large open reading frame found in the TBR cDNA was used to search for homology to known DNA and protein sequence. No significant homologies have been detected thus far.

TABLE 2

| | | | | | | | | | | | | | | | | | |
|---|---|---|---|---|---|---|---|---|---|---|---|---|---|---|---|---|---|
| | | | | | | | | 27 | | | | | | | | | 54 |
| GTA | TTT | AAT | ATA | CAT | CAA | GTT | TGA | AAC | TTG | GCT | GTA | GCT | GAT | TGA | TGT | TTA | GCT |
| Val | Phe | Asn | Ile | His | Gln | Val | . | Asn | Leu | Ala | Val | Ala | Asp | . | Cys | Leu | Ala |
| Tyr | Leu | Ile | Tyr | Ile | Lys | Phe | Glu | Thr | Trp | Leu | . | Leu | Ile | Asp | Val | . | Leu |
| Ile | . | Tyr | Thr | Ser | Ser | Leu | Lys | Leu | Gly | Cys | Ser | . | Leu | MET | Phe | Ser | Ser |
| | | | | | | | | 81 | | | | | | | | | 108 |
| CTA | GAC | TAA | GTT | GCT | TTC | AAG | TGA | TAA | TTG | CCT | TCA | TTT | TAG | GCT | TGG | GAA | GAT |
| Leu | Asp | . | Val | Ala | Phe | Lys | . | . | Leu | Pro | Ser | Phe | . | Ala | Trp | Glu | Asp |
| . | Thr | Lys | Leu | Leu | Ser | Ser | Asp | Asn | Cys | Leu | His | Phe | Arg | Leu | Gly | Lys | Ile |
| Arg | Leu | Ser | Cys | Phe | Gln | Val | Ile | Ile | Ala | Phe | Ile | Leu | Gly | Leu | Gly | Arg | Tyr |
| | | | | | | | | 135 | | | | | | | | | 162 |
| ACA | CAT | GCA | AAA | TGG | GAA | CAA | GCA | ACA | AAG | CTA | ATC | CTT | AAC | TAT | CCA | AAA | GCC |
| Thr | His | Ala | Lys | Trp | Glu | Gln | Ala | Thr | Lys | Leu | Ile | Leu | Asn | Tyr | Pro | Lys | Ala |
| His | MET | Gln | Asn | Gly | Asn | Lys | Gln | Gln | Ser | . | Ser | Leu | Thr | Ile | Gln | Lys | Pro |
| Thr | Cys | Lys | MET | Gly | Thr | Ser | Asn | Lys | Ala | Asn | Pro | . | Leu | Ser | Lys | Ser | Gln |
| | | | | | | | | 189 | | | | | | | | | 216 |
| AAA | ATG | GAA | GAT | GGC | CAG | GCT | GCT | GAA | AGC | CTT | CAC | AAG | ACC | ATT | GTT | AAG | AGG |
| Lys | MET | Glu | Asp | Gly | Gln | Ala | Ala | Glu | Ser | Leu | His | Lys | Thr | Ile | Val | Lys | Arg |
| Lys | Trp | Lys | MET | Ala | Arg | Leu | Leu | Lys | Ala | Phe | Thr | Arg | Pro | Leu | Leu | Arg | Gly |
| Asn | Gly | Arg | Trp | Pro | Gly | Cys | . | Lys | Pro | Ser | Gln | Asp | His | Cys | . | Glu | Ala |
| | | | | | | | | 243 | | | | | | | | | 270 |
| CGA | ATG | TCC | CAT | GTG | AGT | GGA | GGA | GGA | TCC | ATA | GAT | TTG | TCT | GAC | ACA | GAC | TCC |
| Arg | MET | Ser | His | Val | Ser | Gly | Gly | Gly | Ser | Ile | Asp | Leu | Ser | Asp | Thr | Asp | Ser |
| Glu | Cys | Pro | MET | . | Val | Glu | Glu | Asp | Pro | . | Ile | Cys | Leu | Thr | Gln | Thr | Pro |
| Asn | Val | Pro | Cys | Glu | Trp | Arg | Arg | Ile | His | Arg | Phe | Val | . | His | Arg | Leu | Pro |
| | | | | | | | | 297 | | | | | | | | | 324 |
| CTA | CAG | GAA | TGG | ATC | AAC | ATG | ACT | GGC | TTC | CTT | TGT | GCC | CTT | GGA | GGA | GTG | TGC |
| Leu | Gln | Glu | Trp | Ile | Asn | MET | Thr | Gly | Phe | Leu | Cys | Ala | Leu | Gly | Gly | Val | Cys |
| Tyr | Arg | Asn | Gly | Ser | Thr | . | Leu | Ala | Ser | Phe | Val | Pro | Leu | Glu | Glu | Cys | Ala |
| Thr | Gly | MET | Asp | Gln | His | Asp | Trp | Leu | Pro | Leu | Cys | Pro | Trp | Arg | Ser | Val | Pro |
| | | | | | | | | 351 | | | | | | | | | 378 |
| CTC | CAG | CAG | AGA | AGC | AAT | TCT | GGC | CTG | GCA | ACC | TAT | AGC | CCA | CCC | ATG | GGT | CCA |
| Leu | Gln | Gln | Arg | Ser | Asn | Ser | Gly | Leu | Ala | Thr | Tyr | Ser | Pro | Pro | MET | Gly | Pro |
| Ser | Ser | Arg | Glu | Ala | Ile | Leu | Ala | Trp | Gln | Pro | Ile | Ala | His | Pro | Trp | Val | Gln |
| Pro | Ala | Glu | Lys | Gln | Phe | Trp | Pro | Gly | Asn | Leu | . | Pro | Thr | His | Gly | Ser | Ser |
| | | | | | | | | 405 | | | | | | | | | 432 |
| GTC | AGT | GAA | CGT | AAG | GGT | TCT | ATG | ATT | TCA | GTG | ATG | TCT | TCA | GAG | GGA | AAC | GCA |
| Val | Ser | Glu | Arg | Lys | Gly | Ser | MET | Ile | Ser | Val | MET | Ser | Ser | Glu | Gly | Asn | Ala |
| Ser | Val | Asn | Val | Arg | Val | Leu | . | Phe | Gln | . | Cys | Leu | Gln | Arg | Glu | Thr | Gln |
| Gln | . | Thr | . | Gly | Phe | Tyr | Asp | Phe | Ser | Asp | Val | Phe | Arg | Gly | Lys | Arg | Arg |
| | | | | | | | | 459 | | | | | | | | | 486 |
| GAT | ACA | CCT | GTC | AGC | AAA | TTT | ATG | GAT | CGG | CTG | TTG | TCC | TTA | ATG | GTG | TGT | AAC |
| Asp | Thr | Pro | Val | Ser | Lys | Phe | MET | Asp | Arg | Leu | Leu | Ser | Leu | MET | Val | Cys | Asn |
| Ile | His | Leu | Ser | Ala | Asn | Leu | Trp | Ile | Gly | Cys | Cys | Pro | . | Trp | Cys | Val | Thr |
| Tyr | Thr | Cys | Gln | Gln | Ile | Tyr | Gly | Ser | Ala | Val | Val | Leu | Asn | Gly | Val | . | Pro |

TABLE 2-continued

| | | | | | | | | | | | | | | | | | |
|---|---|---|---|---|---|---|---|---|---|---|---|---|---|---|---|---|---|
| | | | | | | | | 513 | | | | | | | | | 540 |
| CAT | GAG | AA | GTG | GGA | CTT | CAA | ATA | CGG | ACC | AAT | GTT | AAG | GAT | CTG | GTG | GGT | CTA |
| His | Glu | Lys | Val | Gly | Leu | Gln | Ile | Arg | Thr | Asn | Val | Lys | Asp | Leu | Val | Gly | Leu |
| MET | Arg | Lys | Trp | Asp | Phe | Lys | Tyr | Gly | Pro | MET | Leu | Arg | Ile | Trp | Trp | Val | . |
| . | Glu | Ser | Gly | Thr | Ser | Asn | Thr | Asp | Gln | Cys | . | Gly | Ser | Gly | Gly | Ser | Arg |
| | | | | | | | | 567 | | | | | | | | | 594 |
| GAA | TTG | AGT | CVCT | GCT | CTG | TAT | CCA | ATG | CTA | TTT | AAC | AAA | TTG | AAG | AAT | ACC | ATC |
| Glu | Leu | Ser | Pro | Ala | Leu | Tyr | Pro | MET | Leu | Phe | Asn | Lys | Leu | Lys | Asn | Thr | Ile |
| Asn | . | Val | Leu | Leu | Cys | Ile | Gln | Cys | Tyr | Leu | Thr | Asn | . | Arg | Ile | Pro | Ser |
| Ile | Glu | Ser | Cys | Ser | Val | Ser | Asn | Ala | Ile | . | Gln | Ile | Glu | Glu | Tyr | His | Gln |
| | | | | | | | | 621 | | | | | | | | | 648 |
| AGC | AAG | TTT | TTT | GAC | TCC | CAA | GGA | CAG | GTT | TTA | TTG | ACT | GAT | ACC | AAT | ACT | CAA |
| Ser | Lys | Phe | Phe | Asp | Ser | Gln | Gly | Gln | Val | Leu | Leu | Thr | Asp | Thr | Asn | Thr | Gln |
| Ala | Ser | Phe | Leu | Thr | Pro | Lys | Asp | Arg | Phe | Tyr | . | Leu | Ile | Pro | Ile | Leu | Asn |
| Gln | Val | Phe | . | Leu | Pro | Arg | Thr | Gly | Phe | Ile | Asp | . | Tyr | Gln | Tyr | Ser | Ile |
| | | | | | | | | 675 | | | | | | | | | 702 |
| TTT | GTA | GAA | CAA | ACC | ATA | GCT | ATA | ATG | AAG | AAC | TTG | CTA | GAT | AAT | CAT | ACT | GAA |
| Phe | Val | Glu | Gln | Thr | Ile | Ala | Ile | MET | Lys | Asn | Leu | Leu | Asp | Asn | His | Thr | Glu |
| Leu | . | Asn | Lys | Pro | . | Leu | . | . | Arg | Thr | Cys | . | Ile | Ile | Ile | Leu | Lys |
| Cys | Arg | Thr | Asn | His | Ser | Tyr | Asn | Glu | Glu | Leu | Ala | Arg | . | Ser | Tyr | . | Arg |
| | | | | | | | | 729 | | | | | | | | | 756 |
| GGC | AGC | TCT | GAA | CAT | CTA | GGG | CAA | GCT | AGC | ATT | GAA | ACA | ATG | ATG | TTA | AAT | CTG |
| Gly | Ser | Ser | Glu | His | Leu | Gly | Gln | Ala | Ser | Ile | Glu | Thr | MET | MET | Leu | Asn | Leu |
| Ala | Ala | Leu | Asn | Ile | . | Gly | Lys | Leu | Ala | Leu | Lys | Gln | . | Cys | . | Ile | Trp |
| Gln | Leu | . | Thr | Ser | Arg | Ala | Ser | . | His | . | Asn | Asn | Asp | Val | Lys | Ser | Gly |
| | | | | | | | | 783 | | | | | | | | | 810 |
| GTC | AGG | TAT | GTT | CGT | GTG | CTT | GGG | AAT | ATG | GTC | CAT | GCA | ATT | CAA | ATA | AAA | ACG |
| Val | Arg | Tyr | Val | Arg | Val | Leu | Gly | Asn | MET | Val | His | Ala | Ile | Gln | Ile | Lys | Thr |
| Ser | Gly | MET | Phe | Val | Cys | Leu | Gly | Ile | Trp | Ser | MET | Gln | Phe | Lys | . | Lys | Arg |
| Gln | Val | Cys | Ser | Cys | Ala | Trp | Glu | Tyr | Gly | Pro | Cys | Asn | Ser | Asn | Lys | Asn | Glu |
| | | | | | | | | 837 | | | | | | | | | 864 |
| AAA | CTG | TGT | CAA | TTA | GTT | GAA | GTA | ATG | ATG | GCA | AGG | AGA | GAT | GAC | CTC | TCA | TTT |
| Lys | Leu | Cys | Gln | Leu | Val | Glu | Val | MET | MET | Ala | Arg | Arg | Asp | Asp | Leu | Ser | Phe |
| Asn | Cys | Val | Asn | . | Leu | Lys | . | . | Trp | Gln | Gly | Glu | MET | Thr | Ser | His | Phe |
| Thr | Val | Ser | Ile | Ser | . | Ser | Asn | Asp | Gly | Lys | Glu | Arg | . | Pro | Leu | Ile | Leu |
| | | | | | | | | 891 | | | | | | | | | 918 |
| TGC | CAA | GAG | ATG | AAA | TTT | AGG | AAT | AAG | ATG | GTA | GAA | TAC | CTG | ACA | GAC | TGG | GTT |
| Cys | Gln | Glu | MET | Lys | Phe | Arg | Asn | Lys | MET | Val | Glu | Tyr | Leu | Thr | Asp | Trp | Val |
| Ala | Lys | Arg | . | Asn | Leu | Gly | Ile | Arg | Trp | . | Asn | Thr | . | Gln | Thr | Gly | Leu |
| Pro | Arg | Asp | Glu | Ile | . | Glu | . | Asp | Gly | Arg | Ile | Pro | Asp | Arg | Leu | Gly | Tyr |
| | | | | | | | | 945 | | | | | | | | | 972 |
| ATG | GGA | ACA | TCA | AAC | CAA | GCA | GCA | GAT | GAT | GAT | GTA | AAA | TGT | CTT | ACA | AGA | GAT |
| MET | Gly | Thr | Ser | Asn | Gln | Ala | Ala | Asp | Asp | Asp | Val | Lys | Cys | Leu | Thr | Arg | Asp |
| Trp | Glu | His | Gln | Thr | Lys | Gln | Gln | MET | MET | MET | . | Asn | Val | Leu | Gln | Glu | Ile |

TABLE 2-continued

| Gly | Asn | Ile | Lys | Pro | Ser | Ser | Arg | . | . | Cys | Lys | MET | Ser | Tyr | Lys | Arg | Phe |
|---|---|---|---|---|---|---|---|---|---|---|---|---|---|---|---|---|---|
| TTG<br>Leu<br>Trp<br>Gly | GAC<br>Asp<br>Thr<br>Pro | CAG<br>Gln<br>Arg<br>Gly | GCA<br>Ala<br>Gln<br>Lys | AGC<br>Ser<br>Ala<br>His | ATG<br>MET<br>Trp<br>Gly | GAA<br>Glu<br>Lys<br>Ser | GCA<br>Ala<br>Gln<br>Ser | 999<br>GTA<br>Val<br>.<br>Ser | GTT<br>Val<br>Phe<br>Phe | TCA<br>Ser<br>His<br>Thr | CTT<br>Leu<br>Phe<br>Ser | CTA<br>Leu<br>.<br>Ser | GCT<br>Ala<br>Leu<br>Trp | GGT<br>Gly<br>Val<br>Ser | CTC<br>Leu<br>Ser<br>Pro | CCT<br>Pro<br>Leu<br>Ser | 1026<br>CTG<br>Leu<br>Cys<br>Ala |
| CAG<br>Gln<br>Ser<br>Ala | CCT<br>Pro<br>Leu<br>. | GAA<br>Glu<br>Lys<br>Arg | GAA<br>Glu<br>Lys<br>Arg | GGA<br>Gly<br>Glu<br>Arg | GAT<br>Asp<br>MET<br>Trp | GGT<br>Gly<br>Val<br>Cys | GTG<br>Val<br>Trp<br>Gly | 1053<br>GAA<br>Glu<br>Asn<br>Ile | TTG<br>Leu<br>.<br>Asp | ATG<br>MET<br>Trp<br>Gly | GAA<br>Glu<br>Lys<br>Ser | GCC<br>Ala<br>Pro<br>Gln | AAA<br>Lys<br>Asn<br>Ile | TCA<br>Ser<br>His<br>Thr | CAG<br>Gln<br>Ser<br>Val | TTA<br>Leu<br>Tyr<br>Ile | 1080<br>TTT<br>Phe<br>Phe<br>Ser |
| CTT<br>Leu<br>Leu<br>. | AA<br>Lys<br>Asn<br>Ile | TAC<br>Tyr<br>Thr<br>Leu | TTC<br>Phe<br>Ser<br>His | ACA<br>Thr<br>His<br>Ile | TTA<br>Leu<br>Tyr<br>Ile | TTT<br>Phe<br>Leu<br>Tyr | ATG<br>MET<br>.<br>Glu | 1107<br>AAC<br>Asn<br>Thr<br>Pro | CTT<br>Leu<br>Phe<br>Phe | TTG<br>Leu<br>.<br>Glu . | AAT<br>Asn<br>MET<br>Leu | GAC<br>Asp<br>Thr<br>Gln | TGC<br>Cys<br>Ala<br>. | AGT<br>Ser<br>Val<br>Ser | GAA<br>Glu<br>Lys<br>. | GTT<br>Val<br>Leu<br>Arg | 1134<br>GAA<br>Glu<br>Lys |
| GAT<br>Asp<br>MET<br>. | GAA<br>Glu<br>Lys<br>Lys | AGT<br>Ser<br>Val<br>Cys | GCG<br>Ala<br>Arg<br>Ala | CAA<br>Gln<br>Lys<br>Asn | ACA<br>Thr<br>Gln<br>Arg | GGT<br>Gly<br>Val<br>Trp | GGC<br>Gly<br>Ala<br>Gln | 1161<br>AGG<br>Arg<br>Gly<br>Glu | AAA<br>Lys<br>Asn<br>Thr | CGT<br>Arg<br>Val<br>Trp | GGC<br>Gly<br>Ala<br>His | ATG<br>MET<br>Cys<br>Val | TCT<br>Ser<br>Leu<br>Ser | CGG<br>Arg<br>Gly<br>Glu | AGG<br>Arg<br>Gly<br>Ala | CTG<br>Leu<br>Trp<br>Gly | 1188<br>GCA<br>Ala<br>His<br>Ile |
| TCA<br>Ser<br>His<br>Thr | CTG<br>Leu<br>.<br>Glu | AGG<br>Arg<br>Gly<br>Ala | CAC<br>His<br>Thr<br>Leu | TGT<br>Cys<br>Val<br>Tyr | ACG<br>Thr<br>Arg<br>Gly | GTC<br>Val<br>Ser<br>Pro | CTT<br>Leu<br>Leu<br>Cys | 1215<br>GCA<br>Ala<br>Gln<br>Asn | ATG<br>MET<br>Cys<br>Val | TCA<br>Ser<br>Gln<br>Lys | AAC<br>Asn<br>Thr<br>Leu | TTA<br>Leu<br>Tyr<br>Thr | CTC<br>Leu<br>Ser<br>Gln | AAT<br>Asn<br>MET<br>Cys | GCC<br>Ala<br>Pro<br>Gln | AAC<br>Asn<br>Thr<br>Arg | 1242<br>GTA<br>Val<br>.<br>Arg |
| GAC<br>Asp<br>Thr<br>Gln | AGT<br>Ser<br>Val<br>Trp | GGT<br>Gly<br>Val<br>Ser | CTC<br>Leu<br>Ser<br>His | ATG<br>MET<br>Cys<br>Ala | CAC<br>His<br>Thr<br>Leu | TCC<br>Ser<br>Pro<br>His | ATA<br>Ile<br>.<br>Arg | 1269<br>GGC<br>Gly<br>Ala<br>Leu | TTA<br>Leu<br>.<br>Arg | GGT<br>Gly<br>Val<br>Leu | TAC<br>Tyr<br>Thr<br>Pro | CAC<br>His<br>Thr<br>Gln | AAG<br>Lys<br>Arg<br>Gly | GAT<br>Asp<br>Ile<br>Ser | CTC<br>Leu<br>Ser<br>Pro | CAG<br>Gln<br>Arg<br>Asp | 1296<br>ACA<br>Thr<br>Gln<br>Lys |
| AGA<br>Arg<br>Glu<br>Ser | GCT<br>Ala<br>Leu<br>Tyr | ACA<br>Thr<br>His<br>Ile | TTT<br>Phe<br>Leu<br>Tyr | ATG<br>MET<br>Trp<br>Gly | GAA<br>Glu<br>Lys<br>Ser | GTT<br>Val<br>Phe<br>Ser | CTC<br>Leu<br>Ser<br>His | 1323<br>ACA<br>Thr<br>Gln<br>Lys | AAA<br>Lys<br>Lys<br>Asn | ATC<br>Ile<br>Ser<br>Pro | CTT<br>Leu<br>Phe<br>Ser | CAA<br>Gln<br>Asn<br>Thr | CAA<br>Gln<br>Lys<br>Arg | GGC<br>Gly<br>Ala<br>His | ACA<br>Thr<br>Gln<br>Arg | GAA<br>Glu<br>Asn<br>Ile | 1350<br>TTT<br>Phe<br>Leu<br>. |
| GAC<br>Asp<br>Thr<br>His | ACA<br>Thr<br>His<br>Thr | CTT<br>Leu<br>Leu<br>Cys | GCA<br>Ala<br>Gln<br>Arg | GAA<br>Glu<br>Lys<br>Asn | ACA<br>Thr<br>Gln<br>Ser | GTA<br>Val<br>Tyr<br>Ile | TTG<br>Leu<br>Trp<br>Gly | 1377<br>GCT<br>Ala<br>Leu<br>. | GAT<br>Asp<br>Ile<br>Ser | CGG<br>Arg<br>Gly<br>Val | TTT<br>Phe<br>Leu<br>. | GAG<br>Glu<br>Arg<br>Glu | AGA<br>Arg<br>Asp<br>Ile | TTG<br>Leu<br>Trp<br>Gly | GTG<br>Val<br>Trp<br>Gly | GAA<br>Glu<br>Asn<br>Thr | 1404<br>CTG<br>Leu<br>Trp<br>Gly |
| GTC<br>Val | ACA<br>Thr | ATG<br>MET | ATG<br>MET | GGT<br>Gly | GAT<br>Asp | CAA<br>Gln | GGA<br>Gly | 1431<br>GAA<br>Glu | CTC<br>Leu | CCT<br>Pro | ATA<br>Ile | GCG<br>Ala | ATG<br>MET | GCT<br>Ala | CTG<br>Leu | GCC<br>Ala | 1458<br>AAT<br>Asn |

TABLE 2-continued

| | | | | | | | | | | | | | | | | | |
|---|---|---|---|---|---|---|---|---|---|---|---|---|---|---|---|---|---|
| Ser | Gln | . | Trp | Val | Ile | Lys | Glu | Asn | Ser | Leu | . | Arg | Trp | Leu | Trp | Pro | MET |
| His | Asn | Asp | Gly | . | Ser | Arg | Arg | Thr | Pro | Tyr | Ser | Asp | Gly | Ser | Gly | Gln | Cys |
| | | | | | | | | 1485 | | | | | | | | | 1512 |
| GTG | GTT | CCT | TGT | TCT | CAG | TGG | GAT | GAA | CTA | GCT | CGA | GTT | CTG | GTT | ACT | CTG | TTT |
| Val | Val | Pro | Cys | Ser | Gln | Trp | Asp | Glu | Leu | Ala | Arg | Val | Leu | Val | Thr | Leu | Phe |
| Trp | Phe | Leu | Val | Leu | Ser | Gly | MET | Asn | . | Leu | Glu | Phe | Trp | Leu | Leu | Cys | Leu |
| Gly | Ser | Leu | Phe | Ser | Val | Gly | . | Thr | Ser | Ser | Ser | Ser | Gly | Tyr | Ser | Val | . |
| | | | | | | | | 1539 | | | | | | | | | 1566 |
| GAT | TCT | CGG | CAT | TTA | CTC | TAC | CAA | CTG | CTC | TGG | AAC | ATG | TTT | TCT | AAA | GAA | GTA |
| Asp | Ser | Arg | His | Leu | Leu | Tyr | Gln | Leu | Leu | Trp | Asn | MET | Phe | Ser | Lys | Glu | Val |
| Ile | Leu | Gly | Ile | Tyr | Ser | Thr | Asn | Cys | Ser | Gly | Thr | Cys | Phe | Leu | Lys | Lys | . |
| Phe | Ser | Ala | Phe | Thr | Leu | Pro | Thr | Ala | Leu | Glu | His | Val | Phe | . | Arg | Ser | Arg |
| | | | | | | | | 1593 | | | | | | | | | 1620 |
| GAA | TTG | GCA | GAC | TCC | ATG | CAG | ACT | CTC | TTC | CGA | GGC | AAC | AGC | TTG | GCC | AGT | AAA |
| Glu | Leu | Ala | Asp | Ser | MET | Gln | Thr | Leu | Phe | Arg | Gly | Asn | Ser | Leu | Ala | Ser | Lys |
| Asn | Trp | Gln | Thr | Pro | Cys | Arg | Leu | Ser | Ser | Glu | Ala | Thr | Ala | Trp | Pro | Val | Lys |
| Ile | Gly | Arg | Leu | His | Ala | Asp | Ser | Leu | Pro | Arg | Gln | Gln | Leu | Gly | Gln | . | Asn |
| | | | | | | | | 1647 | | | | | | | | | 1674 |
| ATA | ATG | ACA | TTC | TGT | TTC | AAG | GTA | TAT | GGT | GCT | ACC | TAT | CTA | CAA | AAA | CTC | CTG |
| Ile | MET | Thr | Phe | Cys | Phe | Lys | Val | Tyr | Gly | Ala | Thr | Tyr | Leu | Gln | Lys | Leu | Leu |
| . | . | His | Ser | Val | Ser | Arg | Tyr | MET | Val | Leu | Pro | Ile | Tyr | Lys | Asn | Ser | Trp |
| Asn | Asp | Ile | Leu | Phe | Gln | Gly | Ile | Trp | Cys | Tyr | Leu | Ser | Thr | Lys | Thr | Pro | Gly |
| | | | | | | | | 1701 | | | | | | | | | 1728 |
| GAT | CCT | TTA | TTA | CGA | ATT | GTG | ATC | ACA | TCC | TCT | GAT | TGG | CAA | CAT | GTT | AGC | TTT |
| Asp | Pro | Leu | Leu | Arg | Ile | Val | Ile | Thr | Ser | Ser | Asp | Trp | Gln | His | Val | Ser | Phe |
| Ile | Leu | Tyr | Tyr | Glu | Leu | . | Ser | His | Pro | Leu | Ile | Gly | Asn | MET | Leu | Ala | Leu |
| Ser | Phe | Ile | Thr | Asn | Cys | Asp | His | Ile | Leu | . | Leu | Ala | Thr | Cys | . | Leu | . |
| | | | | | | | | 1755 | | | | | | | | | 1782 |
| GAA | GTG | GAT | CCT | ACC | AGG | TTA | GAA | CCA | TCA | GAG | AGC | CTT | GAG | GAA | AAC | CAG | CGG |
| Glu | Val | Asp | Pro | Thr | Arg | Leu | Glu | Pro | Ser | Glu | Ser | Leu | Glu | Glu | Asn | Gln | Arg |
| Lys | Trp | Ile | Leu | Pro | Gly | . | Asn | His | Gln | Arg | Ala | Leu | Arg | Lys | Thr | Ser | Gly |
| Ser | Gly | Ser | Tyr | Gln | Val | Arg | Thr | Ile | Arg | Glu | Pro | . | Gly | Lys | Pro | Ala | Glu |
| | | | | | | | | 1809 | | | | | | | | | 1836 |
| AAC | CTC | CTT | CAG | ATG | ACT | GAA | AAG | TTC | TTC | CAT | GCC | ATC | ATC | AGT | TCC | TCC | TCA |
| Asn | Leu | Leu | Gln | MET | Thr | Glu | Lys | Phe | Phe | His | Ala | Ile | Ile | Ser | Ser | Ser | Ser |
| Thr | Ser | Phe | Arg | . | Leu | Lys | Ser | Ser | Ser | MET | Pro | Ser | Ser | Val | Pro | Pro | Gln |
| Pro | Pro | Ser | Asp | Asp | . | Lys | Val | Leu | Pro | Cys | His | His | Gln | Phe | Leu | Leu | Arg |
| | | | | | | | | 1863 | | | | | | | | | 1890 |
| GAA | TTC | CCC | CCT | CAA | CTT | CGA | AGT | GTG | TGC | CAC | TGT | TTA | TAC | CAG | GTG | GTT | AGC |
| Glu | Phe | Pro | Pro | Gln | Leu | Arg | Ser | Val | Cys | His | Cys | Leu | Tyr | Gln | Val | Val | Ser |
| Asn | Ser | Pro | Leu | Asn | Phe | Glu | Val | Cys | Ala | Thr | Val | Tyr | Thr | Arg | Trp | Leu | Ala |
| Ile | Pro | Pro | Ser | Thr | Ser | Lys | Cys | Val | Pro | Leu | Phe | Ile | Pro | Gly | Gly | . | Pro |
| | | | | | | | | 1917 | | | | | | | | | 1944 |
| CAG | CGT | TTC | CCT | CAG | AAC | AGC | ATC | GGT | GCA | GTA | GGA | AGT | GCC | ATG | TTC | CTC | AGA |

TABLE 2-continued

| | | | | | | | | | | | | | | | | | |
|---|---|---|---|---|---|---|---|---|---|---|---|---|---|---|---|---|---|
| Gln | Arg | Phe | Pro | Gln | Asn | Ser | Ile | Gly | Ala | Val | Gly | Ser | Ala | MET | Phe | Leu | Arg |
| Ser | Val | Ser | Leu | Arg | Thr | Ala | Ser | Val | Gln | . | Glu | Val | Pro | Cys | Ser | Ser | Asp |
| Ala | Phe | Pro | Ser | Glu | Gln | His | Arg | Cys | Ser | Arg | Lys | Cys | His | Val | Pro | Gln | Ile |
| | | | | | | | | 1971 | | | | | | | | | 1998 |
| TTT | ATC | AAT | CCT | GCC | ATT | GTC | TCA | CCG | TAT | GAA | GCA | GGG | ATT | TTA | GAT | AAA | AAG |
| Phe | Ile | Asn | Pro | Ala | Ile | Val | Ser | Pro | Tyr | Glu | Ala | Gly | Ile | Leu | Asp | Lys | Lys |
| Leu | Ser | Ile | Leu | Pro | Leu | Ser | His | Arg | MET | Lys | Gln | Gly | Phe | . | Ile | Lys | Ser |
| Tyr | Gln | Ser | Cys | His | Cys | Leu | Thr | Val | . | Ser | Arg | Asp | Phe | Arg | . | Lys | Ala |
| | | | | | | | | 2025 | | | | | | | | | 2052 |
| CCA | CCA | CCT | AGA | ATC | GAA | AGG | GGC | TTG | AAG | TTA | ATG | TCA | AAG | ATA | CTT | CAG | AGT |
| Pro | Pro | Pro | Arg | Ile | Glu | Arg | Gly | Leu | Lys | Leu | MET | Ser | Lys | Ile | Leu | Gln | Ser |
| His | His | Leu | Glu | Ser | Lys | Gly | Ala | . | Ser | . | Cys | Gln | Arg | Tyr | Phe | Arg | Val |
| Thr | Thr | . | Asn | Arg | Lys | Gly | Leu | Glu | Val | Asn | Val | Lys | Asp | Thr | Ser | Glu | Tyr |
| | | | | | | | | 2079 | | | | | | | | | 2106 |
| ATT | GCC | AAT | CAT | GTT | CTC | TTC | ACA | AAA | GAA | GAA | CAT | ATG | CGG | CCT | TTC | AAT | GAT |
| Ile | Ala | Asn | His | Val | Leu | Phe | Thr | Lys | Glu | Glu | His | MET | Arg | Pro | Phe | Asn | Asp |
| Leu | Pro | Ile | MET | Phe | Ser | Ser | Gln | Lys | Lys | Asn | Ile | Cys | Gly | Leu | Ser | MET | Ile |
| Cys | Gln | Ser | Cys | Ser | Leu | His | Lys | Arg | Arg | Thr | Tyr | Ala | Ala | Phe | Gln | . | Phe |
| | | | | | | | | 2133 | | | | | | | | | 2160 |
| TTT | GTG | AAA | AGC | AAC | TTT | GAT | GCA | GCA | CGC | AGG | TTT | TTC | CTT | GAT | ATA | GCA | TCT |
| Phe | Val | Lys | Ser | Asn | Phe | Asp | Ala | Ala | Arg | Arg | Phe | Phe | Leu | Asp | Ile | Ala | Ser |
| Leu | . | Lys | Ala | Thr | Leu | MET | Gln | His | Ala | Gly | Phe | Ser | Leu | Ile | . | His | Leu |
| Cys | Glu | Lys | Gln | Leu | . | Cys | Ser | Thr | Gln | Val | Phe | Pro | . | Tyr | Ser | Ile | . |
| | | | | | | | | 2187 | | | | | | | | | 2214 |
| GAT | TGT | CCT | ACA | AGT | GAT | GCA | GTA | AAT | CAT | AGT | CTT | TCC | TTC | ATA | AGT | GAC | GGC |
| Asp | Cys | Pro | Thr | Ser | Asp | Ala | Val | Asn | His | Ser | Leu | Ser | Phe | Ile | Ser | Asp | Gly |
| Ile | Val | Leu | Gln | Val | MET | Gln | . | Ile | Ile | Val | Phe | Pro | Ser | . | Val | Thr | Ala |
| Leu | Ser | Tyr | Lys | . | Cys | Ser | Lys | Ser | . | Ser | Phe | Leu | His | Lys | . | Arg | Gln |
| | | | | | | | | 2241 | | | | | | | | | 2268 |
| AAT | GTG | CTT | GCT | TTA | CAT | CGT | CTA | CTC | TGG | AAC | AAT | CAG | GAG | AAA | ATT | GGG | CAG |
| Asn | Val | Leu | Ala | Leu | His | Arg | Leu | Leu | Trp | Asn | Asn | Gln | Glu | Lys | Ile | Gly | Gln |
| MET | Cys | Leu | Leu | Tyr | Ile | Val | Tyr | Ser | Gly | Thr | Ile | Arg | Arg | Lys | Leu | Gly | Ser |
| Cys | Ala | Cys | Phe | Thr | Ser | Ser | Thr | Leu | Glu | Gln | Ser | Gly | Glu | Asn | Trp | Ala | Val |
| | | | | | | | | 2295 | | | | | | | | | 2322 |
| TAT | CTT | TCC | AGC | AAC | AGG | GAT | CAT | AAA | GCT | GTT | GGA | AGA | CGA | CCT | TTT | GAT | AAG |
| Tyr | Leu | Ser | Ser | Asn | Arg | Asp | His | Lys | Ala | Val | Gly | Arg | Arg | Pro | Phe | Asp | Lys |
| Ile | Phe | Pro | Ala | Thr | Gly | Ile | Ile | Lys | Leu | Leu | Glu | Asp | Asp | Leu | Leu | Ile | Arg |
| Ser | Phe | Gln | Gln | Gln | Gly | Ser | . | Ser | Cys | Trp | Lys | Thr | Thr | Phe | . | . | Asp |
| | | | | | | | | 2349 | | | | | | | | | 2376 |
| ATG | GCA | ACA | CTT | CTT | GCA | TAC | CTG | GGT | CCT | CCA | GAG | CAC | AAA | CCT | GTG | GCA | GAT |
| MET | Ala | Thr | Leu | Leu | Ala | Tyr | Leu | Gly | Pro | Pro | Glu | His | Lys | Pro | Val | Ala | Asp |
| Trp | Gln | His | Phe | Leu | His | Thr | Trp | Val | Leu | Gln | Ser | Thr | Asn | Leu | Trp | Gln | Ile |
| Gly | Asn | Thr | Ser | Cys | Ile | Pro | Gly | Ser | Ser | Arg | Ala | Gln | Thr | Cys | Gly | Arg | Tyr |
| | | | | | | | | 2403 | | | | | | | | | 2430 |
| ACA | CAC | TGG | TCC | AGC | CTT | AAC | CTT | ACC | AGT | TCA | AAG | TTT | GAG | GAA | TTT | ATG | ACT |

TABLE 2-continued

| | | | | | | | | | | | | | | | | | |
|---|---|---|---|---|---|---|---|---|---|---|---|---|---|---|---|---|---|
| Thr | His | Trp | Ser | Ser | Leu | Asn | Leu | Thr | Ser | Ser | Lys | Phe | Glu | Glu | Phe | MET | Thr |
| His | Thr | Gly | Pro | Ala | Leu | Thr | Leu | Pro | Val | Gln | Ser | Leu | Arg | Asn | Leu | . | Leu |
| Thr | Leu | Val | Gln | Pro | . | Pro | Tyr | Gln | Phe | Lys | Val | . | Gly | Ile | Tyr | Asp | . |
| | | | | | | | | 2457 | | | | | | | | | 2484 |
| AGG | CAT | CAT | CAG | GTA | CAT | GAA | AAA | GAA | GAA | TTC | AAG | GCT | TTG | AAA | ACG | TTA | AGT |
| Arg | His | His | Gln | Val | His | Glu | Lys | Glu | Glu | Phe | Lys | Ala | Leu | Lys | Thr | Leu | Ser |
| Gly | Ile | Ile | Arg | Tyr | MET | Lys | Lys | Lys | Asn | Ser | Arg | Leu | . | Lys | Arg | . | Val |
| Ala | Ser | Ser | Gly | Thr | . | Lys | Arg | Arg | Ile | Gln | Gly | Phe | Glu | Asn | Val | Lys | Tyr |
| | | | | | | | | 2511 | | | | | | | | | 2538 |
| ATT | TTC | TAC | CAA | GCT | GGG | ACT | TCC | AAA | GCT | GGG | AAT | CCT | ATT | TTT | TAT | TAT | GTT |
| Ile | Phe | Tyr | Gln | Ala | Gly | Thr | Ser | Lys | Ala | Gly | Asn | Pro | Ile | Phe | Tyr | Tyr | Val |
| Phe | Ser | Thr | Lys | Leu | Gly | Leu | Pro | Lys | Leu | Gly | Ile | Leu | Phe | Phe | Ile | MET | Leu |
| Phe | Leu | Pro | Ser | Trp | Asp | Phe | Gln | Ser | Trp | Glu | Ser | Tyr | Phe | Leu | Leu | Cys | Cys |
| | | | | | | | | 2565 | | | | | | | | | 2592 |
| GCA | CGG | AGG | TTC | AAA | ACT | GGT | CAA | ATC | AAT | GGT | GAT | TTG | CTG | ATA | TAC | CAT | GTC |
| Ala | Arg | Arg | Phe | Lys | Thr | Gly | Gln | Ile | Asn | Gly | Asp | Leu | Leu | Ile | Tyr | His | Val |
| His | Gly | Gly | Ser | Lys | Leu | Val | Lys | Ser | MET | Val | Ile | Cys | . | Tyr | Thr | MET | Ser |
| Thr | Glu | Val | Gln | Asn | Trp | Ser | Asn | Gln | Trp | . | Phe | Ala | Asp | Ile | Pro | Cys | Leu |
| | | | | | | | | 2619 | | | | | | | | | 2646 |
| TTA | CTG | ACT | TTA | AAG | CCA | TAT | TAT | GCA | AAG | CCA | TAT | GAA | ATT | GTA | GTG | GAC | CTT |
| Leu | Leu | Thr | Leu | Lys | Pro | Tyr | Tyr | Ala | Lys | Pro | Tyr | Glu | Ile | Val | Val | Asp | Leu |
| Tyr | . | Leu | . | Ser | His | Ile | MET | Gln | Ser | His | MET | Lys | Leu | . | Trp | Thr | Leu |
| Thr | Asp | Phe | Lys | Ala | Ile | Leu | Cys | Lys | Ala | Ile | . | Asn | Cys | Ser | Gly | Pro | Tyr |
| | | | | | | | | 2673 | | | | | | | | | 2700 |
| ACC | CAT | ACC | GGG | CCT | AGC | AAT | CGC | TTT | AAA | ACA | GAC | TTT | CTC | TCT | AAG | TGG | TTT |
| Thr | His | Thr | Gly | Pro | Ser | Asn | Arg | Phe | Lys | Thr | Asp | Phe | Leu | Ser | Lys | Trp | Phe |
| Pro | Ile | Pro | Gly | Leu | Ala | Ile | Ala | Leu | Lys | Gln | Thr | Phe | Ser | Leu | Ser | Gly | Leu |
| Pro | Tyr | Arg | Ala | . | Gln | Ser | Leu | . | Asn | Arg | Leu | Ser | Leu | . | Val | Val | Cys |
| | | | | | | | | 2727 | | | | | | | | | 2754 |
| GTT | GTT | TTT | CCT | GGC | TTT | GCT | TAC | GAC | AAC | GTC | TCC | GCA | GTC | TAT | ATC | TAT | AAC |
| Val | Val | Phe | Pro | Gly | Phe | Ala | Tyr | Asp | Asn | Val | Ser | Ala | Val | Tyr | Ile | Tyr | Asn |
| Leu | Phe | Phe | Leu | Ala | Leu | Leu | Thr | Thr | Thr | Ser | Pro | Gln | Ser | Ile | Ser | Ile | Thr |
| Cys | Phe | Ser | Trp | Leu | Cys | Leu | Arg | Gln | Arg | Leu | Arg | Ser | Leu | Tyr | Leu | . | Leu |
| | | | | | | | | 2781 | | | | | | | | | 2808 |
| TGT | AAC | TCC | TGG | GTC | AGG | GAG | TAC | ACC | AAG | TAT | CAT | GAG | CGG | CTG | CTG | ACT | GGC |
| Cys | Asn | Ser | Trp | Val | Arg | Glu | Tyr | Thr | Lys | Tyr | His | Glu | Arg | Leu | Leu | Thr | Gly |
| Val | Thr | Pro | Gly | Ser | Gly | Ser | Thr | Pro | Ser | Ile | MET | Ser | Gly | Cys | . | Leu | Ala |
| . | Leu | Leu | Gly | Gln | Gly | Val | His | Gln | Val | Ser | . | Ala | Ala | Ala | Asp | Trp | Pro |
| | | | | | | | | 2835 | | | | | | | | | 2862 |
| CTC | AAA | GGT | AGC | AAA | AGG | CTT | GTT | TTC | ATA | GAC | TGT | CCT | GGG | AAA | CTG | GCT | GAG |
| Leu | Lys | Gly | Ser | Lys | Arg | Leu | Val | Phe | Ile | Asp | Cys | Pro | Gly | Lys | Leu | Ala | Glu |
| Ser | Lys | Val | Ala | Lys | Gly | Leu | Phe | Ser | . | Thr | Val | Leu | Gly | Asn | Trp | Leu | Ser |
| Gln | Arg | . | Gln | Lys | Ala | Cys | Phe | His | Arg | Leu | Ser | Trp | Glu | Thr | Gly | . | Ala |
| | | | | | | | | 2889 | | | | | | | | | 2916 |

TABLE 2-continued

| | | | | | | | | | | | | | | | | | |
|---|---|---|---|---|---|---|---|---|---|---|---|---|---|---|---|---|---|
| CAC | ATA | GAG | CAT | GAA | CAA | CAG | AAA | CTA | CCT | GCT | GCC | ACC | TTG | GCT | TTA | GAA | GAG |
| His | Ile | Glu | His | Glu | Gln | Gln | Lys | Leu | Pro | Ala | Ala | Thr | Leu | Ala | Leu | Glu | Glu |
| Thr | . | Ser | MET | Asn | Asn | Arg | Asn | Tyr | Leu | Leu | Pro | Pro | Trp | Leu | . | Lys | Arg |
| His | Arg | Ala | . | Thr | Thr | Glu | Thr | Thr | Cys | Cys | His | Leu | Gly | Phe | Arg | Arg | Gly |
| | | | | | | | | 2943 | | | | | | | | | 2970 |
| GAC | CTG | AAG | GTA | TTC | CAC | AAT | GCT | CTC | AAG | CTA | GCT | CAC | AAA | GAC | ACC | AAA | GTT |
| Asp | Leu | Lys | Val | Phe | His | Asn | Ala | Leu | Lys | Leu | Ala | His | Lys | Asp | Thr | Lys | Val |
| Thr | . | Arg | Tyr | Ser | Thr | MET | Leu | Ser | Ser | . | Leu | Thr | Lys | Thr | Pro | Lys | Phe |
| Pro | Glu | Gly | Ile | Pro | Gln | Cys | Ser | Gln | Ala | Ser | Ser | Gln | Arg | His | Gln | Ser | Phe |
| | | | | | | | | 2997 | | | | | | | | | 3024 |
| TCT | ATT | AAA | GTT | GGT | TCT | ACT | GCT | GTC | CAA | GTA | ACT | TCA | GCA | GAG | CGA | ACA | AAA |
| Ser | Ile | Lys | Val | Gly | Ser | Thr | Ala | Val | Gln | Val | Thr | Ser | Ala | Glu | Arg | Thr | Lys |
| Leu | Leu | Lys | Leu | Val | Leu | Leu | Leu | Ser | Lys | . | Leu | Gln | Gln | Ser | Glu | Gln | Lys |
| Tyr | . | Ser | Trp | Phe | Tyr | Cys | Cys | Pro | Ser | Asn | Phe | Ser | Arg | Ala | Asn | Lys | Ser |
| | | | | | | | | 3051 | | | | | | | | | 3078 |
| GTC | CTA | GGG | CAA | TCA | GTC | TTT | CTA | AAT | GAC | ATT | TAT | TAT | GCT | TCG | GAA | ATT | GAA |
| Val | Leu | Gly | Gln | Ser | Val | Phe | Leu | Asn | Asp | Ile | Tyr | Tyr | Ala | Ser | Glu | Ile | Glu |
| Ser | . | Gly | Asn | Gln | Ser | Phe | . | MET | Thr | Phe | Ile | MET | Leu | ASrg | Lys | Leu | Lys |
| Pro | Arg | Ala | Ile | Ser | Leu | Ser | Lys | . | His | Leu | Leu | Cys | Phe | Gly | Asn | . | Arg |
| | | | | | | | | 3105 | | | | | | | | | 3132 |
| GAA | ATC | TGC | CTA | GTA | GAT | GAG | AAC | CAG | TTC | ACC | TTA | ACC | ATT | GCA | AAC | CAG | GGC |
| Glu | Ile | Cys | Leu | Val | Asp | Glu | Asn | Gln | Phe | Thr | Leu | Thr | Ile | Ala | Asn | Gln | Gly |
| Lys | Ser | Ala | . | . | MET | Arg | Thr | Ser | Ser | Pro | . | Pro | Leu | Gln | Thr | Arg | Ala |
| Asn | Leu | Pro | Ser | Arg | . | Glu | Pro | Val | His | Leu | Asn | His | Cys | Lys | Pro | Gly | His |
| | | | | | | | | 3159 | | | | | | | | | 3186 |
| ACG | CCG | CTC | ACC | TTC | ATG | CAC | CAG | GAG | TGT | GAA | GCC | ATT | GTC | CAG | TCT | ATC | ATT |
| Thr | Pro | Leu | Thr | Phe | MET | His | Gln | Glu | Cys | Glu | Ala | Ile | Val | Gln | Ser | Ile | Ile |
| Arg | Arg | Ser | Pro | Ser | Cys | Thr | Arg | Ser | Val | Lys | Pro | Leu | Ser | Ser | Leu | Ser | Phe |
| Ala | Ala | His | Leu | His | Ala | Pro | Gly | Val | . | Ser | His | Cys | Pro | Val | Tyr | His | Ser |
| | | | | | | | | 3213 | | | | | | | | | 3240 |
| CAT | ATC | CGG | ACC | CGC | TGG | GAA | CTG | TCA | CAG | CCC | GAC | TCT | ATC | CCC | CAA | CAC | ACC |
| His | Ile | Arg | Thr | Arg | Trp | Glu | Leu | Ser | Gln | Pro | Asp | Ser | Ile | Pro | Gln | His | Thr |
| Ile | Ser | Gly | Pro | Ala | Gly | Asn | Cys | His | Ser | Pro | Thr | Leu | Ser | Pro | Asn | Thr | Pro |
| Tyr | Pro | Asp | Pro | Leu | Gly | Thr | Val | Thr | Ala | Arg | Leu | Tyr | Pro | Pro | Thr | His | Gln |
| | | | | | | | | 3267 | | | | | | | | | 3294 |
| AAG | ATT | CGG | CCA | AA | GAT | GTC | CCT | GGG | ACA | CTG | CTC | AAT | ATC | GCA | TTA | CTT | AAT |
| Lys | Ile | Arg | Pro | Lys | Asp | Val | Pro | Gly | Thr | Leu | Leu | Asn | Ile | Ala | Leu | Leu | Asn |
| Arg | Phe | Gly | Gln | Lys | MET | Ser | Leu | Gly | His | Cys | Ser | Ile | Ser | His | Tyr | Leu | Ile |
| Asp | Ser | Ala | Lys | Arg | Cys | Pro | Trp | Asp | Thr | Ala | Gln | Tyr | Arg | Ile | Thr | . | Phe |
| | | | | | | | | 3321 | | | | | | | | | 3348 |
| TTA | GGC | AGT | TCT | GAC | CCG | AGT | TTA | CGG | TCA | GCT | GCC | TAT | AAT | CTT | CTG | TGT | GCC |
| Leu | Gly | Ser | Ser | Asp | Pro | Ser | Leu | Arg | Ser | Ala | Ala | Tyr | Asn | Leu | Leu | Cys | Ala |
| . | Ala | Val | Leu | Thr | Arg | Val | Tyr | Gly | Gln | Leu | Pro | Ile | Ile | Phe | Cys | Val | Pro |
| Arg | Gln | Phe | . | Pro | Glu | Phe | Thr | Val | Ser | Cys | Leu | . | Ser | Ser | Val | Cys | Leu |

TABLE 2-continued

| | | | | | | | | | | | | | | | | | |
|---|---|---|---|---|---|---|---|---|---|---|---|---|---|---|---|---|---|
| | | | | | | | | 3375 | | | | | | | | | 3402 |
| TTA | ACT | TGT | ACC | TTT | AAT | TTA | AAA | ATC | GAG | GGC | CAG | TTA | CTA | GAG | ACA | TCA | GGT |
| Leu | Thr | Cys | Thr | Phe | Asn | Leu | Lys | Ile | Glu | Gly | Gln | Leu | Leu | Glu | Thr | Ser | Gly |
| . | Leu | Val | Pro | Leu | Ile | . | Lys | Ser | ASrg | Ala | Ser | Tyr | . | Arg | His | Gln | Val |
| Asn | Leu | Tyr | Leu | . | Phe | Lys | Asn | Arg | Gly | Pro | Val | Thr | Arg | Asp | Ile | Arg | Phe |
| | | | | | | | | 3429 | | | | | | | | | 3456 |
| TTA | TGT | ATC | CCT | GCC | AAC | AAC | ACC | CTC | TTT | ATT | GTC | TCT | ATT | AGT | AAG | ACA | CTG |
| Leu | Cys | Ile | Pro | Ala | Asn | Asn | Thr | Leu | Phe | Ile | Val | Ser | Ile | Ser | Lys | Thr | Leu |
| Tyr | Val | Ser | Leu | Pro | Thr | Thr | Pro | Ser | Leu | Leu | Ser | Leu | Leu | Val | Arg | His | Trp |
| MET | Tyr | Pro | Cys | Gln | Gln | His | Pro | Leu | Tyr | Cys | Leu | Tyr | . | . | Asp | Thr | Gly |
| | | | | | | | | 3483 | | | | | | | | | 3510 |
| GCA | GCC | AAT | GAG | CCA | CAC | CTC | ACG | TTA | GAA | TTT | TTG | GAA | GAG | TGT | ATT | TCT | GGA |
| Ala | Ala | Asn | Glu | Pro | His | Leu | Thr | Leu | Glu | Phe | Leu | Glu | Glu | Cys | Ile | Ser | Gly |
| Gln | Pro | MET | Ser | His | Thr | Ser | Arg | . | Asn | Phe | Trp | Lys | Ser | Val | Phe | Leu | Asp |
| Ser | Gln | . | Ala | Thr | Pro | His | Val | Arg | Ile | Phe | Gly | Arg | Val | Tyr | Phe | Trp | Ile |
| | | | | | | | | 3537 | | | | | | | | | 3564 |
| TTT | AGC | AAA | TCT | AGT | ATT | GAA | TTG | AAA | CAC | CTT | TGT | TTG | GAA | TAC | ATG | ACT | CCA |
| Phe | Ser | Lys | Ser | Ser | Ile | Glu | Leu | Lys | His | Leu | Cys | Leu | Glu | Tyr | MET | Thr | Pro |
| Leu | Ala | Asn | Leu | Val | Leu | Asn | . | Asn | Thr | Phe | Val | Trp | Asn | Thr | . | Leu | His |
| . | Gln | Ile | . | Tyr | . | Ile | Glu | Thr | Pro | Leu | Phe | Gly | Ile | His | Asp | Ser | MET |
| | | | | | | | | 3591 | | | | | | | | | 3618 |
| TGG | CTG | TCA | AAT | CTA | GTT | CGT | TTT | TGC | AAG | CAT | AAT | GAT | GAT | GCC | AAA | CGA | CAA |
| Trp | Leu | Ser | Asn | Leu | Val | Arg | Phe | Cys | Lys | His | Asn | Asp | Asp | Ala | Lys | Arg | Gln |
| Gly | Cys | Gln | Ile | . | Phe | Val | Phe | Ala | Ser | Ile | MET | MET | MET | Pro | Asn | Asp | Lys |
| Ala | Val | Lys | Ser | Ser | Ser | Phe | Leu | Gln | Ala | . | . | . | Cys | Gln | Thr | Thr | Lys |
| | | | | | | | | 3645 | | | | | | | | | 3672 |
| AGA | GTT | ACT | GCT | ATT | CTT | GAC | AAG | CTG | ATA | ACA | ATG | ACC | ATC | AAT | GAA | AAA | CAG |
| Arg | Val | Thr | Ala | Ile | Leu | Asp | Lys | Leu | Ile | Thr | MET | Thr | Ile | Asn | Glu | Lys | Gln |
| Glu | Leu | Leu | Leu | Phe | Leu | Thr | Ser | . | . | Gln | . | Pro | Ser | MET | Lys | Asn | Arg |
| Ser Tyr | Cys | Tyr | Ser | . | Gln | Ala | Asp | Asn | Asn | Asp | His | Gln | . | Lys | Thr | Asp | |
| | | | | | | | | 3699 | | | | | | | | | 3726 |
| ATG | TAC | CCA | TCT | ATT | CAA | GCA | AAA | ATA | TGG | GGA | AGC | CTT | GGG | CAG | ATT | ACA | GAT |
| MET | Tyr | Pro | Ser | Ile | Gln | Ala | Lys | Ile | Trp | Gly | Ser | Leu | Gly | Gln | Ile | Thr | Asp |
| Cys | Thr | His | Leu | Phe | Lys | Gln | Lys | Tyr | Gly | Glu | Ala | Leu | Gly | Arg | Leu | Gln | Ile |
| Val | Pro | Ile | Tyr | Ser | Ser | Lys | Asn | MET | Gly | Lys | Pro | Trp | Ala | Asp | Tyr | Arg | Ser |
| | | | | | | | | 3753 | | | | | | | | | 3780 |
| CTG | CTT | GAT | GTT | GTA | CTA | GAC | AGT | TTC | ATC | AAA | ACC | AGT | GCA | ACA | GGT | GGC | TTG |
| Leu | Leu | Asp | Val | Val | Leu | Asp | Ser | Phe | Ile | Lys | Thr | Ser | Ala | Thr | Gly | Gly | Leu |
| Cys | Leu | MET | Leu | Tyr | . | Thr | Val | Ser | Ser | Lys | Pro | Val | Gln | Gln | Val Ala | Trp | |
| Ala | . | Cys | Cys | Thr | Arg | Gln | Phe | His | Gln | Asn | Gln | Cys | Asn | Arg | Trp | Leu | Gl |
| | | | | | | | | 3807 | | | | | | | | | 3834 |
| GGA | TCA | ATA | AAA | GCT | GAG | GTG | ATG | GCA | GAT | ACT | GCT | GTA | GCT | TTG | GCT | TCT | GGA |
| Gly | Ser | Ile | Lys | Ala | Glu | Val | MET | Ala | Asp | Thr | Ala | Val | Ala | Leu | Ala | Ser | Gly |
| Asp | Gln | . | Lys | Leu | Arg | . | Trp | Gln | Ile | Leu | Leu | . | Leu | Trp | Leu | Leu | Glu |
| Ile | Asn | Lys | Ser | . | Gly | Asp | Gly | Arg | Tyr | Cys | Cys | Ser | Phe | Gly | Phe | Trp | Lys |

TABLE 2-continued

| | | | | | | | | | | | | | | | | | |
|---|---|---|---|---|---|---|---|---|---|---|---|---|---|---|---|---|---|
| | | | | | | | | 3861 | | | | | | | | | 3888 |
| AAT | GTG | AAA | TTG | GTT | TCA | AGC | AAG | GTT | ATT | GGA | AGG | ATG | TGC | AAA | ATA | ATT | GAC |
| Asn | Val | Lys | Leu | Val | Ser | Ser | Lys | Val | Ile | Gly | Arg | MET | Cys | Lys | Ile | Ile | Asp |
| MET | . | Asn | Trp | Phe | Gln | Ala | Arg | Leu | Leu | Glu | Gly | Cys | Ala | Lys | . | Leu | Thr |
| Cys | Glu | Ile | Gly | Phe | Lys | Gln | Gly | Tyr | Trp | Lys | Asp | Val | Gln | Asn Asn | . | Gln | |
| | | | | | | | | 3915 | | | | | | | | | 3942 |
| AAG | ACA | TGC | TTA | TCT | CCA | ACT | CCT | ACT | TTA | GAA | CAA | CAT | CTT | ATG | TGG | GAT | GAT |
| Lys | Thr | Cys | Leu | Ser | Pro | Thr | Pro | Thr | Leu | Glu | Gln | His | Leu | MET | Trp | Asp | Asp |
| Arg | His | Ala | Tyr | Leu | Gln | Leu | Leu | Leu | . | Asn | Asn | Ile | Leu | Cys | Gly | MET | Ile |
| Asp | MET | Leu | Ile | Ser | Asn | Ser | Tyr | Phe | Arg | Thr | Thr | Ser | Tyr | Val | Gly | . | Tyr |
| | | | | | | | | 3969 | | | | | | | | | 3996 |
| ATT | GCT | ATT | TTA | GCA | CGC | TAC | ATG | CTG | ATG | CTG | TCC | TTC | AAC | AAT | TCC | CTT | GAT |
| Ile | Ala | Ile | Leu | Ala | Arg | Tyr | MET | Leu | MET | Leu | Ser | Phe | Asn | Asn | Ser | Leu | Asp |
| Leu | Leu | Phe | . | His | Ala | Thr | Cys | . | Cys | Cys | Pro | Ser | Thr | Ile | Pro | Leu | MET |
| Cys | Tyr | Phe | Ser | Thr | Leu | His | Ala | Asp | Ala | Val | Leu | Gln | Gln | Phe | Pro | . | Cys |
| | | | | | | | | 4023 | | | | | | | | | 4050 |
| GTG | GCA | GCT | CAT | CTT | CCC | TAC | CTC | TTC | CAC | GTT | GTT | ACT | TTC | TTA | GTA | GCC | ACA |
| Val | Ala | Ala | His | Leu | Pro | Tyr | Leu | Phe | His | Val | Val | Thr | Phe | Leu | Val | Ala | Thr |
| Trp | Gln | Leu | Ile | Phe | Pro | Thr | Ser | Ser | Thr | Leu | Leu | Leu | Ser | . | . | Pro | Gln |
| Gly | Ser | Ser | Ser | Ser | Leu | Pro | Leu | Pro | Arg | Cys | Tyr | Phe | Leu | Ser | Ser | His | Arg |
| | | | | | | | | 4077 | | | | | | | | | 4104 |
| GGT | CCG | CTC | TCC | CTT | AGA | GCT | TCC | ACA | CAT | GGA | CTG | GTC | ATT | AAT | ATC | ATT | CAC |
| Gly | Pro | Leu | Ser | Leu | Arg | Ala | Ser | Thr | His | Gly | Leu | Val | Ile | Asn | Ile | Ile | His |
| Val | Arg | Ser | Pro | Leu | Glu | Leu | Pro | His | MET | Asp | Trp | Ser | Leu | Ile | Ser | Phe | Thr |
| Ser | Ala | Leu | Pro | . | Ser | Phe | His | Thr | Trp | Thr | Gly | His | . | Tyr | His | Ser | Leu |
| | | | | | | | | 4131 | | | | | | | | | 4158 |
| TCT | CTG | TGT | ACT | TGT | TCA | CAG | CTT | CAT | TTT | AGT | GAA | GAG | ACC | AAG | CAA | GTT | TTG |
| Ser | Leu | Cys | Thr | Cys | Ser | Gln | Leu | His | Phe | Ser | Glu | Glu | Thr | Lys | Gln | Val | Leu |
| Leu | Cys | Val | Leu | Val | His | Ser | Phe | Ile | Leu | Val | Lys | Arg | Pro | Ser | Lys | Phe | . |
| Ser | Val | Tyr | Leu | Phe | Thr | Ala | Ser | Phe | . | . | Arg | Asp | Gln | Ala | Ser | phe | Glu |
| | | | | | | | | 4185 | | | | | | | | | 4212 |
| AGA | CTC | AGT | CTG | ACA | GAG | TTC | TCA | TTA | CCC | AAA | TT | TAC | TTG | CTG | TTT | GGC | ATT |
| Arg | Leu | Ser | Leu | Thr | Glu | Phe | Ser | Leu | Pro | Lys | Phe | Tyr | Leu | Leu | Phe | Gly | Ile |
| Asp | Ser | Val | . | Gln | Ser | Ser | His | Tyr | Pro | Asn | Phe | Thr | Cys | Cys | Leu | Ala | Leu |
| Thr | Gln | Ser | Asp | Arg | Val | Leu | Ile | Thr | Gln | Ile | Leu | Leu | Ala | Val Trp | His | . | |
| | | | | | | | | 4239 | | | | | | | | | 4266 |
| AGC | AAA | GTC | AAG | TCA | GCT | GCT | GTC | ATT | GCC | TTC | CGT | TCC | AGT | TAC | CGG | GAC | AGG |
| Ser | Lys | Val | Lys | Ser | Ala | Ala | Val | Ile | Ala | Phe | Arg | Ser | Ser | Tyr | Arg | Asp | Arg |
| Ala | Lys | Ser | Ser | Gln | Leu | Leu | Ser | Leu | Pro | Ser | Val | Pro | Val | Thr | Gly | Thr | Gly |
| Gln | Ser | Gln | Val | Ser | Cys | Cys | His | Cys | Leu | Pro | Phe | Gln | Leu | Pro | Gly | Gln | Val |
| | | | | | | | | 4293 | | | | | | | | | 4320 |
| TCA | TTC | TCT | CCT | GGC | TCC | TAT | GAG | AGA | GAG | ACT | TTT | GCT | TTG | ACA | TCC | TTG | GAA |
| Ser | Phe | Ser | Pro | Gly | Ser | Tyr | Glu | Arg | Glu | Thr | Phe | Ala | Leu | Thr | Ser | Leu | Glu |
| His | Ser | Leu | Leu | Ala | Pro | MET | Arg | Glu | Arg | Leu | Leu | Leu | . | His | Pro | Trp | Lys |

TABLE 2-continued

| Ile | Leu | Ser | Trp | Leu | Leu | . | Glu | Arg | Asp | Phe | Cys | Phe | Asp | Ile | Leu | Gly | Asn |
|---|---|---|---|---|---|---|---|---|---|---|---|---|---|---|---|---|---|
| | | | | | | | | 4347 | | | | | | | | | 4374 |
| ACA | GTC | ACA | GAA | GCT | TTG | TTG | GAG | ATC | ATG | GAG | GCA | TGC | ATG | AGA | GAT | ATT | CCA |
| Thr | Val | Thr | Glu | Ala | Leu | Leu | Glu | Ile | MET | Glu | Ala | Cys | MET | Arg | Asp | Ile | Pro |
| Gln | Ser | Gln | Lys | Leu | Cys | Trp | Arg | Ser | Trp | Arg | His | Ala | . | Glu | Ile | Phe | Gln |
| Ser | His | Arg | Ser | Phe | Val | Gly | Asp | His | Gly | Gly | MET | His | Glu | Arg | Tyr | Ser | Asn |
| | | | | | | | | 4401 | | | | | | | | | 4428 |
| ACG | TGC | AAG | TGG | CTG | GAC | CAG | TGG | ACA | GAA | CTA | GCT | CAA | AGA | TTT | GCA | TTC | CAA |
| Thr | Cys | Lys | Trp | Leu | Asp | Gln | Trp | Thr | Glu | Leu | Ala | Gln | Arg | Phe | Ala | Phe | Gln |
| Arg | Ala | Ser | Gly | Trp | Thr | Ser | Gly | Gln | Asn | . | Leu | Lys | Asp | Leu | His | Ser | Asn |
| Val Gln | Val | Ala | Gly | Pro | Val | Asp | Arg | Thr | Ser | Ser | Lys | Ile | Cys | Ile | Pro | Ile | |
| | | | | | | | | 4455 | | | | | | | | | 4482 |
| TAT | AAT | CCA | TCC | CTG | CAA | CCA | AGA | GCT | CTT | GTT | GTC | TTT | GGG | TGT | ATT | AGC | AAA |
| Tyr | Asn | Pro | Ser | Leu | Gln | Pro | Arg | Ala | Leu | Val | Val | Phe | Gly | Cys | Ile | Ser | Lys |
| Ile | Ile | His | Pro | Cys | Asn | Gln | Glu | Leu | Leu | Leu | Ser | Leu | Gly | Val | Leu | Ala | Asn |
| . | Ser | Ile | Pro | Ala | Thr | Lys | Ser | Ser | Cys | Cys | Leu | Trp | Val | Tyr | . | Gln | Thr |
| | | | | | | | | 4509 | | | | | | | | | 4536 |
| CGA | GTG | TCT | CAT | GGG | CAG | ATA | AAG | CAG | ATA | ATC | CGT | ATT | CTT | AGC | AAG | GCA | CTT |
| Arg | Val | Ser | His | Gly | Gln | Ile | Lys | Gln | Ile | Ile | Arg | Ile | Leu | Ser | Lys | Ala | Leu |
| Glu | Cys | Leu | MET | Gly | Arg | . | Ser | Arg | . | Ser | Val | Phe | Leu | Ala | Arg | His | Leu |
| Ser | Val | Ser | Trp | Ala | Asp | Lys | Ala | Asp | Asn | Pro | Tyr | Ser | . | Gln | Gly | Thr | . |
| | | | | | | | | 4563 | | | | | | | | | 4590 |
| GAG | AGT | TGC | TTA | AAA | GGA | CCT | GAC | ACT | TAC | AAC | AGT | CAA | GTT | CTG | ATA | GAA | GCT |
| Glu | Ser | Cys | Leu | Lys | Gly | Pro | Asp | Thr | Tyr | Asn | Ser | Gln | Val | Leu | Ile | Glu | Ala |
| Arg | Val | Ala | . | Lys | Asp | Leu | Thr | Leu | Thr | Thr | Val | Lys | Phe | . | . | Lys | Leu |
| Glu | Leu | Leu | Lys | Arg | Thr | . | His | Leu | Gln | Gln | Ser | Ser | Ser | Asp | Arg | Ser | Tyr |
| | | | | | | | | 4617 | | | | | | | | | 4644 |
| ACA | GTA | ATA | GCA | CTA | ACC | AAA | TTA | CAG | CCA | CTT | CTT | AAT | AAG | GAC | TCG | CCT | CTG |
| Thr | Val | Ile | Ala | Leu | Thr | Lys | Leu | Gln | Pro | Leu | Leu | Asn | Lys | Asp | Ser | Pro | Leu |
| Gln | . | . | His | . | Pro | Asn | Tyr | Ser | His | Phe | Leu | Ile | Arg | Thr | Arg | Leu | Cys |
| Ser | Asn Ser | Thr | Asn | Gln | Ile | Thr | Ala | Thr | Ser | . | . | Gly | Leu | Ala | Ser | Ala | |
| | | | | | | | | 4671 | | | | | | | | | 4698 |
| CAC | AAA | GCC | CTC | TTT | TGG | GTA | GCT | GTG | GCT | GTG | CTG | CAG | CTT | GAT | GAG | GTC | AAC |
| His | Lys | Ala | Leu | Phe | Trp | Val | Ala | Val | Ala | Val | Leu | Gln | Leu | Asp | Glu | Val | Asn |
| Thr | Lys | Pro | Ser | Phe | Gly | . | Leu | Trp | Leu | Cys | Cys | Ser | Leu | MET | Arg | Ser | Thr |
| Gln | Ser | Pro | Leu | Leu | Gly | Ser | Cys | Gly | Cys | Ala | Ala | Ala | . | . | Gly | Gln | Leu |
| | | | | | | | | 4725 | | | | | | | | | 4752 |
| TTG | TAT | TCA | GCA | GGT | ACC | GCA | CTT | CTT | GAA | CAA | AAC | CTG | CAT | ACT | TTA | GAT | AGT |
| Leu | Tyr | Ser | Ala | Gly | Thr | Ala | Leu | Leu | Glu | Gln | Asn | Leu | His | Thr | Leu | Asp | Ser |
| Cys | Ile | Gln | Gln | Val | Pro | His | Phe | Leu | Asn | Lys | Thr | Cys | Ile | Leu | . | Ile | Val |
| Val | Phe | Ser | Arg | Tyr | Arg | Thr | Ser | . | Thr | Lys | Pro | Ala | Tyr | Phe | Arg | . | Ser |
| | | | | | | | | 4779 | | | | | | | | | 4806 |
| CTC | CGT | ATA | TTC | AAT | GAC | AAG | AGT | CCA | GAG | GAA | GTA | TTT | ATG | GCA | ATC | CGG | AAT |
| Leu | Arg | Ile | Phe | Asn | Asp | Lys | Ser | Pro | Glu | Glu | Val | Phe | MET | Ala | Ile | Arg | Asn |

TABLE 2-continued

| | | | | | | | | | | | | | | | | | |
|---|---|---|---|---|---|---|---|---|---|---|---|---|---|---|---|---|---|
| Ser | Val | Tyr | Ser | MET | Thr | Arg | Val | Gln | Arg | Lys | Tyr | Leu | Trp | Gln | Ser | Gly | Ile |
| Pro | Tyr | Ile | Gln | . | Gln | Glu | Ser | Arg | Gly | Ser | Ile | Tyr | Gly | Asn | Pro | Glu | Ser |
| | | | | | | | | 4833 | | | | | | | | | 4860 |
| CCT | CTG | GAG | TGG | CAC | TGC | AAG | CAA | ATG | GAT | CAT | TTT | GTT | GGA | CTC | AAT | TTC | AAC |
| Pro | Leu | Glu | Trp | His | Cys | Lys | Gln | MET | Asp | His | Phe | Val | Gly | Leu | Asn | Phe | Asn |
| Leu | Trp | Ser | Gly | Thr | Ala | Ser | Lys | Trp | Ile | Ile | Leu | Leu | Asp | Ser | Ile | Ser | Thr |
| Ser | Gly | Val | Ala | Leu | Gln | Ala | Asn | Gly | Ser | Phe | Cys | Trp | Thr | Gln | Phe | Gln Leu | |
| | | | | | | | | 4887 | | | | | | | | | 4914 |
| TCT | AAC | TTT | AAC | TTT | GCA | TTG | GTT | GGA | CAC | CTT | TTA | AAA | GGG | TAC | AGG | CAT | CCT |
| Ser | Asn | Phe | Asn | Phe | Ala | Leu | Val | Gly | His | Leu | Leu | Lys | Gly | Tyr | Arg | His | Pro |
| Leu | Thr | Leu | Thr | Leu | His | Trp | Leu | Asp | Thr | Phe | . | Lys | Gly Thr | Gly | Ile | Leu | |
| . | Leu | . | Leu | Cys | Ile | Gly | Trp | Thr | Pro | Phe | Lys | Arg | Val | Gln Ala | Ser | Phe | |
| | | | | | | | | 4941 | | | | | | | | | 4968 |
| TCA | CCT | GCT | ATT | GTT | GCA | AGA | ACA | GTC | AGA | ATT | TTA | CAT | ACA | CTA | CTA | ACT | CTG |
| Ser | Pro | Ala | Ile | Val | Ala | Arg | Thr | Val | Arg | Ile | Leu | His | Thr | Leu | Leu | Thr | Leu |
| His | Leu | Leu | Leu | Leu | Gln | Glu | Gln | Ser | Glu | Phe | Tyr | Ile | His | Tyr | . | Leu | Trp |
| Thr | Cys | Tyr | Cys | Cys | Lys | Asn | Ser | Gln | Asn | Phe | Thr | Tyr | Thr | Thr | Asn | Ser | Gly |
| | | | | | | | | 4995 | | | | | | | | | 5022 |
| GTT | AAC | AAA | CAC | AGA | AAT | TGT | GAC | AAA | TTT | GAA | GTG | AAT | ACA | CAG | AGC | CTG | GCC |
| Val | Asn | Lys | His | Arg | Asn | Cys | Asp | Lys | Phe | Glu | Val | Asn | Thr | Gln | Ser | Val | Ala |
| Leu | Thr | Asn | Thr | Glu | Ile | Val | Thr | Asn | Leu | Lys | . | Ile | His | Arg | Ala | Trp | Pro |
| . | Gln | Thr | Gln | Lys | Leu | . | Gln | Ile | . | Ser | Glu | Tyr | Thr | Glu | Arg | Gly | Leu |
| | | | | | | | | 5049 | | | | | | | | | 5076 |
| TAC | TTA | GCA | GCT | TTA | CTT | ACA | GTG | TCT | GAA | GAA | GTT | CGA | AGT | CGC | TGC | AGC | CTA |
| Tyr | Leu | Ala | Ala | Leu | Leu | Thr | Val | Ser | Glu | Glu | Val | Arg | Ser | Arg | Cys | Ser | Leu |
| Thr | . | Gln | Leu | Tyr | Leu | Gln | Cys | Leu | Lys | Lys | Phe | Glu | Val | Ala | Ala | Ala | . |
| Leu | Ser | Ser | Phe | Thr | Tyr | Ser | Val | . | Arg | Ser | Ser | Lys | Ser | Leu | Gln | Pro | Lys |
| | | | | | | | | 5103 | | | | | | | | | 5130 |
| AAA | CAT | AGA | AAG | TCA | CTT | CTT | CTT | ACT | GAT | ATT | TCA | ATG | GAA | AAT | GTT | CCT | ATG |
| Lys | His | Arg | Lys | Ser | Leu | Leu | Leu | Thr | Asp | Ile | Ser | MET | Glu Asn | Val | Pro | MET | |
| Asn | Ile | Glu | Ser | His | Phe | Phe | Leu | Leu | Ile | Phe | Gln | Trp | Lys | MET | Phe Leu | Trp | |
| Thr | . | Lys | Val | Thr | Ser | Ser | Tyr | . | Tyr | Phe | Asn | Gly | Lys | Cys | Ser | Tyr | Gly |
| | | | | | | | | 5157 | | | | | | | | | 5184 |
| GAT | ACA | TAT | CCC | ATT | CAT | CAT | GGT | GAC | CCT | TCC | TAT | AGG | ACA | CTA | AAG | GAG | ACT |
| Asp | Thr | Tyr | Pro | Ile | His | His | Gly | Asp | Pro | Ser | Tyr | Arg | Thr | Leu | Lys | Glu | Thr |
| Ile | His | Ile | Pro | Phe | Ile | MET | Val | Thr | Leu | Pro | Ile | Gly | His | . | Arg | Arg | Leu |
| Tyr | Ile | Ser | His | Ser | Ser | Trp | . | Pro | Phe | Leu | . | Asp | Thr | Lys | Gly | Asp | Ser |
| | | | | | | | | 5211 | | | | | | | | | 5238 |
| CAG | CCA | TGG | TCC | TCT | CCC | AAA | GGT | TCT | GAA | GGA | TAC | CTT | GCA | GCC | ACC | TAT | CCA |
| Gln | Pro | Trp | Ser | Ser | Pro | Lys | Gly | Ser | Glu | Gly | Tyr | Leu | Ala | Ala | Thr | Tyr | Pro |
| Ser | His | Gly | Pro | Leu | Pro | Lys | Val | Leu | Lys | Asp | Thr | Leu | Gln | Pro | Pro | Ile | Gln |
| Ala | MET | Val | Leu | Ser | Gln | Arg | Phe | . | Arg | Ile | Pro | Cys | Ser | His Leu | Ser | Asn | |
| | | | | | | | | 5265 | | | | | | | | | 5292 |
| ACT | GTC | GGC | CAG | ACC | AGT | CCC | CGA | GCC | AGG | AAA | TCC | ATG | AGC | CTG | GAC | ATG | GGG |

TABLE 2-continued

| | | | | | | | | | | | | | | | | | |
|---|---|---|---|---|---|---|---|---|---|---|---|---|---|---|---|---|---|
| Thr<br>Leu<br>Cys | Val<br>Ser<br>Arg | Gly<br>Ala<br>Pro | Gln<br>Arg<br>Asp | Thr<br>Pro<br>Gln | Ser<br>Val<br>Ser | Pro<br>Pro<br>Pro | Arg<br>Glu<br>Ser | Ala<br>Pro<br>Gln | Arg<br>Gly<br>Glu | Lys<br>Asn<br>Ile | Ser MET<br>Pro<br>His | Ser<br>.<br>Glu | Leu<br>Ala<br>Pro | Asp<br>Trp<br>Gly | MET<br>Thr<br>His | Gly<br>Trp<br>Gly | Gly<br>Ala |
| CAA<br>Gln<br>Asn<br>Thr | CCT<br>Pro<br>Leu<br>Phe | TCT<br>Ser<br>Leu<br>Ser | CAG<br>Gln<br>Arg<br>Gly | GCC<br>Ala<br>Pro<br>Gln | AAC<br>Asn<br>Thr<br>His | ACT<br>Thr<br>Leu<br>. | AAG<br>Lys<br>Arg<br>Glu | 5319<br>AAG<br>Lys<br>Ser<br>Val | TTG<br>Leu<br>Cys<br>Ala | CTT<br>Leu<br>Leu<br>Trp | GGA<br>Gly<br>Gln<br>Asn | ACA<br>hr<br>Gln<br>Lys | AGG<br>Arg<br>Gly<br>Glu | AAA<br>Lys<br>Lys<br>Lys | AGT<br>Ser<br>Val<br>Phe | TTT<br>Phe<br>Leu<br>. | 5346<br>GAT<br>Asp<br>Ile<br>Ser |
| CAC<br>His<br>Thr<br>Leu | TTG<br>Leu<br>.<br>Asp | ATA<br>Ile<br>Tyr<br>Ile | TCA<br>Ser<br>Gln<br>Arg | GAC<br>Asp<br>Thr<br>His | ACA<br>Thr<br>Gln<br>Lys | AAG<br>Lys<br>Arg<br>Gly | GCT<br>Ala<br>Leu<br>Ser | 5373<br>CCT<br>Pro<br>Leu<br>. | AAA<br>Lys<br>Lys<br>Lys | AGG<br>Arg<br>Gly<br>Ala | CAA<br>Gln<br>Lys<br>Arg | GAA<br>Glu<br>Lys<br>Asn | ATG<br>MET<br>Trp<br>Gly | GAA<br>Glu<br>Asn<br>Ile | TCA<br>Ser<br>Gln<br>Arg | GGG<br>Gly<br>Gly<br>Asp | 5400<br>ATC<br>Ile<br>Ser<br>His |
| ACA<br>Thr<br>Gln<br>Asn | ACA<br>Thr<br>His<br>Thr | CCC<br>Pro<br>Pro<br>Pro | CCC<br>Pro<br>Pro<br>Gln | AAA<br>Lys<br>Lys<br>Asn | ATG<br>MET<br>.<br>Glu | AGG<br>Arg<br>Gly<br>Glu | AGA<br>Arg<br>Glu<br>Ser | 5427<br>GTA<br>Val<br>.<br>Ser | GCA<br>Ala<br>Gln<br>Arg | GAA<br>Glu<br>Lys<br>Asn | ACT<br>Thr<br>Leu<br>. | GAT<br>Asp<br>Ile<br>Leu | TAT<br>Tyr<br>MET<br>. | GAA<br>Glu<br>Lys<br>Asn | ATG<br>MET<br>Trp<br>Gly | GAA<br>Glu<br>Lys<br>Asn | 5454<br>ACT<br>Thr<br>Leu<br>Ser |
| CAG<br>Gln<br>Arg<br>Glu | AGG<br>Arg<br>Gly<br>Asp | ATT<br>Ile<br>Phe<br>Phe | TCC<br>Ser<br>Pro<br>Leu | TCA<br>Ser<br>His<br>Ile | TCA<br>Ser<br>His<br>Thr | CAA<br>Gln<br>Asn<br>Thr | CAG<br>Gln<br>Ser<br>Ala | 5481<br>CAC<br>His<br>Thr<br>Pro | CCA<br>Pro<br>His<br>Thr | CAT<br>His<br>Ile<br>Phe | TTA<br>Leu<br>Tyr<br>Thr | CGT<br>Arg<br>Val<br>. | AAA<br>Lys<br>Lys<br>Ser | GTT<br>Val<br>Phe<br>Phe | TCA<br>Ser<br>Gln<br>Ser | GTG<br>Val<br>Cys<br>Val | 5508<br>TCT<br>Ser<br>Leu<br>. |
| GAA<br>Glu<br>Asn<br>Ile | TCA<br>Ser<br>Gln<br>Lys | AAT<br>Asn<br>MET<br>Cys | GTT<br>Val<br>Phe<br>Ser | CTC<br>Leu<br>Ser<br>Leu | TTG<br>Leu<br>Trp<br>Gly | GAT<br>Asp<br>MET<br>. | GAA<br>Glu<br>Lys<br>Arg | 5535<br>GAA<br>Glu<br>Lys<br>Ser | GTA<br>Val<br>Tyr<br>Thr | CTT<br>Leu<br>Leu<br>Tyr | ACT<br>Thr<br>Leu<br>. | GAT<br>Asp<br>Ile<br>Ser | CCG<br>Pro<br>Arg<br>Glu | AAG<br>Lys<br>Arg<br>Asp | ATC<br>Ile<br>Ser<br>Pro | CAG<br>Gln<br>Arg<br>Gly | 5562<br>GCG<br>Ala<br>Arg<br>Ala |
| CTG<br>Leu<br>Cys<br>Ala | CTT<br>Leu<br>Phe<br>Ser | CTT<br>Leu<br>Leu<br>Tyr | ACT<br>Thr<br>Leu<br>Cys | GTT<br>Val<br>Phe<br>Ser | CTA<br>Leu<br>.<br>Ser | GCT<br>Ala<br>Leu<br>Tyr | ACA<br>Thr<br>His<br>Thr | •5589<br>CTG<br>Leu<br>Trp<br>Gly | GTA<br>Val<br>.<br>Lys | AAA<br>Lys<br>Asn<br>Ile | TAT<br>Tyr<br>Ile<br>Tyr | ACC<br>Thr<br>Pro<br>His | ACA<br>Thr<br>Gln<br>Arg | GAT<br>Asp<br>MET<br>. | GAG<br>Glu<br>Ser<br>Val | TTT<br>Phe<br>Leu<br>. | 5616<br>GAT<br>Asp<br>Ile<br>Ser |
| CAA<br>Gln<br>Asn<br>Thr | CGA<br>Arg<br>Glu<br>Asn | ATT<br>Ile<br>Phe<br>Ser | CTT<br>Leu<br>Phe<br>Leu | TAT<br>Tyr<br>MET<br>. | GAA<br>Glu<br>Asn<br>Ile | TAC<br>Tyr<br>Thr<br>Leu | TTA<br>Leu<br>.<br>Ser | 5643<br>GCA<br>Ala<br>Gln<br>Arg | GAG<br>Glu<br>Arg<br>Gly | GCC<br>Ala<br>Pro<br>Gln | AGT<br>Ser<br>Val<br>Cys | GTT<br>Val<br>Leu<br>Cys | GTG<br>Val<br>Cys<br>Val | TTT<br>Phe<br>Phe<br>Ser | CCC<br>Prb<br>Pro<br>Gln | AAA<br>Lys<br>Lys<br>Ser | 5670<br>GTC<br>Val<br>Ser<br>Leu |
| TTT<br>Phe<br>Phe<br>Ser | CCT<br>Pro<br>Leu<br>Cys | GTT<br>Val<br>Leu<br>Cys | GTG<br>Val<br>Cys<br>Ala | CAT<br>His<br>Ile<br>. | AAT<br>Asn<br>Ile<br>Phe | TTG<br>Leu<br>Cys<br>Val | TTG<br>Leu<br>Trp<br>Gly | 5697<br>GAC<br>Asp<br>Thr<br>Leu | TCT<br>Ser<br>Leu<br>. | AAG<br>Lys<br>Arg<br>Asp | ATC<br>Ile<br>Ser<br>Gln | AAC<br>Asn<br>Thr<br>His | ACC<br>Thr<br>Pro<br>Pro | CTG<br>Leu<br>Cys Tyr<br>Val | TTA<br>Leu<br>His<br>Ile | TCA<br>Ser<br>Cys<br>Ile | 5724<br>TTG<br>Leu<br><br>Val |
| | | | | | | | | 5751 | | | | | | | | 5778 | |

TABLE 2-continued

| | | | | | | | | | | | | | | | | | |
|---|---|---|---|---|---|---|---|---|---|---|---|---|---|---|---|---|---|
| TGC<br>Cys<br>Ala<br>Pro | CAA<br>Gln<br>Lys<br>Arg | GAT<br>Asp<br>Ile<br>Ser | CCA<br>Pro<br>Gln<br>Lys | AAT<br>Asn<br>Ile<br>Phe | TTG<br>Leu<br>Cys<br>Val | TTA<br>Leu<br>.<br>Lys | AAT<br>Asn<br>Ile<br>Ser | CCA<br>Pro<br>Gln<br>Asn | ATC<br>Ile<br>Ser<br>Pro | CAT<br>His<br>MET<br>Trp | GGA<br>Gly<br>Glu<br>Asn | ATT<br>Ile<br>Leu<br>Cys | GTG<br>Val<br>Cys<br>Ala | CAG<br>Gln<br>Arg<br>Glu | AGT<br>Ser<br>Val<br>Cys | GTG<br>Val<br>Trp<br>Gly | GTG<br>Val<br>Cys<br>Val |
| TAC<br>Tyr<br>Thr<br>Pro | CAT<br>His<br>MET<br>. | GAA<br>Glu<br>Lys<br>Arg | GAA<br>Glu<br>Asn<br>Ile | TCC<br>Ser<br>Pro<br>Pro | CCA<br>Pro<br>His<br>Thr | CCA<br>Pro<br>His<br>Thr | CAA<br>Gln<br>Asn<br>Ile | 5805<br>TAC<br>Tyr<br>Thr<br>Pro | CAA<br>Gln<br>Lys<br>Asn Ile | ACA<br>Thr<br>His<br>Leu | TCT<br>Ser<br>Leu<br>Pro | TAC<br>Tyr<br>Thr<br>Ala | CTG<br>Leu<br>Cys<br>Lys | CAA<br>Gln<br>Lys<br>Phe | AGT<br>Ser<br>Val<br>Trp | TTT<br>Phe<br>Leu<br>Phe | 5832<br>GGT<br>Gly<br>Val |
| TTT<br>Phe<br>Leu<br>. | AAT<br>Asn<br>MET<br>Trp | GGC<br>Gly<br>Ala<br>Leu | TTG<br>Leu<br>Cys<br>Val | TGG<br>Trp<br>Gly<br>Ala | CGG<br>Arg<br>Gly<br>Val | TTT<br>Phe<br>Leu<br>Cys | GCA<br>Ala<br>Gln<br>Arg | 5859<br>GGA<br>Gly<br>Asp<br>Thr | CCG<br>Pro<br>Arg<br>Val | TTT<br>Phe<br>Phe<br>Phe | TCA<br>Ser<br>Gln<br>Lys | AAG<br>Lys<br>Ser<br>Ala | CAA<br>Gln<br>Lys<br>Asn | ACA<br>Thr<br>His<br>Thr | CAA<br>Gln<br>Lys<br>Asn | ATT<br>Ile<br>Phe<br>Ser | 5886<br>CCA<br>Pro<br>Gln<br>Arg |
| GAC<br>Asp<br>Thr<br>Leu | TAT<br>Tyr<br>MET<br>Cys | GCT<br>Ala<br>Leu<br>. | GAG<br>Glu<br>Ser<br>Ala | CTT<br>Leu<br>Leu<br>Tyr | ATT<br>Ile<br>Leu<br>Cys | GTT<br>Val<br>Leu<br>. | AAG<br>Lys<br>Ser<br>Val | 5913<br>TTT<br>Phe<br>Phe<br>Ser | CTT<br>Leu<br>Leu<br>. | GAT<br>Asp<br>MET<br>Cys | GCC<br>Asl<br>Pro<br>Leu | TTG<br>Leu<br>.<br>Asp | ATT<br>Ile<br>Leu<br>. | GAC<br>Asp<br>Thr<br>His | ACG<br>Thr<br>Arg<br>Val | TAC<br>Tyr<br>Thr<br>Pro | 5940<br>CTG<br>Leu<br>Cys<br>Ala |
| CCT<br>Pro<br>Leu<br>Trp | GGA<br>Gly<br>Glu<br>Asn | ATT<br>Ile<br>Leu<br>. | GAT<br>Asp<br>MET<br>. | GAA<br>Glu<br>Lys<br>Arg | GAA<br>Glu<br>Lys<br>Asn | ACC<br>Thr<br>Pro<br>Gln | AGT<br>Ser<br>Val<br>. | 5967<br>GAA<br>Glu<br>Lys<br>Arg | GAA<br>Glu<br>Asn<br>Ile | TCC<br>Ser<br>Pro<br>Pro | CTC<br>Leu<br>Ser<br>Pro | CTG<br>Leu<br>.<br>Asp | ACT<br>Thr<br>Leu<br>Ser | CCC<br>Pro<br>Pro<br>His | ACA<br>Thr<br>His<br>Ile | TCT<br>Ser<br>Leu<br>Ser | 5994<br>CCT<br>Pro<br>Leu<br>Leu |
| TAC<br>Tyr<br>Thr<br>Pro | CCT<br>Pro<br>Leu<br>Ser | CCT<br>Pro<br>Leu<br>Cys | GCA<br>Ala<br>His<br>Thr | CTG<br>Leu<br>Cys<br>Ala | CAG<br>Gln<br>Arg<br>Glu | AGC<br>Ser<br>Ala<br>Pro | CAG<br>Gln<br>Ser<br>Ala | 6021<br>CTT<br>Leu<br>Leu<br>. | AGT<br>Ser<br>Val<br>Tyr | ATC<br>Ile<br>Ser<br>His | ACT<br>Thr<br>Leu<br>Cys | GCC<br>Ala<br>Pro<br>Gln | AAC<br>Asn<br>Thr<br>Pro | CTT<br>Leu<br>Leu<br>. | AAC<br>Asn<br>Thr<br>Pro | CTT<br>Leu<br>Phe<br>Phe | 6048<br>TCT<br>Ser<br>Leu<br>. |
| AAT<br>Asn<br>Ile<br>Phe | TCC<br>Ser<br>Pro<br>His | ATG<br>MET<br>.<br>Asp | ACC<br>Thr<br>Pro<br>Leu | TCA<br>Ser<br>His<br>Thr | CTT<br>Leu<br>Leu<br>Cys | GCA<br>Ala<br>Gln<br>Asn | ACT<br>Thr<br>Leu<br>Phe | 6075<br>TCC<br>Ser<br>Pro<br>Pro | CAG<br>Gln<br>Ser<br>Ala | CAT<br>His<br>Ile<br>Phe | TCC<br>Ser<br>Pro<br>Pro | CCA<br>Pro<br>Gln<br>Ser | GCT<br>Ala<br>Leu<br>Phe | TCT<br>Ser<br>Leu<br>Ser | CTG<br>Leu<br>Cys<br>Ala | CCT<br>Pro<br>Leu<br>Leu | 6102<br>TGC<br>Cys<br>Ala<br>Leu |
| TCT<br>Ser<br>Leu<br>. | AAC<br>Asn<br>Thr<br>Leu | TCA<br>Ser<br>Gln<br>Ser | GCA<br>Ala<br>Gln<br>Ser | GTT<br>Val<br>Phe<br>Phe | TTC<br>Phe<br>Ser<br>His | ATG<br>MET<br>Cys<br>Ala | CAG<br>Gln<br>Ser<br>Ala | 6129<br>CTG<br>Leu<br>Cys<br>Val | TTC<br>Phe<br>Ser<br>Pro | CCT<br>Pro<br>Leu<br>Ser | CAT<br>His<br>Ile<br>Ser | CAA<br>Gln<br>Lys<br>Arg | GGA<br>Gly<br>Glu<br>Asn | ATC<br>Ile<br>Ser<br>Arg | GAC<br>Asp<br>Thr<br>Gln | AAG<br>Lys<br>Arg<br>Gly | 6156<br>GAG<br>GLu<br>Arg<br>Glu |
| AAC<br>Asn<br>Thr<br>Arg | GTT<br>Val<br>Leu<br>. | GAA<br>Glu<br>Asn<br>Thr | CTC<br>Leu<br>Ser<br>Leu | TCC<br>Ser<br>Pro<br>Pro | CCT<br>Pro<br>Leu<br>Tyr | ACC<br>Thr<br>Pro<br>His | ACT<br>Thr<br>Leu<br>Trp | 6183<br>GGC<br>Gly<br>Ala<br>Pro | CAC<br>His<br>Thr<br>Leu | TGT<br>Cys<br>Val<br>. | AAC<br>Asn<br>Thr<br>Gln | AGT<br>Ser<br>Val<br>Trp | GGA<br>Gly<br>Asp<br>Thr | CGA<br>Arg<br>Glu<br>Asn | ACT<br>Thr<br>Leu<br>Ser | CGC<br>Arg<br>Ala<br>Pro | 6210<br>CAC<br>His<br>Thr<br>Arg |

TABLE 2-continued

| | | | | | | | | | | | | | | | | | |
|---|---|---|---|---|---|---|---|---|---|---|---|---|---|---|---|---|---|
| | | | | | | | | 6237 | | | | | | | | | 6264 |
| GGA | TCC | GCA | AGC | CAA | GTG | CAG | AAG | CAA | AGA | AGC | GCT | GGC | AGT | TTC | AAA | CGT | AAT |
| Gly | Ser | Ala | Ser | Gln | Val | Gln | Lys | Gln | Arg | Ser | Ala | Gly | Ser | Phe | Lys | Arg | Asn |
| Asp | Pro | Gln | Ala | Lys | Cys | Arg | Ser | Lys | Glu | Ala | Leu | Ala | Val | Ser | Asn | Val | Ile |
| Ile | Arg | Lys | Pro | Ser | Ala | Glu | Ala | Lys | Lys | Arg | Trp | Gln | Phe | Gln | Thr | . | . |
| | | | | | | | | 6291 | | | | | | | | | 6318 |
| AGC | ATT | AAG | AAG | ATC | GTG | TGA | AGC | TTG | CTT | GCT | TTC | TTT | TTT | AAA | ATC | AAC | TTA |
| Ser | Ile | Lys | Lys | Ile | Val | . | Ser | Leu | Leu | Ala | Phe | Phe | Phe | Lys | Ile | Asn | Leu |
| Ala | Leu | Arg | Arg | Ser | Cys | Glu | Ala | Cys | Leu | Leu | Ser | Phe | Leu | Lys | Ser | Thr | . |
| His | . | Glu | Asp | Arg | Val | .Lys | Leu | Ala | Cys | Phe | Leu | Phe | . | Asn | Gln | Leu | Asn |
| | | | | | | | | 6345 | | | | | | | | | 6372 |
| ACA | TGG | GCT | CTT | CAC | TAG | TGA | CCC | CTT | CCC | TGT | CCT | TGC | CCT | TTC | CCC | CCA | TGT |
| Thr | Trp | Ala | Leu | His | . | . | Pro | Leu | Pro | Cys | Pro | Cys | Pro | Phe | Pro | Pro | Cys |
| His | Gly | Leu | Phe | Thr | Ser | Asp | Pro | Phe | Pro | Val | Leu | Ala | Leu | Ser | Pro | His | Val |
| MET | Gly | Ser | Ser | Leu | Val | Thr | Pro | Ser | Leu | Ser | Leu | Pro | Phe | Pro | Pro | MET | Leu |
| | | | | | | | | 6399 | | | | | | | | | 6426 |
| TGT | AAT | GCT | GCA | CTT | CCT | GTT | TTA | TAA | TGA | ACC | CAT | CCG | GTT | TGC | CAT | GTT | GCC |
| Cys | Asn | Ala | Ala | Leu | Pro | Val | Leu | . | . | Thr | His | Pro | Val | Cys | His | Val | Ala |
| Val | MET | Leu | His | Phe | Leu | Phe | Tyr | Asn | Glu | Pro | Ile | Arg | Phe | Ala | MET | Leu | Pro |
| . | Cys | Cys | Thr | Ser | Cys | Phe | Ile | MET | Asn | Pro | Ser | Gly | Leu | Pro | Cys | Cys | Gln |
| | | | | | | | | 6453 | | | | | | | | | 6480 |
| AGA | TGA | TCA | ACT | CTT | CGA | AGC | CTT | GCC | TAA | ATT | TAA | TGC | TGC | CTT | TTC | TTT | AAC |
| Arg | . | Ser | Thr | Leu | Arg | Ser | Leu | Ala | . | Ile | . | Cys | Cys | Leu | Phe | Phe | Asn |
| Asp | Asp | Gln | Leu | Phe | Glu | Ala | Leu | Pro | Lys | Phe | Asn | Ala | Ala | Phe | Ser | Leu | Thr |
| MET | Ile | Asn | Ser | Ser | Lys | Pro | Cys | Leu | Asn | Leu | MET | Leu | Pro | Phe | Leu | . | Leu |
| | | | | | | | | 6507 | | | | | | | | | 6534 |
| TTT | TTT | TCT | TCT | ACT | TTT | GGC | GTG | TAT | CTG | GTA | TAT | GTA | AGT | GTT | CAG | AAC | AAC |
| Phe | Phe | Ser | Ser | Thr | Phe | Gly | Val | Tyr | Leu | Val | Tyr | Val | Ser | Val | Gln | Asn | Asn |
| Phe | Phe | Leu | Leu | Leu | Leu | Ala | Cys | Ile | Trp | Tyr | MET | . | Val | Phe | Arg | Thr | Thr |
| Phe | Phe | Phe | Tyr | Phe | Trp | Arg | Val | Ser | Gly | Ile | Cys | Lys | Cys | Ser | Glu | Gln | Leu |
| | | | | | | | | 6561 | | | | | | | | | |
| TGC | AAA | GAA | AGT | GGG | AGG | TCA | GGA | AAC | TTT | TAA | CTG | AGA | AAT | | | | |
| Cys | Lys | Glu | Ser | Gly | Arg | Ser | Gly | Asn | Phe | . | Leu | Arg | Asn | | | | |
| Ala | Lys | Lys | Val | Gly | Gly | Gln | Glu | Thr | Phe | Asn | . | Glu | | | | | |
| Gln | Arg | Lys | Trp | Glu | Val | Arg | Lys | Leu | Leu | Thr | Glu | Lys | | | | | |

EXAMPLE 8

Genomic DNA Sequences

Genomic DNA sequences come primarily from a new method of multiplex sequencing which was applied to the cosmid cEVI20 and to the 3.8 kb EcoRI fragment harboring the t(17;22) breakpoint. Gaps between sequence contigs were filled in by primer walking or, in a few cases, by asymmetric PCR amplification and sequencing of 13 subclones. The entire sequence of the 3.8 kb EcoRI fragment has been obtained as has the entire sequence of the 9 kb EcoRI fragment containing the EVI2 gene. The open reading frame of the cDNA sequence and the intron-exon boundary sequences agree with the orientation of transcription as 5' to 3' in the centromeric to telomeric direction.

EXAMPLE 9

Structure of the NF1 Gene

Detailed mapping of exons from the cDNAs was performed through sequence comparison between cDNAs and genomic DNA. FIG. 8 shows the sequences of the exons and their flanking intronic sequences for 50 bp on either side of the intron-exon boundaries. FIG. 8 also shows the locations of the exons on the restriction fragment map of the region surrounding the translocations. The most proximal (5') exon mapping to cloned genomic sequence, provisionally denoted as exon 1, lies in the 9 kb EcoRI fragment containing the 5' noncoding exon of EVI2. The EVI2 5' exon lies 4120 bp centromeric of exon 1, with an Alu repeat located midway between. Exon 1 is 433 bases long and the intron between exons 1 and 2 also contains an Alu repeat. Exon 2 is also completely within the 9 kb EcoRI fragment. Exon 3 maps to the 1.7 kb EcoRI fragment shown previously to be deleted in a 11 kb NF1 deletion mutation. Exons—9 map to the 3.8 kb EcoRI fragment spanning the translocation breakpoint. The intron between exons 4 and 5 contains the t(17;22) breakpoint. The 22 bp of cDNA sequence extending 5' from exon 1 is not found in the 9 kb fragment, indicating that the TBR gene extends centromeric of this fragment.

EXAMPLE 10

Identification of Nucleotide Alterations in NF1 Patients

SSCP is a rapid and sensitive assay for nucleotide alterations, including point mutations (15,16). DNA segments 100 bp–400 bp in length are amplified by PCR, heat denatured and electrophoresed on high resolution, non-denaturing acrylamide gels. Under these conditions each single-stranded DNA fragment assumes a secondary structure determined in part by its nucleotide sequence. Several examples of single base changes significantly affecting the electrophoretic mobility of the PCR product have been reported (16,42).

Five pairs of oligonucleotide primers were used to screen exons 4–9 of the TBR gene. The sequences of the primers are given in Table 1 above. Primer pairs A–D specifically amplify each of exons 4 through 7, along with some flanking intron sequences. Primer pair E amplifies a single 1.3 kb genomic segment, containing exons 7, 8 and 9. After amplification, the products of E-primed PCR were digested with a combination of the restriction enzymes RsaI and XbaI to yield fragments in a size range amenable to SSCP analysis. One of the resulting fragments contains exon 7 and another fragment contains exons 8 and 9.

Each primer pair was used to amplify specific DNA segments from 72 NF1 patients and 60–65 non-NF1 controls. After PCR, the products of the reaction were initially examined by agarose gel electrophoresis and ethidium-bromide staining. In all samples with visible product, a single band of appropriate size was seen, and no differences were detected between NF1 individuals and non-NF1 controls.

Figure 9F:
FIG. 9 shows SSCP variants specific to NF1 patients. The middle lanes of the six panels show unusual SSCP alleles that were found in NF1 individuals. The two flanking lanes in each panel show alleles with mobilities that were shared by all the non-NF1 samples as well as most of the NF1 samples. The PCR product analyzed in (a), (b), and (c) spans exon 4 of the new NF1 candidate gene. The PCR product in (d) contains exon 5; the product in (e) contains both exon 8 and 9; and the product in (f) contains exon 7. The patients with aberrant alleles are patient 11423 (a); patient 11476 (b); patient 11528 (c); patient 11389 (d); patient 11578 (e); and patient 11572 (f).
Figure 9E:
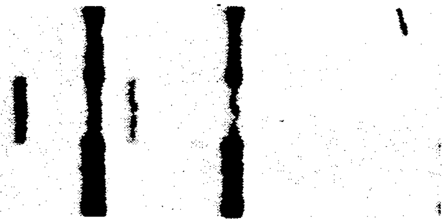
Figure 9D:
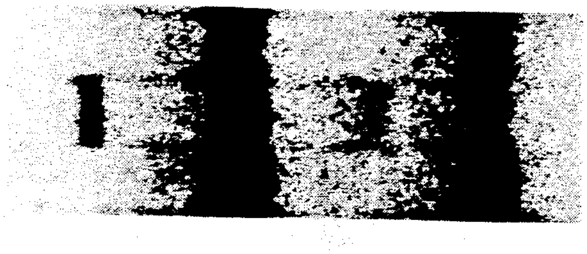
Figure 9C:
Figure 9B:
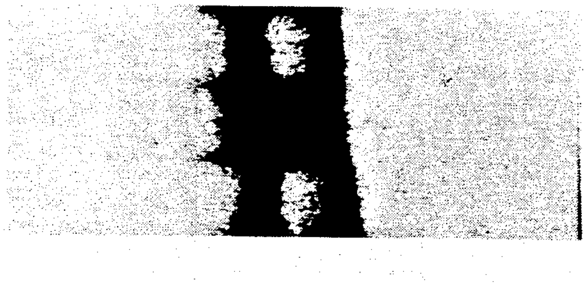
Figure 9A:
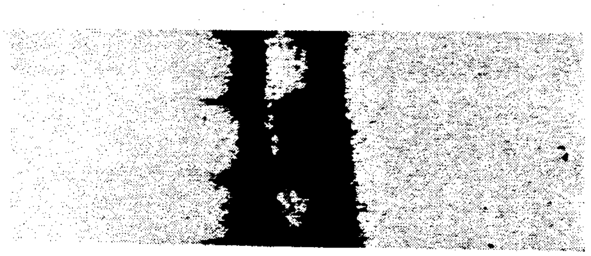

However, upon subjecting these PCR products to SSCP analysis (FIG. 9), six alleles specific to NF1 individuals were found. Several patterns can occur when heterozygotes are detected by SSCP analysis. The simplest pattern is that of FIG. 9*e*. The homozygous samples in the first and third lanes have only two bands, representing the two complementary single strands of DNA. The heterozygote in the middle lane has two additional bands corresponding to the two strands of the new allele. In FIG. 9*f*, only three distinct bands are seen in the heterozygote; one strand of the new allele is able to assume a novel conformation with a different electrophoretic mobility, but the other strand, although it has experienced the complementary sequence change, has no new conformation available to it, and so continues to migrate with the corresponding strand of the normal allele. As expected, the aberrant band and one of the bands from the normal allele are of equal intensity, and each of these is approximately half the intensity of the third band. In FIG. 9*c* it appears that both strands of the new allele migrate together; apparently under these gel conditions they have not been resolved. This interpretation is supported by the greater intensity of the new band in comparison to the bands of the normal allele. It is known that this band does not represent reannealed double-stranded DNA, because the non-denatured sample has a different mobility.

Three of the variants were found in the segment containing exon 4, one was in the segment containing exon 5, one was in the segment spanning exon 7, and one was in an RsaI restriction fragment containing exons 8 and 9. No two individuals shared any one of the six variant alleles and no variant allele was observed in the control samples. The six alleles were found in four familial cases and in two sporadic cases of NF1. The entire PCR-SSCP procedure was repeated on the DNA samples in which the variant alleles were detected and on several control samples. All six variant SSCP bands were reproducible.

The most likely explanation for these results is that at least some of these NF1 individuals carry a DNA sequence change within the amplified DNA segment that causes NF1. However, the null hypothesis that all six alleles might actually represent DNA polymorphisms not associated with NF1 should also be considered. Assuming the null hypothesis, the probability that none of the six alleles would be found upon screening the non-NF1 individuals can be calculated. When a one-sided test of heterogeneity is performed using Fisher's exact test, the frequency of observed variants is significantly greater in NF1 patients than in controls at a nominal level of 0.05.

Figure 10:
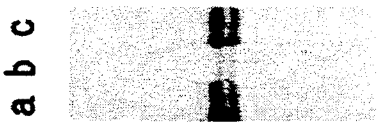
FIG. 10 shows the coinheritance of an SSCP variant and NF1 in the family of patient 11423. Lane (a) contains the sample from patient 11423; lane (b) is the sample from the unaffected spouse of patient 11423; and lane c received the sample from the NF1-affected child of this couple. (The patterns observed are different from those seen in FIG. 9(*a*), because the gels were run under different conditions. See Example 1.)

Genomic DNA samples from the unaffected spouse and affected child of patient 11423 were available. As shown in FIG. 10, SSCP analysis revealed that the unusual allele originally detected in the father is inherited by his NF1 -affected son. The NF1 father, lane a, and NF1 child, lane c, show identical SSCP patterns consisting of four bands appearing as two doublets. The unaffected mother has just the lower band of the upper doublet and the upper band of the lower doublet. The differences in intensity of bands from one lane to another are due to differences in amount of PCR product amplified and loaded on the gel. This experiment confirms that the sequence variant that gives rise to the variant SSCP allele is carried by the sam chromosome 17 that carries the NF1 mutation.

EXAMPLE 11

Nucleotide Sequences of Variant Alleles Detected by SSCP Analysis

To determine the nucleotide changes responsible for the altered electrophoretic mobilities of the variant bands, several of the associated PCR products were sequenced. The band of altered mobility was cut from the dried SSCP acrylamide gel, DNA eluted from the gel slice, reamplified and sequenced on an Applied Biosystems Model 373A automated sequencer. Sequencing of the altered SSCP allele of exon 4 from patient 11423 (the allele shown to be inherited along with the NF1 mutation in the family) revealed that it contains a T→C transition at base 1045 of the cDNA sequence (FIG. 7), changing a leucine residue to a proline residue in the predicted peptide. Sequencing of the altered SSCP allele derived from the same exon from patient 11528 revealed a C→T transition at base 1087 of the cDNA sequence, changing an arginine residue to a stop codon. For each of these mutations, sequencing was performed on both strands of the PCR products, with complete agreement.

SUMMARY

These results confirm that the TBR gene is the gene for neurofibromatosis type 1. Six base pair variants were revealed among 72 NF1 patient DNAs. A set of from 60 to 65 control, unaffected individuals showed no variant bands. The likelihood of this observation occurring due to chance if the six variants were population polymorphisms unrelated to NF1 is less than 0.05. This provides good support for the hypothesis that at least some of these base pair change variants are, in fact, NF1 mutations in the TBR gene.

Furthermore, at least some of the base pair change variants should have a major impact on the amino acid sequence of the gene product. Sequence data from two of the variant bands indicate a nucleotide substitution within exon 4. The predicted amino acid change in one case results in a leucine to proline substitution. Demonstration of the transmission of this variant band from the affected parent to the affected child confirmed that it reflected the NF1 mutant allele. The other case was even more dramatic; the nucleotide substitution creates an in-frame stop codon, truncating the protein at this point. These NF1 point mutations, unlike the deletions and translocation previously shown to interrupt the TBR gene, are unlikely to have a regulatory impact on other genes in the region and thus uniquely identify the TBR gene as the NF1 gene.

Each of the mutant alleles described herein, is expected to inactivate the NF1 gene. The dominant inheritance of NF1 raises the intriguing question of how a mutation that inactivates the gene product results in a dominant allele. One possibility, is simply that there is a gene dosage effect and that cells with only 50% activity of the NF1 gene become vulnerable to secondary mutations at other loci resulting in growth deregulation.

A more interesting hypothesis, by analogy with retinoblastoma, is that the mutant NF1 allele might be a recessive at the level of the cell (43). The phenotype, the emergence of a neoplastic clone of cells, would result from the loss or inactivation of the normal allele in the progenitor of the cell clone. In the case of retinoblastoma, loss of function of the normal allele occurs most frequently through a loss of the chromosome, or a major segment of the chromosome, carrying the normal allele, presumably as a nondisjunctional event at mitosis. Loss of chromosome 17 is seen in malignant Schwannomas from NF1 patients (neurofibromas are not amenable to such studies as they consist of cell mixtures); however, the interpretation is complicated by the fact that p53, a known recessive oncogene, is located on 17*p*, the short arm of chromosome 17. The loss of the entire chromosome, therefore, can be interpreted as due to the presence of a mutated p53 gene. The only informative losses are those where only one arm of the chromosome is lost. Although most often partial chromosome loss is only of 17*p* (11), loss of chromosome 17*q* (the NF1 gene is on 17*q*) has been reported in only two cases (44). There seem to be relatively few NF1 -specific chromosome losses associated with the malignancies.

The high frequency of new mutation seen in the NF1 gene, however, suggests that loss of the normal allele through somatic mutation might occur much more frequently than mitotic nondisjunctions. If that were the case, then an appreciable increase in loss of 17*q* in NF1 tumors would not be expected and could maintain the cell recessive hypothesis. This model makes the strong prediction, that two mutant NF1 alleles, a new somatic mutation in addition to the inherited mutation, will often be found in NF1 malignant Schwannomas.

The suggestion that the NF1 gene spans, in opposing orientation, at least three active genes within a major intron raises the intriguing possibility that some mutations in this region may have several effects, impacting two or more genes jointly. Is it possible to simultaneously transcribe nested genes in opposite orientation? If not, then activation of any of the three genes within the intron, EVI2. RC1 or OMGP, might inhibit transcription of the NF1 gene. Careful examination of patient phenotypes in NF1 deletion cases might be revealing. EVI2. OMGP and NF1 are each transcribed in brain and EVI2, RC1 and NF1 are known to be present in peripheral blood.

The learning disabilities of some NF1 cases could be explained by removal or inactivation of either the EVI2 or OMGP genes. Alteration of the OMGP gene is an especially intriguing possibility due to its known role in oligodendrocytes as an externally located, cell adhesion molecule potentially active in mediating proper cell mobility and differentiation during brain development (45). Similarly, the higher frequency of juvenile chronic myelogenous leukemias that have been found among NF1 patients (46–48) might be related to NF1 mutations that jointly disrupt EVI2 or RC1. The imbedded genes provide even more motivation than usual for clinical correlations of specific mutations with phenotypic characteristics.

The preliminary northern analysis suggests a message with an approximate length of 11 kb. Interestingly, the finding in a screen of only 1014 bp of exonic DNA that 6 out of approximately 70 patients yielded variant SSCP bands, of which two were confirmed as single base substitutions, suggests that the NF1 gene may have a large proportion of point mutations.

Only a specific section of the gene is, however, being scanned and it may be found that deletions are more abundant in other regions. For example, mapping of the cDNA sequence against genomic DNA sequences has revealed that the NF1 gene structure, for the 4 kb sequenced above, consists of a series of relatively small exons distributed over more than 110 kb of genomic DNA. Intriguingly, this distribution of small exons seems characteristic of very large genes as, for example, the Duchenne muscular dystrophy gene and the chromosome 18*q* gene found to be deleted in colon carcinomas. This raises the possibility that NF1 may also be distributed over a very large genomic region, which, if true may also be a large target for deletions and rearrangements not yet characterized.

A composite of (a) human fetal brain cDNA clones in bacteriophage λ (Stategene Zap) and (b) human genomic recombinant DNA cosmids were deposited at the American Type Culture Collection (ATCC), Rockville, Maryland, U.S.A. on Jul. 12, 1990 and assigned the numbers 40846 and 40845, respectively. The composite of cDNA clones comprises a composite of human neurofibromatosis type 1 gene cDNAs in Bacteriophage lambda. The composite of genomic cosmids comprises a composite of human neurofibromatosis type region cosmids, including cEVI37, cEVI36, cEVI20, cT315, cT316 and c7D5. These deposits were made under the provisions of the Budapest Treaty on the International Recognition of the Deposit of Microorganisms for the Purpose of Patent Procedure and the regulations thereunder (Budapest Treaty). This assures maintenance of a viable culture for 30 years from date of deposit. The deposits will be made available by ATCC under the terms of the Budapest Treaty, and subject to an agreement between Applicants and ATCC which assures permanent and unrestricted availability upon issuance of the pertinent U.S. patent. The Assignee herein agrees that if the culture on deposit should die or be lost or destroyed when cultivated under suitable conditions, it will be promptly replaced upon notification with a viable specimen of the same culture. Availability of the deposits is not to be construed as a license to practice the invention in contravention of the rights granted under the authority of any government in accordance with its patent laws.

These deposits were made for the convenience of the relevant public and do not constitute an admission that a written description would not be sufficient to permit practice of the invention or an intention to limit the invention to these specific constructs. Set forth hereinabove is a complete written description enabling a practitioner of ordinary skill to duplicate the constructs deposited and to construct alternative forms of DNA, or organisms containing it, which permit practice of the invention as claimed.

While the invention has been disclosed in this patent application by reference to the details of preferred embodiments of the invention, it is to be understood that this disclosure is intended in an illustrative rather than in a limiting sense, as it is contemplated that modifications will readily occur to those skilled in the art, within the spirit of the invention and the scope of the appended claims.

Bibliography (1) Stumpf, D. A., et al. (1988). *Arch. Neurol.* 45: 575–578.

(2) Ricardi, V. M. and Lewis, R. A. (1988). *Am. J. Hum. Genet.* 42: 284–289.

(3) Barker, D., et al. (1987). *Science* 236: 1100–1102.

(4) Seizinger, B. R., et al. (1987). *Cell* 49: 589–594.

(5) Goldgar, D. E., et al. (1989). *Am. J. Hum. Genet.* 44: 6–12.

(6) O'Connell, P., et al. (1989). *Am. J. Hum. Genet.* 44: 51–57.

(7) Ledbetter, D. H., et al. (1989). *Am. J. Hum. Genet.* 44: 20–24.

(8) Fountain, J. W., et al. (1989). *Am. J. Hum. Genet* 44: 58–67.

(9) Schmidt, M. A., et al. (1987). *Am. J. Med. Genet* 28: 771–777.

(10) O'Connell, P., et al. (1989). *Science* 244: 1087–1088.

(11) Menon, A. G., et al. (1989). *Genomics* 5: 245–249.

(12) Maniatis, T., et al. (1982). *Molecular Cloning: A Laboratory Manual,* Cold Spring Harbor Laboratory, Cold Spring Harbor, N.Y.

(13) Sambrook, J., et al. (1989). *Molecular Cloning: A Laboratory Manual,* 2nd Ed., Cold Spring Harbor Laboratory, Cold Spring Harbor, N.Y.

(14) Meth. Enzymol., Vol. 68, 100, 101, 152–155, Academic Press, Orlando (1979, 1983, 1987).

(15) Orita, M., et al. (1989). *Proc. Natl. Acad. Sci. U.S.A.* 86: 2766–2770.

(16) Orita, M., et al. (1988). *Genomics* 5: 874–879.

(17) Meth. Enzymol., Vol. 121, Langone, J. J. and Van Vunakis, H., Ed., Academic Press, Orlando (1986).

(17*a*) Roitt, I., in *Essential Immunology,* 5th Ed. Blackwell Scientific Publications, Boston, pp. 145–175 (1984).

(18) Lathrop, G. M., et al. (1985). *Am. J. Hum. Genet.* 37: 482–498.

(19) Seed, B., et al. (1982). *Gene* 19: 201–299.

(20) Benton, W. D., and Davis, R. W. (1977). *Science* 196: 180–182.

(21) Grunstein, M. and Hogness, D. (1975). *Proc. Natl. Acad. Sci. U.S.A.* 72: 3961–3965.

(22) Schwartz, D. C. and Cantor, C. R. (1984). *Cell* 37: 67–75.

(23) Gardiner, K., et al. (1986). Som. Cell. Mol. Genet 12: 185–195.

(24) Feinberg, A. and Vogelstein, B. (1984). *Anal. Biochem.* 137: 266–267.

(25) Friedman, K. D., et al. (1988). *Nucl. Acid Res.* 16: 8718.

(26) Chomczynski, P. and Sacchi, N. (1987). *Anal. Biochem.* 162: 156–159.

(27) Selden, R. F., in *Current Protocols in Molecular Biology.* John Wiley & Sons, New York, pp 4.9.1–4.9.8 (1989).

(28) Sanger, F., et al. (1977). *Proc. Natl. Acad. Sci. U.S.A.* 74: 5463–5467.

(29) Birnboim, H. C. (1983). *Meth. Enzymol.* 100: 243–255.

(30) Church, G. and Kieffer-Higgins, S. (1988). *Science* 240: 185–188.

(31) Pearson, W. R. and Lipman, D. J. (1987). *Proc. Natl. Acad. Sci. U.S.A.* 85: 2444–2448.

(32) Devereux, J., et al. (1984). *Nucl. Acids Res.* 12: 387–395.

(33) Nakamura, Y., et al. (1988). *Genomics* 2: 302.

(34) Killary, A. M. and Fournier, R. E. K. (1974). *Cell* 38: 523.
(35) Lugo, T. G., et al. (1987). *Mol. Cell. Biol.* 7: 2814.
(36) Leach, R. J., et al. (). *Genomics.*
(37) Van Tuinen, P., et al. (1987). *Genomics* 1: 374.
(38) Julier, C. and White, R. (1988). *Am. J. Hum. Genet.* 42: 45.
(39) Bird, A. P. (1986). Nature 321: 209–213.
(40) Frohman, M. A., et al. (1988). *Proc. Natl. Acad. Sci. U.S.A.* 85: 8998–9002.
(41) Loh, E. Y. et al. (1989). Science 243: 217–220.
(42) Dean, M. et al. (1990). Cell 61: 863–870.
(43) Cavenee, W. K. et al. (1983). *Nature* 305: 779–784.
(44) Skuse, G. R. et al. (1989). Cancer 1: 36–41.
(45) Mikol, D. D. et al. (1990). *J. Cell. Biol.* 110: 471–480.
(46) Bader, J. L. and Miller, R. W. (1978). *J. Pediatr.* 92: 925–929.
(47) Mays, J. A. et al (1980). *Am. J. Dis. Child* 13: 654–658.
(48) Clark, R. D. and Hutter, J. J. (1982). Hum. Genet. 60: 230–232.
(49) Pouwels, P. H. et al., Cloning Vectors: A Laboratory Manual. Elsevier, Amsterdam (1987).
(50) U.S. Pat. No. 4711,845
(51) Cruz and Patterson, *Tissue Culture.* Academic Press, Orlando (1973).
(52) *Meth. Enzymol.* Vol 58, Academic Press, Orlando (1979).
(53) Freshney, R. I., *Culture of Animals Cells: A Manual of Basic Technique,* 2nd Ed., Alan R. Liss, New York (1987).
(54) U.S. Pat. No. 4,399,216.
(55) *Meth. Enzymol,* Vol 118, Academic Press, Orlando (1986).
(56) Gelvin, S. B. et al, *Plant Molecular Biology Manual,* Kluwer Academic Publishers, Dudrecht (1990).
(57) Melton, et al., (1984), *Nucl. Acids Res.* 12: 7035.
(58) Myers et al. (1985), *Science* 230: 1242–1246.
(59) Erlich, H. A. *PCR Technology,* Stockton Press, New York (1989).
(60) Innis, M. A. et al., *PCR Protocols,* Academic Press, San Diego (1980).

What is claimed is:

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 6060 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
( A ) ORGANISM: Homo sapiens ( i x ) FEATURE:
( A ) NAME/KEY: CDS
( B ) LOCATION: 1..6060

( x i ) SEQUENCE DESCRIPTION: SEQ ID NO:1:

| | | | | | | | | | | | | | | | | |
|---|---|---|---|---|---|---|---|---|---|---|---|---|---|---|---|---|
| ATG | GAA | GAT | GGC | CAG | GCT | GCT | GAA | AGC | CTT | CAC | AAG | ACC | ATT | GTT | AAG | 48 |
| Met | Glu | Asp | Gly | Gln | Ala | Ala | Glu | Ser | Leu | His | Lys | Thr | Ile | Val | Lys | |
| 1 | | | | 5 | | | | | 10 | | | | | 15 | | |
| AGG | CGA | ATG | TCC | CAT | GTG | AGT | GGA | GGA | GGA | TCC | ATA | GAT | TTG | TCT | GAC | 96 |
| Arg | Arg | Met | Ser | His | Val | Ser | Gly | Gly | Gly | Ser | Ile | Asp | Leu | Ser | Asp | |
| | | | 20 | | | | | 25 | | | | | 30 | | | |
| ACA | GAC | TCC | CTA | CAG | GAA | TGG | ATC | AAC | ATG | ACT | GGC | TTC | CTT | TGT | GCC | 144 |
| Thr | Asp | Ser | Leu | Gln | Glu | Trp | Ile | Asn | Met | Thr | Gly | Phe | Leu | Cys | Ala | |
| | | 35 | | | | | 40 | | | | | 45 | | | | |
| CTT | GGA | GGA | GTG | TGC | CTC | CAG | CAG | AGA | AGC | AAT | TCT | GGC | CTG | GCA | ACC | 192 |
| Leu | Gly | Gly | Val | Cys | Leu | Gln | Gln | Arg | Ser | Asn | Ser | Gly | Leu | Ala | Thr | |
| | 50 | | | | | 55 | | | | | 60 | | | | | |
| TAT | AGC | CCA | CCC | ATG | GGT | CCA | GTC | AGT | GAA | CGT | AAG | GGT | TCT | ATG | ATT | 240 |
| Tyr | Ser | Pro | Pro | Met | Gly | Pro | Val | Ser | Glu | Arg | Lys | Gly | Ser | Met | Ile | |
| 65 | | | | | 70 | | | | | 75 | | | | | 80 | |
| TCA | GTG | ATG | TCT | TCA | GAG | GGA | AAC | GCA | GAT | ACA | CCT | GTC | AGC | AAA | TTT | 288 |
| Ser | Val | Met | Ser | Ser | Glu | Gly | Asn | Ala | Asp | Thr | Pro | Val | Ser | Lys | Phe | |
| | | | | 85 | | | | | 90 | | | | | 95 | | |

-continued

```
ATG GAT CGG CTG TTG TCC TTA ATG GTG TGT AAC CAT GAG AAA GTG GGA     336
Met Asp Arg Leu Leu Ser Leu Met Val Cys Asn His Glu Lys Val Gly
            100                 105                 110

CTT CAA ATA CGG ACC AAT GTT AAG GAT CTG GTG GGT CTA GAA TTG AGT     384
Leu Gln Ile Arg Thr Asn Val Lys Asp Leu Val Gly Leu Glu Leu Ser
        115                 120                 125

CCT GCT CTG TAT CCA ATG CTA TTT AAC AAA TTG AAG AAT ACC ATC AGC     432
Pro Ala Leu Tyr Pro Met Leu Phe Asn Lys Leu Lys Asn Thr Ile Ser
    130                 135                 140

AAG TTT TTT GAC TCC CAA GGA CAG GTT TTA TTG ACT GAT ACC AAT ACT     480
Lys Phe Phe Asp Ser Gln Gly Gln Val Leu Leu Thr Asp Thr Asn Thr
145                 150                 155                 160

CAA TTT GTA GAA CAA ACC ATA GCT ATA ATG AAG AAC TTG CTA GAT AAT     528
Gln Phe Val Glu Gln Thr Ile Ala Ile Met Lys Asn Leu Leu Asp Asn
                165                 170                 175

CAT ACT GAA GGC AGC TCT GAA CAT CTA GGG CAA GCT AGC ATT GAA ACA     576
His Thr Glu Gly Ser Ser Glu His Leu Gly Gln Ala Ser Ile Glu Thr
            180                 185                 190

ATG ATG TTA AAT CTG GTC AGG TAT GTT CGT GTG CTT GGG AAT ATG GTC     624
Met Met Leu Asn Leu Val Arg Tyr Val Arg Val Leu Gly Asn Met Val
        195                 200                 205

CAT GCA ATT CAA ATA AAA ACG AAA CTG TGT CAA TTA GTT GAA GTA ATG     672
His Ala Ile Gln Ile Lys Thr Lys Leu Cys Gln Leu Val Glu Val Met
    210                 215                 220

ATG GCA AGG AGA GAT GAC CTC TCA TTT TGC CAA GAG ATG AAA TTT AGG     720
Met Ala Arg Arg Asp Asp Leu Ser Phe Cys Gln Glu Met Lys Phe Arg
225                 230                 235                 240

AAT AAG ATG GTA GAA TAC CTG ACA GAC TGG GTT ATG GGA ACA TCA AAC     768
Asn Lys Met Val Glu Tyr Leu Thr Asp Trp Val Met Gly Thr Ser Asn
                245                 250                 255

CAA GCA GCA GAT GAT GAT GTA AAA TGT CTT ACA AGA GAT TTG GAC CAG     816
Gln Ala Ala Asp Asp Asp Val Lys Cys Leu Thr Arg Asp Leu Asp Gln
            260                 265                 270

GCA AGC ATG GAA GCA GTA GTT TCA CTT CTA GCT GGT CTC CCT CTG CAG     864
Ala Ser Met Glu Ala Val Val Ser Leu Leu Ala Gly Leu Pro Leu Gln
        275                 280                 285

CCT GAA GAA GGA GAT GGT GTG GAA TTG ATG GAA GCC AAA TCA CAG TTA     912
Pro Glu Glu Gly Asp Gly Val Glu Leu Met Glu Ala Lys Ser Gln Leu
    290                 295                 300

TTT CTT AAA TAC TTC ACA TTA TTT ATG AAC CTT TTG AAT GAC TGC AGT     960
Phe Leu Lys Tyr Phe Thr Leu Phe Met Asn Leu Leu Asn Asp Cys Ser
305                 310                 315                 320

GAA GTT GAA GAT GAA AGT GCG CAA ACA GGT GGC AGG AAA CGT GGC ATG    1008
Glu Val Glu Asp Glu Ser Ala Gln Thr Gly Gly Arg Lys Arg Gly Met
                325                 330                 335

TCT CGG AGG CTG GCA TCA CTG AGG CAC TGT ACG GTC CTT GCA ATG TCA    1056
Ser Arg Arg Leu Ala Ser Leu Arg His Cys Thr Val Leu Ala Met Ser
            340                 345                 350

AAC TTA CTC AAT GCC AAC GTA GAC AGT GGT CTC ATG CAC TCC ATA GGC    1104
Asn Leu Leu Asn Ala Asn Val Asp Ser Gly Leu Met His Ser Ile Gly
        355                 360                 365

TTA GGT TAC CAC AAG GAT CTC CAG ACA AGA GCT ACA TTT ATG GAA GTT    1152
Leu Gly Tyr His Lys Asp Leu Gln Thr Arg Ala Thr Phe Met Glu Val
    370                 375                 380

CTG ACA AAA ATC CTT CAA CAA GGC ACA GAA TTT GAC ACA CTT GCA GAA    1200
Leu Thr Lys Ile Leu Gln Gln Gly Thr Glu Phe Asp Thr Leu Ala Glu
385                 390                 395                 400

ACA GTA TTG GCT GAT CGG TTT GAG AGA TTG GTG GAA CTG GTC ACA ATG    1248
Thr Val Leu Ala Asp Arg Phe Glu Arg Leu Val Glu Leu Val Thr Met
                405                 410                 415

ATG GGT GAT CAA GGA GAA CTC CCT ATA GCG ATG GCT CTG GCC AAT GTG    1296
Met Gly Asp Gln Gly Glu Leu Pro Ile Ala Met Ala Leu Ala Asn Val
```

-continued 420 425 430

GTT CCT TGT TCT CAG TGG GAT GAA CTA GCT CGA GTT CTG GTT ACT CTG 1344
Val Pro Cys Ser Gln Trp Asp Glu Leu Ala Arg Val Leu Val Thr Leu
435 440 445

TTT GAT TCT CGG CAT TTA CTC TAC CAA CTG CTC TGG AAC ATG TTT TCT 1392
Phe Asp Ser Arg His Leu Leu Tyr Gln Leu Leu Trp Asn Met Phe Ser
450 455 460

AAA GAA GTA GAA TTG GCA GAC TCC ATG CAG ACT CTC TTC CGA GGC AAC 1440
Lys Glu Val Glu Leu Ala Asp Ser Met Gln Thr Leu Phe Arg Gly Asn
465 470 475 480

AGC TTG GCC AGT AAA ATA ATG ACA TTC TGT TTC AAG GTA TAT GGT GCT 1488
Ser Leu Ala Ser Lys Ile Met Thr Phe Cys Phe Lys Val Tyr Gly Ala
485 490 495

ACC TAT CTA CAA AAA CTC CTG GAT CCT TTA TTA CGA ATT GTG ATC ACA 1536
Thr Tyr Leu Gln Lys Leu Leu Asp Pro Leu Leu Arg Ile Val Ile Thr
500 505 510

TCC TCT GAT TGG CAA CAT GTT AGC TTT GAA GTG GAT CCT ACC AGG TTA 1584
Ser Ser Asp Trp Gln His Val Ser Phe Glu Val Asp Pro Thr Arg Leu
515 520 525

GAA CCA TCA GAG AGC CTT GAG GAA AAC CAG CGG AAC CTC CTT CAG ATG 1632
Glu Pro Ser Glu Ser Leu Glu Glu Asn Gln Arg Asn Leu Leu Gln Met
530 535 540

ACT GAA AAG TTC TTC CAT GCC ATC ATC AGT TCC TCC TCA GAA TTC CCC 1680
Thr Glu Lys Phe Phe His Ala Ile Ile Ser Ser Ser Ser Glu Phe Pro
545 550 555 560

CCT CAA CTT CGA AGT GTG TGC CAC TGT TTA TAC CAG GTG GTT AGC CAG 1728
Pro Gln Leu Arg Ser Val Cys His Cys Leu Tyr Gln Val Val Ser Gln
565 570 575

CGT TTC CCT CAG AAC AGC ATC GGT GCA GTA GGA AGT GCC ATG TTC CTC 1776
Arg Phe Pro Gln Asn Ser Ile Gly Ala Val Gly Ser Ala Met Phe Leu
580 585 590

AGA TTT ATC AAT CCT GCC ATT GTC TCA CCG TAT GAA GCA GGG ATT TTA 1824
Arg Phe Ile Asn Pro Ala Ile Val Ser Pro Tyr Glu Ala Gly Ile Leu
595 600 605

GAT AAA AAG CCA CCA CCT AGA ATC GAA AGG GGC TTG AAG TTA ATG TCA 1872
Asp Lys Lys Pro Pro Pro Arg Ile Glu Arg Gly Leu Lys Leu Met Ser
610 615 620

AAG ATA CTT CAG AGT ATT GCC AAT CAT GTT CTC TTC ACA AAA GAA GAA 1920
Lys Ile Leu Gln Ser Ile Ala Asn His Val Leu Phe Thr Lys Glu Glu
625 630 635 640

CAT ATG CGG CCT TTC AAT GAT TTT GTG AAA AGC AAC TTT GAT GCA GCA 1968
His Met Arg Pro Phe Asn Asp Phe Val Lys Ser Asn Phe Asp Ala Ala
645 650 655

CGC AGG TTT TTC CTT GAT ATA GCA TCT GAT TGT CCT ACA AGT GAT GCA 2016
Arg Arg Phe Phe Leu Asp Ile Ala Ser Asp Cys Pro Thr Ser Asp Ala
660 665 670

GTA AAT CAT AGT CTT TCC TTC ATA AGT GAC GGC AAT GTG CTT GCT TTA 2064
Val Asn His Ser Leu Ser Phe Ile Ser Asp Gly Asn Val Leu Ala Leu
675 680 685

CAT CGT CTA CTC TGG AAC AAT CAG GAG AAA ATT GGG CAG TAT CTT TCC 2112
His Arg Leu Leu Trp Asn Asn Gln Glu Lys Ile Gly Gln Tyr Leu Ser
690 695 700

AGC AAC AGG GAT CAT AAA GCT GTT GGA AGA CGA CCT TTT GAT AAG ATG 2160
Ser Asn Arg Asp His Lys Ala Val Gly Arg Arg Pro Phe Asp Lys Met
705 710 715 720

GCA ACA CTT CTT GCA TAC CTG GGT CCT CCA GAG CAC AAA CCT GTG GCA 2208
Ala Thr Leu Leu Ala Tyr Leu Gly Pro Pro Glu His Lys Pro Val Ala
725 730 735

GAT ACA CAC TGG TCC AGC CTT AAC CTT ACC AGT TCA AAG TTT GAG GAA 2256
Asp Thr His Trp Ser Ser Leu Asn Leu Thr Ser Ser Lys Phe Glu Glu
740 745 750

-continued

```
TTT ATG ACT AGG CAT CAG GTA CAT GAA AAA GAA GAA TTC AAG GCT TTG      2304
Phe Met Thr Arg His Gln Val His Glu Lys Glu Glu Phe Lys Ala Leu
        755                 760                 765

AAA ACG TTA AGT ATT TTC TAC CAA GCT GGG ACT TCC AAA GCT GGG AAT      2352
Lys Thr Leu Ser Ile Phe Tyr Gln Ala Gly Thr Ser Lys Ala Gly Asn
    770                 775                 780

CCT ATT TTT TAT TAT GTT GCA CGG AGG TTC AAA ACT GGT CAA ATC AAT      2400
Pro Ile Phe Tyr Tyr Val Ala Arg Arg Phe Lys Thr Gly Gln Ile Asn
785                 790                 795                 800

GGT GAT TTG CTG ATA TAC CAT GTC TTA CTG ACT TTA AAG CCA TAT TAT      2448
Gly Asp Leu Leu Ile Tyr His Val Leu Leu Thr Leu Lys Pro Tyr Tyr
                805                 810                 815

GCA AAG CCA TAT GAA ATT GTA GTG GAC CTT ACC CAT ACC GGG CCT AGC      2496
Ala Lys Pro Tyr Glu Ile Val Val Asp Leu Thr His Thr Gly Pro Ser
            820                 825                 830

AAT CGC TTT AAA ACA GAC TTT CTC TCT AAG TGG TTT GTT GTT TTT CCT      2544
Asn Arg Phe Lys Thr Asp Phe Leu Ser Lys Trp Phe Val Val Phe Pro
        835                 840                 845

GGC TTT GCT TAC GAC AAC GTC TCC GCA GTC TAT ATC TAT AAC TGT AAC      2592
Gly Phe Ala Tyr Asp Asn Val Ser Ala Val Tyr Ile Tyr Asn Cys Asn
    850                 855                 860

TCC TGG GTC AGG GAG TAC ACC AAG TAT CAT GAG CGG CTG CTG ACT GGC      2640
Ser Trp Val Arg Glu Tyr Thr Lys Tyr His Glu Arg Leu Leu Thr Gly
865                 870                 875                 880

CTC AAA GGT AGC AAA AGG CTT GTT TTC ATA GAC TGT CCT GGG AAA CTG      2688
Leu Lys Gly Ser Lys Arg Leu Val Phe Ile Asp Cys Pro Gly Lys Leu
                885                 890                 895

GCT GAG CAC ATA GAG CAT GAA CAA CAG AAA CTA CCT GCT GCC ACC TTG      2736
Ala Glu His Ile Glu His Glu Gln Gln Lys Leu Pro Ala Ala Thr Leu
            900                 905                 910

GCT TTA GAA GAG GAC CTG AAG GTA TTC CAC AAT GCT CTC AAG CTA GCT      2784
Ala Leu Glu Glu Asp Leu Lys Val Phe His Asn Ala Leu Lys Leu Ala
        915                 920                 925

CAC AAA GAC ACC AAA GTT TCT ATT AAA GTT GGT TCT ACT GCT GTC CAA      2832
His Lys Asp Thr Lys Val Ser Ile Lys Val Gly Ser Thr Ala Val Gln
    930                 935                 940

GTA ACT TCA GCA GAG CGA ACA AAA GTC CTA GGG CAA TCA GTC TTT CTA      2880
Val Thr Ser Ala Glu Arg Thr Lys Val Leu Gly Gln Ser Val Phe Leu
945                 950                 955                 960

AAT GAC ATT TAT TAT GCT TCG GAA ATT GAA GAA ATC TGC CTA GTA GAT      2928
Asn Asp Ile Tyr Tyr Ala Ser Glu Ile Glu Glu Ile Cys Leu Val Asp
                965                 970                 975

GAG AAC CAG TTC ACC TTA ACC ATT GCA AAC CAG GGC ACG CCG CTC ACC      2976
Glu Asn Gln Phe Thr Leu Thr Ile Ala Asn Gln Gly Thr Pro Leu Thr
            980                 985                 990

TTC ATG CAC CAG GAG TGT GAA GCC ATT GTC CAG TCT ATC ATT CAT ATC      3024
Phe Met His Gln Glu Cys Glu Ala Ile Val Gln Ser Ile Ile His Ile
        995                 1000                1005

CGG ACC CGC TGG GAA CTG TCA CAG CCC GAC TCT ATC CCC CAA CAC ACC      3072
Arg Thr Arg Trp Glu Leu Ser Gln Pro Asp Ser Ile Pro Gln His Thr
    1010                1015                1020

AAG ATT CGG CCA AAA GAT GTC CCT GGG ACA CTG CTC AAT ATC GCA TTA      3120
Lys Ile Arg Pro Lys Asp Val Pro Gly Thr Leu Leu Asn Ile Ala Leu
1025                1030                1035                1040

CTT AAT TTA GGC AGT TCT GAC CCG AGT TTA CGG TCA GCT GCC TAT AAT      3168
Leu Asn Leu Gly Ser Ser Asp Pro Ser Leu Arg Ser Ala Ala Tyr Asn
                1045                1050                1055

CTT CTG TGT GCC TTA ACT TGT ACC TTT AAT TTA AAA ATC GAG GGC CAG      3216
Leu Leu Cys Ala Leu Thr Cys Thr Phe Asn Leu Lys Ile Glu Gly Gln
            1060                1065                1070

TTA CTA GAG ACA TCA GGT TTA TGT ATC CCT GCC AAC AAC ACC CTC TTT      3264
Leu Leu Glu Thr Ser Gly Leu Cys Ile Pro Ala Asn Asn Thr Leu Phe
```

-continued 1075 1080 1085

ATT GTC TCT ATT AGT AAG ACA CTG GCA GCC AAT GAG CCA CAC CTC ACG 3312
Ile Val Ser Ile Ser Lys Thr Leu Ala Ala Asn Glu Pro His Leu Thr
1090 1095 1100

TTA GAA TTT TTG GAA GAG TGT ATT TCT GGA TTT AGC AAA TCT AGT ATT 3360
Leu Glu Phe Leu Glu Glu Cys Ile Ser Gly Phe Ser Lys Ser Ser Ile
1105 1110 1115 1120

GAA TTG AAA CAC CTT TGT TTG GAA TAC ATG ACT CCA TGG CTG TCA AAT 3408
Glu Leu Lys His Leu Cys Leu Glu Tyr Met Thr Pro Trp Leu Ser Asn
1125 1130 1135

CTA GTT CGT TTT TGC AAG CAT AAT GAT GAT GCC AAA CGA CAA AGA GTT 3456
Leu Val Arg Phe Cys Lys His Asn Asp Asp Ala Lys Arg Gln Arg Val
1140 1145 1150

ACT GCT ATT CTT GAC AAG CTG ATA ACA ATG ACC ATC AAT GAA AAA CAG 3504
Thr Ala Ile Leu Asp Lys Leu Ile Thr Met Thr Ile Asn Glu Lys Gln
1155 1160 1165

ATG TAC CCA TCT ATT CAA GCA AAA ATA TGG GGA AGC CTT GGG CAG ATT 3552
Met Tyr Pro Ser Ile Gln Ala Lys Ile Trp Gly Ser Leu Gly Gln Ile
1170 1175 1180

ACA GAT CTG CTT GAT GTT GTA CTA GAC AGT TTC ATC AAA ACC AGT GCA 3600
Thr Asp Leu Leu Asp Val Val Leu Asp Ser Phe Ile Lys Thr Ser Ala
1185 1190 1195 1200

ACA GGT GGC TTG GGA TCA ATA AAA GCT GAG GTG ATG GCA GAT ACT GCT 3648
Thr Gly Gly Leu Gly Ser Ile Lys Ala Glu Val Met Ala Asp Thr Ala
1205 1210 1215

GTA GCT TTG GCT TCT GGA AAT GTG AAA TTG GTT TCA AGC AAG GTT ATT 3696
Val Ala Leu Ala Ser Gly Asn Val Lys Leu Val Ser Ser Lys Val Ile
1220 1225 1230

GGA AGG ATG TGC AAA ATA ATT GAC AAG ACA TGC TTA TCT CCA ACT CCT 3744
Gly Arg Met Cys Lys Ile Ile Asp Lys Thr Cys Leu Ser Pro Thr Pro
1235 1240 1245

ACT TTA GAA CAA CAT CTT ATG TGG GAT GAT ATT GCT ATT TTA GCA CGC 3792
Thr Leu Glu Gln His Leu Met Trp Asp Asp Ile Ala Ile Leu Ala Arg
1250 1255 1260

TAC ATG CTG ATG CTG TCC TTC AAC AAT TCC CTT GAT GTG GCA GCT CAT 3840
Tyr Met Leu Met Leu Ser Phe Asn Asn Ser Leu Asp Val Ala Ala His
1265 1270 1275 1280

CTT CCC TAC CTC TTC CAC GTT GTT ACT TTC TTA GTA GCC ACA GGT CCG 3888
Leu Pro Tyr Leu Phe His Val Val Thr Phe Leu Val Ala Thr Gly Pro
1285 1290 1295

CTC TCC CTT AGA GCT TCC ACA CAT GGA CTG GTC ATT AAT ATC ATT CAC 3936
Leu Ser Leu Arg Ala Ser Thr His Gly Leu Val Ile Asn Ile Ile His
1300 1305 1310

TCT CTG TGT ACT TGT TCA CAG CTT CAT TTT AGT GAA GAG ACC AAG CAA 3984
Ser Leu Cys Thr Cys Ser Gln Leu His Phe Ser Glu Glu Thr Lys Gln
1315 1320 1325

GTT TTG AGA CTC AGT CTG ACA GAG TTC TCA TTA CCC AAA TTT TAC TTG 4032
Val Leu Arg Leu Ser Leu Thr Glu Phe Ser Leu Pro Lys Phe Tyr Leu
1330 1335 1340

CTG TTT GGC ATT AGC AAA GTC AAG TCA GCT GCT GTC ATT GCC TTC CGT 4080
Leu Phe Gly Ile Ser Lys Val Lys Ser Ala Ala Val Ile Ala Phe Arg
1345 1350 1355 1360

TCC AGT TAC CGG GAC AGG TCA TTC TCT CCT GGC TCC TAT GAG AGA GAG 4128
Ser Ser Tyr Arg Asp Arg Ser Phe Ser Pro Gly Ser Tyr Glu Arg Glu
1365 1370 1375

ACT TTT GCT TTG ACA TCC TTG GAA ACA GTC ACA GAA GCT TTG TTG GAG 4176
Thr Phe Ala Leu Thr Ser Leu Glu Thr Val Thr Glu Ala Leu Leu Glu
1380 1385 1390

ATC ATG GAG GCA TGC ATG AGA GAT ATT CCA ACG TGC AAG TGG CTG GAC 4224
Ile Met Glu Ala Cys Met Arg Asp Ile Pro Thr Cys Lys Trp Leu Asp
1395 1400 1405

-continued

CAG TGG ACA GAA CTA GCT CAA AGA TTT GCA TTC CAA TAT AAT CCA TCC 4272
Gln Trp Thr Glu Leu Ala Gln Arg Phe Ala Phe Gln Tyr Asn Pro Ser
1410 1415 1420

CTG CAA CCA AGA GCT CTT GTT GTC TTT GGG TGT ATT AGC AAA CGA GTG 4320
Leu Gln Pro Arg Ala Leu Val Val Phe Gly Cys Ile Ser Lys Arg Val
1425 1430 1435 1440

TCT CAT GGG CAG ATA AAG CAG ATA ATC CGT ATT CTT AGC AAG GCA CTT 4368
Ser His Gly Gln Ile Lys Gln Ile Ile Arg Ile Leu Ser Lys Ala Leu
1445 1450 1455

GAG AGT TGC TTA AAA GGA CCT GAC ACT TAC AAC AGT CAA GTT CTG ATA 4416
Glu Ser Cys Leu Lys Gly Pro Asp Thr Tyr Asn Ser Gln Val Leu Ile
1460 1465 1470

GAA GCT ACA GTA ATA GCA CTA ACC AAA TTA CAG CCA CTT CTT AAT AAG 4464
Glu Ala Thr Val Ile Ala Leu Thr Lys Leu Gln Pro Leu Leu Asn Lys
1475 1480 1485

GAC TCG CCT CTG CAC AAA GCC CTC TTT TGG GTA GCT GTG GCT GTG CTG 4512
Asp Ser Pro Leu His Lys Ala Leu Phe Trp Val Ala Val Ala Val Leu
1490 1495 1500

CAG CTT GAT GAG GTC AAC TTG TAT TCA GCA GGT ACC GCA CTT CTT GAA 4560
Gln Leu Asp Glu Val Asn Leu Tyr Ser Ala Gly Thr Ala Leu Leu Glu
1505 1510 1515 1520

CAA AAC CTG CAT ACT TTA GAT AGT CTC CGT ATA TTC AAT GAC AAG AGT 4608
Gln Asn Leu His Thr Leu Asp Ser Leu Arg Ile Phe Asn Asp Lys Ser
1525 1530 1535

CCA GAG GAA GTA TTT ATG GCA ATC CGG AAT CCT CTG GAG TGG CAC TGC 4656
Pro Glu Glu Val Phe Met Ala Ile Arg Asn Pro Leu Glu Trp His Cys
1540 1545 1550

AAG CAA ATG GAT CAT TTT GTT GGA CTC AAT TTC AAC TCT AAC TTT AAC 4704
Lys Gln Met Asp His Phe Val Gly Leu Asn Phe Asn Ser Asn Phe Asn
1555 1560 1565

TTT GCA TTG GTT GGA CAC CTT TTA AAA GGG TAC AGG CAT CCT TCA CCT 4752
Phe Ala Leu Val Gly His Leu Leu Lys Gly Tyr Arg His Pro Ser Pro
1570 1575 1580

GCT ATT GTT GCA AGA ACA GTC AGA ATT TTA CAT ACA CTA CTA ACT CTG 4800
Ala Ile Val Ala Arg Thr Val Arg Ile Leu His Thr Leu Leu Thr Leu
1585 1590 1595 1600

GTT AAC AAA CAC AGA AAT TGT GAC AAA TTT GAA GTG AAT ACA CAG AGC 4848
Val Asn Lys His Arg Asn Cys Asp Lys Phe Glu Val Asn Thr Gln Ser
1605 1610 1615

GTG GCC TAC TTA GCA GCT TTA CTT ACA GTG TCT GAA GAA GTT CGA AGT 4896
Val Ala Tyr Leu Ala Ala Leu Leu Thr Val Ser Glu Glu Val Arg Ser
1620 1625 1630

CGC TGC AGC CTA AAA CAT AGA AAG TCA CTT CTT CTT ACT GAT ATT TCA 4944
Arg Cys Ser Leu Lys His Arg Lys Ser Leu Leu Leu Thr Asp Ile Ser
1635 1640 1645

ATG GAA AAT GTT CCT ATG GAT ACA TAT CCC ATT CAT CAT GGT GAC CCT 4992
Met Glu Asn Val Pro Met Asp Thr Tyr Pro Ile His His Gly Asp Pro
1650 1655 1660

TCC TAT AGG ACA CTA AAG GAG ACT CAG CCA TGG TCC TCT CCC AAA GGT 5040
Ser Tyr Arg Thr Leu Lys Glu Thr Gln Pro Trp Ser Ser Pro Lys Gly
1665 1670 1675 1680

TCT GAA GGA TAC CTT GCA GCC ACC TAT CCA ACT GTC GGC CAG ACC AGT 5088
Ser Glu Gly Tyr Leu Ala Ala Thr Tyr Pro Thr Val Gly Gln Thr Ser
1685 1690 1695

CCC CGA GCC AGG AAA TCC ATG AGC CTG GAC ATG GGG CAA CCT TCT CAG 5136
Pro Arg Ala Arg Lys Ser Met Ser Leu Asp Met Gly Gln Pro Ser Gln
1700 1705 1710

GCC AAC ACT AAG AAG TTG CTT GGA ACA AGG AAA AGT TTT GAT CAC TTG 5184
Ala Asn Thr Lys Lys Leu Leu Gly Thr Arg Lys Ser Phe Asp His Leu
1715 1720 1725

ATA TCA GAC ACA AAG GCT CCT AAA AGG CAA GAA ATG GAA TCA GGG ATC 5232
Ile Ser Asp Thr Lys Ala Pro Lys Arg Gln Glu Met Glu Ser Gly Ile

-continued

```
    1730                    1735                    1740

ACA ACA CCC CCC AAA ATG AGG AGA GTA GCA GAA ACT GAT TAT GAA ATG      5280
Thr Thr Pro Pro Lys Met Arg Arg Val Ala Glu Thr Asp Tyr Glu Met
1745                1750                1755                1760

GAA ACT CAG AGG ATT TCC TCA TCA CAA CAG CAC CCA CAT TTA CGT AAA      5328
Glu Thr Gln Arg Ile Ser Ser Ser Gln Gln His Pro His Leu Arg Lys
                1765                1770                1775

GTT TCA GTG TCT GAA TCA AAT GTT CTC TTG GAT GAA GAA GTA CTT ACT      5376
Val Ser Val Ser Glu Ser Asn Val Leu Leu Asp Glu Glu Val Leu Thr
            1780                1785                1790

GAT CCG AAG ATC CAG GCG CTG CTT CTT ACT GTT CTA GCT ACA CTG GTA      5424
Asp Pro Lys Ile Gln Ala Leu Leu Leu Thr Val Leu Ala Thr Leu Val
        1795                1800                1805

AAA TAT ACC ACA GAT GAG TTT GAT CAA CGA ATT CTT TAT GAA TAC TTA      5472
Lys Tyr Thr Thr Asp Glu Phe Asp Gln Arg Ile Leu Tyr Glu Tyr Leu
    1810                1815                1820

GCA GAG GCC AGT GTT GTG TTT CCC AAA GTC TTT CCT GTT GTG CAT AAT      5520
Ala Glu Ala Ser Val Val Phe Pro Lys Val Phe Pro Val Val His Asn
1825                1830                1835                1840

TTG TTG GAC TCT AAG ATC AAC ACC CTG TTA TCA TTG TGC CAA GAT CCA      5568
Leu Leu Asp Ser Lys Ile Asn Thr Leu Leu Ser Leu Cys Gln Asp Pro
                1845                1850                1855

AAT TTG TTA AAT CCA ATC CAT GGA ATT GTG CAG AGT GTG GTG TAC CAT      5616
Asn Leu Leu Asn Pro Ile His Gly Ile Val Gln Ser Val Val Tyr His
            1860                1865                1870

GAA GAA TCC CCA CCA CAA TAC CAA ACA TCT TAC CTG CAA AGT TTT GGT      5664
Glu Glu Ser Pro Pro Gln Tyr Gln Thr Ser Tyr Leu Gln Ser Phe Gly
        1875                1880                1885

TTT AAT GGC TTG TGG CGG TTT GCA GGA CCG TTT TCA AAG CAA ACA CAA      5712
Phe Asn Gly Leu Trp Arg Phe Ala Gly Pro Phe Ser Lys Gln Thr Gln
    1890                1895                1900

ATT CCA GAC TAT GCT GAG CTT ATT GTT AAG TTT CTT GAT GCC TTG ATT      5760
Ile Pro Asp Tyr Ala Glu Leu Ile Val Lys Phe Leu Asp Ala Leu Ile
1905                1910                1915                1920

GAC ACG TAC CTG CCT GGA ATT GAT GAA GAA ACC AGT GAA GAA TCC CTC      5808
Asp Thr Tyr Leu Pro Gly Ile Asp Glu Glu Thr Ser Glu Glu Ser Leu
                1925                1930                1935

CTG ACT CCC ACA TCT CCT TAC CCT CCT GCA CTG CAG AGC CAG CTT AGT      5856
Leu Thr Pro Thr Ser Pro Tyr Pro Pro Ala Leu Gln Ser Gln Leu Ser
            1940                1945                1950

ATC ACT GCC AAC CTT AAC CTT TCT AAT TCC ATG ACC TCA CTT GCA ACT      5904
Ile Thr Ala Asn Leu Asn Leu Ser Asn Ser Met Thr Ser Leu Ala Thr
        1955                1960                1965

TCC CAG CAT TCC CCA GGA ATC GAC AAG GAG AAC GTT GAA CTC TCC CCT      5952
Ser Gln His Ser Pro Gly Ile Asp Lys Glu Asn Val Glu Leu Ser Pro
    1970                1975                1980

ACC ACT GGC CAC TGT AAC AGT GGA CGA ACT CGC CAC GGA TCC GCA AGC      6000
Thr Thr Gly His Cys Asn Ser Gly Arg Thr Arg His Gly Ser Ala Ser
1985                1990                1995                2000

CAA GTG CAG AAG CAA AGA AGC GCT GGC AGT TTC AAA CGT AAT AGC ATT      6048
Gln Val Gln Lys Gln Arg Ser Ala Gly Ser Phe Lys Arg Asn Ser Ile
                2005                2010                2015

AAG AAG ATC GTG                                                      6060
Lys Lys Ile Val
            2020
```

( 2 ) INFORMATION FOR SEQ ID NO:2:

( i ) SEQUENCE CHARACTERISTICS:

( A ) LENGTH: 2020 amino acids
( B ) TYPE: amino acid
( D ) TOPOLOGY: linear

-continued ( i i ) MOLECULE TYPE: protein ( x i ) SEQUENCE DESCRIPTION: SEQ ID NO:2:

Met Glu Asp Gly Gln Ala Ala Glu Ser Leu His Lys Thr Ile Val Lys
1 5 10 15

Arg Arg Met Ser His Val Ser Gly Gly Gly Ser Ile Asp Leu Ser Asp
20 25 30

Thr Asp Ser Leu Gln Glu Trp Ile Asn Met Thr Gly Phe Leu Cys Ala
35 40 45

Leu Gly Gly Val Cys Leu Gln Gln Arg Ser Asn Ser Gly Leu Ala Thr
50 55 60

Tyr Ser Pro Pro Met Gly Pro Val Ser Glu Arg Lys Gly Ser Met Ile
65 70 75 80

Ser Val Met Ser Ser Glu Gly Asn Ala Asp Thr Pro Val Ser Lys Phe
85 90 95

Met Asp Arg Leu Leu Ser Leu Met Val Cys Asn His Glu Lys Val Gly
100 105 110

Leu Gln Ile Arg Thr Asn Val Lys Asp Leu Val Gly Leu Glu Leu Ser
115 120 125

Pro Ala Leu Tyr Pro Met Leu Phe Asn Lys Leu Lys Asn Thr Ile Ser
130 135 140

Lys Phe Phe Asp Ser Gln Gly Gln Val Leu Leu Thr Asp Thr Asn Thr
145 150 155 160

Gln Phe Val Glu Gln Thr Ile Ala Ile Met Lys Asn Leu Leu Asp Asn
165 170 175

His Thr Glu Gly Ser Ser Glu His Leu Gly Gln Ala Ser Ile Glu Thr
180 185 190

Met Met Leu Asn Leu Val Arg Tyr Val Arg Val Leu Gly Asn Met Val
195 200 205

His Ala Ile Gln Ile Lys Thr Lys Leu Cys Gln Leu Val Glu Val Met
210 215 220

Met Ala Arg Arg Asp Asp Leu Ser Phe Cys Gln Glu Met Lys Phe Arg
225 230 235 240

Asn Lys Met Val Glu Tyr Leu Thr Asp Trp Val Met Gly Thr Ser Asn
245 250 255

Gln Ala Ala Asp Asp Asp Val Lys Cys Leu Thr Arg Asp Leu Asp Gln
260 265 270

Ala Ser Met Glu Ala Val Val Ser Leu Leu Ala Gly Leu Pro Leu Gln
275 280 285

Pro Glu Glu Gly Asp Gly Val Glu Leu Met Glu Ala Lys Ser Gln Leu
290 295 300

Phe Leu Lys Tyr Phe Thr Leu Phe Met Asn Leu Leu Asn Asp Cys Ser
305 310 315 320

Glu Val Glu Asp Glu Ser Ala Gln Thr Gly Gly Arg Lys Arg Gly Met
325 330 335

Ser Arg Arg Leu Ala Ser Leu Arg His Cys Thr Val Leu Ala Met Ser
340 345 350

Asn Leu Leu Asn Ala Asn Val Asp Ser Gly Leu Met His Ser Ile Gly
355 360 365

Leu Gly Tyr His Lys Asp Leu Gln Thr Arg Ala Thr Phe Met Glu Val
370 375 380

Leu Thr Lys Ile Leu Gln Gln Gly Thr Glu Phe Asp Thr Leu Ala Glu
385 390 395 400

Thr Val Leu Ala Asp Arg Phe Glu Arg Leu Val Glu Leu Val Thr Met
405 410 415

-continued

Met Gly Asp Gln Gly Glu Leu Pro Ile Ala Met Ala Leu Ala Asn Val
420 425 430

Val Pro Cys Ser Gln Trp Asp Glu Leu Ala Arg Val Leu Val Thr Leu
435 440 445

Phe Asp Ser Arg His Leu Leu Tyr Gln Leu Leu Trp Asn Met Phe Ser
450 455 460

Lys Glu Val Glu Leu Ala Asp Ser Met Gln Thr Leu Phe Arg Gly Asn
465 470 475 480

Ser Leu Ala Ser Lys Ile Met Thr Phe Cys Phe Lys Val Tyr Gly Ala
485 490 495

Thr Tyr Leu Gln Lys Leu Leu Asp Pro Leu Leu Arg Ile Val Ile Thr
500 505 510

Ser Ser Asp Trp Gln His Val Ser Phe Glu Val Asp Pro Thr Arg Leu
515 520 525

Glu Pro Ser Glu Ser Leu Glu Glu Asn Gln Arg Asn Leu Leu Gln Met
530 535 540

Thr Glu Lys Phe Phe His Ala Ile Ile Ser Ser Ser Ser Glu Phe Pro
545 550 555 560

Pro Gln Leu Arg Ser Val Cys His Cys Leu Tyr Gln Val Val Ser Gln
565 570 575

Arg Phe Pro Gln Asn Ser Ile Gly Ala Val Gly Ser Ala Met Phe Leu
580 585 590

Arg Phe Ile Asn Pro Ala Ile Val Ser Pro Tyr Glu Ala Gly Ile Leu
595 600 605

Asp Lys Lys Pro Pro Pro Arg Ile Glu Arg Gly Leu Lys Leu Met Ser
610 615 620

Lys Ile Leu Gln Ser Ile Ala Asn His Val Leu Phe Thr Lys Glu Glu
625 630 635 640

His Met Arg Pro Phe Asn Asp Phe Val Lys Ser Asn Phe Asp Ala Ala
645 650 655

Arg Arg Phe Phe Leu Asp Ile Ala Ser Asp Cys Pro Thr Ser Asp Ala
660 665 670

Val Asn His Ser Leu Ser Phe Ile Ser Asp Gly Asn Val Leu Ala Leu
675 680 685

His Arg Leu Leu Trp Asn Asn Gln Glu Lys Ile Gly Gln Tyr Leu Ser
690 695 700

Ser Asn Arg Asp His Lys Ala Val Gly Arg Arg Pro Phe Asp Lys Met
705 710 715 720

Ala Thr Leu Leu Ala Tyr Leu Gly Pro Pro Glu His Lys Pro Val Ala
725 730 735

Asp Thr His Trp Ser Ser Leu Asn Leu Thr Ser Ser Lys Phe Glu Glu
740 745 750

Phe Met Thr Arg His Gln Val His Glu Lys Glu Glu Phe Lys Ala Leu
755 760 765

Lys Thr Leu Ser Ile Phe Tyr Gln Ala Gly Thr Ser Lys Ala Gly Asn
770 775 780

Pro Ile Phe Tyr Tyr Val Ala Arg Arg Phe Lys Thr Gly Gln Ile Asn
785 790 795 800

Gly Asp Leu Leu Ile Tyr His Val Leu Leu Thr Leu Lys Pro Tyr Tyr
805 810 815

Ala Lys Pro Tyr Glu Ile Val Val Asp Leu Thr His Thr Gly Pro Ser
820 825 830

Asn Arg Phe Lys Thr Asp Phe Leu Ser Lys Trp Phe Val Val Phe Pro
835 840 845

Gly Phe Ala Tyr Asp Asn Val Ser Ala Val Tyr Ile Tyr Asn Cys Asn

-continued 850 855 860

Ser Trp Val Arg Glu Tyr Thr Lys Tyr His Glu Arg Leu Leu Thr Gly
865 870 875 880

Leu Lys Gly Ser Lys Arg Leu Val Phe Ile Asp Cys Pro Gly Lys Leu
885 890 895

Ala Glu His Ile Glu His Glu Gln Gln Lys Leu Pro Ala Ala Thr Leu
900 905 910

Ala Leu Glu Glu Asp Leu Lys Val Phe His Asn Ala Leu Lys Leu Ala
915 920 925

His Lys Asp Thr Lys Val Ser Ile Lys Val Gly Ser Thr Ala Val Gln
930 935 940

Val Thr Ser Ala Glu Arg Thr Lys Val Leu Gly Gln Ser Val Phe Leu
945 950 955 960

Asn Asp Ile Tyr Tyr Ala Ser Glu Ile Glu Glu Ile Cys Leu Val Asp
965 970 975

Glu Asn Gln Phe Thr Leu Thr Ile Ala Asn Gln Gly Thr Pro Leu Thr
980 985 990

Phe Met His Gln Glu Cys Glu Ala Ile Val Gln Ser Ile Ile His Ile
995 1000 1005

Arg Thr Arg Trp Glu Leu Ser Gln Pro Asp Ser Ile Pro Gln His Thr
1010 1015 1020

Lys Ile Arg Pro Lys Asp Val Pro Gly Thr Leu Leu Asn Ile Ala Leu
1025 1030 1035 1040

Leu Asn Leu Gly Ser Ser Asp Pro Ser Leu Arg Ser Ala Ala Tyr Asn
1045 1050 1055

Leu Leu Cys Ala Leu Thr Cys Thr Phe Asn Leu Lys Ile Glu Gly Gln
1060 1065 1070

Leu Leu Glu Thr Ser Gly Leu Cys Ile Pro Ala Asn Asn Thr Leu Phe
1075 1080 1085

Ile Val Ser Ile Ser Lys Thr Leu Ala Ala Asn Glu Pro His Leu Thr
1090 1095 1100

Leu Glu Phe Leu Glu Glu Cys Ile Ser Gly Phe Ser Lys Ser Ser Ile
1105 1110 1115 1120

Glu Leu Lys His Leu Cys Leu Glu Tyr Met Thr Pro Trp Leu Ser Asn
1125 1130 1135

Leu Val Arg Phe Cys Lys His Asn Asp Asp Ala Lys Arg Gln Arg Val
1140 1145 1150

Thr Ala Ile Leu Asp Lys Leu Ile Thr Met Thr Ile Asn Glu Lys Gln
1155 1160 1165

Met Tyr Pro Ser Ile Gln Ala Lys Ile Trp Gly Ser Leu Gly Gln Ile
1170 1175 1180

Thr Asp Leu Leu Asp Val Val Leu Asp Ser Phe Ile Lys Thr Ser Ala
1185 1190 1195 1200

Thr Gly Gly Leu Gly Ser Ile Lys Ala Glu Val Met Ala Asp Thr Ala
1205 1210 1215

Val Ala Leu Ala Ser Gly Asn Val Lys Leu Val Ser Ser Lys Val Ile
1220 1225 1230

Gly Arg Met Cys Lys Ile Ile Asp Lys Thr Cys Leu Ser Pro Thr Pro
1235 1240 1245

Thr Leu Glu Gln His Leu Met Trp Asp Asp Ile Ala Ile Leu Ala Arg
1250 1255 1260

Tyr Met Leu Met Leu Ser Phe Asn Asn Ser Leu Asp Val Ala Ala His
1265 1270 1275 1280

Leu Pro Tyr Leu Phe His Val Val Thr Phe Leu Val Ala Thr Gly Pro
1285 1290 1295

-continued

Leu Ser Leu Arg Ala Ser Thr His Gly Leu Val Ile Asn Ile Ile His
1300 1305 1310

Ser Leu Cys Thr Cys Ser Gln Leu His Phe Ser Glu Glu Thr Lys Gln
1315 1320 1325

Val Leu Arg Leu Ser Leu Thr Glu Phe Ser Leu Pro Lys Phe Tyr Leu
1330 1335 1340

Leu Phe Gly Ile Ser Lys Val Lys Ser Ala Ala Val Ile Ala Phe Arg
1345 1350 1355 1360

Ser Ser Tyr Arg Asp Arg Ser Phe Ser Pro Gly Ser Tyr Glu Arg Glu
1365 1370 1375

Thr Phe Ala Leu Thr Ser Leu Glu Thr Val Thr Glu Ala Leu Leu Glu
1380 1385 1390

Ile Met Glu Ala Cys Met Arg Asp Ile Pro Thr Cys Lys Trp Leu Asp
1395 1400 1405

Gln Trp Thr Glu Leu Ala Gln Arg Phe Ala Phe Gln Tyr Asn Pro Ser
1410 1415 1420

Leu Gln Pro Arg Ala Leu Val Val Phe Gly Cys Ile Ser Lys Arg Val
1425 1430 1435 1440

Ser His Gly Gln Ile Lys Gln Ile Ile Arg Ile Leu Ser Lys Ala Leu
1445 1450 1455

Glu Ser Cys Leu Lys Gly Pro Asp Thr Tyr Asn Ser Gln Val Leu Ile
1460 1465 1470

Glu Ala Thr Val Ile Ala Leu Thr Lys Leu Gln Pro Leu Leu Asn Lys
1475 1480 1485

Asp Ser Pro Leu His Lys Ala Leu Phe Trp Val Ala Val Ala Val Leu
1490 1495 1500

Gln Leu Asp Glu Val Asn Leu Tyr Ser Ala Gly Thr Ala Leu Leu Glu
1505 1510 1515 1520

Gln Asn Leu His Thr Leu Asp Ser Leu Arg Ile Phe Asn Asp Lys Ser
1525 1530 1535

Pro Glu Glu Val Phe Met Ala Ile Arg Asn Pro Leu Glu Trp His Cys
1540 1545 1550

Lys Gln Met Asp His Phe Val Gly Leu Asn Phe Asn Ser Asn Phe Asn
1555 1560 1565

Phe Ala Leu Val Gly His Leu Leu Lys Gly Tyr Arg His Pro Ser Pro
1570 1575 1580

Ala Ile Val Ala Arg Thr Val Arg Ile Leu His Thr Leu Leu Thr Leu
1585 1590 1595 1600

Val Asn Lys His Arg Asn Cys Asp Lys Phe Glu Val Asn Thr Gln Ser
1605 1610 1615

Val Ala Tyr Leu Ala Ala Leu Leu Thr Val Ser Glu Glu Val Arg Ser
1620 1625 1630

Arg Cys Ser Leu Lys His Arg Lys Ser Leu Leu Leu Thr Asp Ile Ser
1635 1640 1645

Met Glu Asn Val Pro Met Asp Thr Tyr Pro Ile His His Gly Asp Pro
1650 1655 1660

Ser Tyr Arg Thr Leu Lys Glu Thr Gln Pro Trp Ser Ser Pro Lys Gly
1665 1670 1675 1680

Ser Glu Gly Tyr Leu Ala Ala Thr Tyr Pro Thr Val Gly Gln Thr Ser
1685 1690 1695

Pro Arg Ala Arg Lys Ser Met Ser Leu Asp Met Gly Gln Pro Ser Gln
1700 1705 1710

Ala Asn Thr Lys Lys Leu Leu Gly Thr Arg Lys Ser Phe Asp His Leu
1715 1720 1725

-continued

Ile Ser Asp Thr Lys Ala Pro Lys Arg Gln Glu Met Glu Ser Gly Ile
1730 1735 1740

Thr Thr Pro Pro Lys Met Arg Arg Val Ala Glu Thr Asp Tyr Glu Met
1745 1750 1755 1760

Glu Thr Gln Arg Ile Ser Ser Ser Gln Gln His Pro His Leu Arg Lys
1765 1770 1775

Val Ser Val Ser Glu Ser Asn Val Leu Leu Asp Glu Glu Val Leu Thr
1780 1785 1790

Asp Pro Lys Ile Gln Ala Leu Leu Leu Thr Val Leu Ala Thr Leu Val
1795 1800 1805

Lys Tyr Thr Thr Asp Glu Phe Asp Gln Arg Ile Leu Tyr Glu Tyr Leu
1810 1815 1820

Ala Glu Ala Ser Val Val Phe Pro Lys Val Phe Pro Val Val His Asn
1825 1830 1835 1840

Leu Leu Asp Ser Lys Ile Asn Thr Leu Leu Ser Leu Cys Gln Asp Pro
1845 1850 1855

Asn Leu Leu Asn Pro Ile His Gly Ile Val Gln Ser Val Val Tyr His
1860 1865 1870

Glu Glu Ser Pro Pro Gln Tyr Gln Thr Ser Tyr Leu Gln Ser Phe Gly
1875 1880 1885

Phe Asn Gly Leu Trp Arg Phe Ala Gly Pro Phe Ser Lys Gln Thr Gln
1890 1895 1900

Ile Pro Asp Tyr Ala Glu Leu Ile Val Lys Phe Leu Asp Ala Leu Ile
1905 1910 1915 1920

Asp Thr Tyr Leu Pro Gly Ile Asp Glu Glu Thr Ser Glu Glu Ser Leu
1925 1930 1935

Leu Thr Pro Thr Ser Pro Tyr Pro Pro Ala Leu Gln Ser Gln Leu Ser
1940 1945 1950

Ile Thr Ala Asn Leu Asn Leu Ser Asn Ser Met Thr Ser Leu Ala Thr
1955 1960 1965

Ser Gln His Ser Pro Gly Ile Asp Lys Glu Asn Val Glu Leu Ser Pro
1970 1975 1980

Thr Thr Gly His Cys Asn Ser Gly Arg Thr Arg His Gly Ser Ala Ser
1985 1990 1995 2000

Gln Val Gln Lys Gln Arg Ser Ala Gly Ser Phe Lys Arg Asn Ser Ile
2005 2010 2015

Lys Lys Ile Val
2020

1. An isolated DNA consisting essentially of cDNA coding for the NF1 polypeptide.

2. An isolated DNA of claim 1, wherein said NF1 polypeptide comprises the amino acid sequence set forth in SEQ.ID.No:2.

3. An isolated DNA consisting essentially of DNA having at least 15 nucleotides of the cDNA of claim 1.

4. An isolated DNA consisting essentially of DNA having at least 15 nucleotides of the cDNA of claim 1.

5. A replicative cloning vector which comprises the isolated DNA of claim 1 and a replicon operative in a host cell.

6. A replicative cloning vector which comprises the isolated DNA of claim 2 and replicon operative in a host cell.

7. A replicative cloning vector which comprises the isolated DNA of claim 3 and a replicon operative in a host cell.

8. A replicative cloning vector which comprises the isolated DNA of claim 4 and a replicon operative in a host cell.

9. An expression system which comprises the isolated DNA of claim 1 operably linked to suitable control sequences.

10. The expression system of claim 9 disposed in a vector capable of replication in a suitable host.

11. An expression system which comprises the isolated DNA of claim 2 operably linked to suitable control sequences.

12. The expression system of claim 11 disposed in a vector capable of replication in a suitable host.

13. An expression system which comprises the isolated DNA of claim 3 operably linked to suitable control sequences.

14. The expression system of claim 13 disposed in a vector capable of replication in a suitable host.

15. An expression system which comprises the isolated DNA of claim 4 operably linked to suitable control sequences.

16. The expression system of claim 15 disposed in a vector capable of replication in a suitable host.

17. Recombinant host cells transformed with the expression system of claim 9.

18. Recombinant host cells transformed with the expression system of claim 11.

19. Recombinant host cells transformed with the expression system of claim 13.

20. Recombinant host cells transformed with the expression system of claim 15.

21. A method of producing recombinant NF1 polypeptide which comprises culturing the cells of claim 17 under conditions effective for the production of said NF1 polypeptide.

22. A method of producing recombinant NF1 polypeptide which comprises culturing the cells of claim 18 under conditions effective for the production of said NF1 polypeptide.

23. A method of producing recombinant NF1 polypeptide which comprises culturing the cells of claim 19 under conditions effective for the production of said NF1 polypeptide.

24. A method of producing recombinant NF1 polypeptide which comprises culturing the cells of claim 20 under conditions effective for the production of said NF1 polypeptide.

* * * * *

UNITED STATES PATENT AND TRADEMARK OFFICE
CERTIFICATE OF CORRECTION

PATENT NO. : 5,227,292

DATED : July 13, 1993

INVENTOR(S) : Raymond P. WHITE et al.

It is certified that error appears in the above-identified patent and that said Letters Patent is hereby corrected as shown below:

IN THE SPECIFICATION:

At column 57, line 24, following the period, and before "The" insert: --The bacteriophage λ (Stratagene Zap) deposit number 40846 became nonviable and was replaced with a new deposit on 22 July 1994. This new deposit has been given the same deposit number (ATCC 40846). This new deposit consists of inserts identical to those of the original deposit, but with the inserts in p-Bluecript plasmid vectors rather than in the original bacteriophage λ (Stratagene Zap) vectors. The p-Bluescript vectors are in an *E. coli* host. A supplemental deposit has been made for ATCC 40845. This supplemental deposit has been assigned ATCC accession number 69662 and was received by the ATCC on 22 July 1994. This supplemental deposit is identical to the original deposit of ATCC 40845. The ATCC 40845 deposit apparently lost most of the inserts upon storage, necessitating the supplemental deposit. --

In column 57, line 24, following "The" and before "composite" insert --original--.

UNITED STATES PATENT AND TRADEMARK OFFICE
CERTIFICATE OF CORRECTION

PATENT NO. : 5,227,292
DATED : July 13, 1993
INVENTOR(S) : Raymond P. WHITE et al.

It is certified that error appears in the above-indentified patent and that said Letters Patent is hereby corrected as shown below:

In column 57, line 27, following "lambda." and before "The", insert -- The replacement deposit is a composite of cDNA clones comprising a composite of human neurofibromatosis Type 1 gene cDNAs in p-Bluescript. --

Signed and Sealed this

Twenty-seventh Day of December, 1994

Attest:

BRUCE LEHMAN

*Attesting Officer* *Commissioner of Patents and Trademarks*

Adverse Decisions In Interference

Patent No. 5,227,292, Raymond L. White, Peter O'Connell, David H. Viskochil, Richard M. Cawthon, NEUROFIBROMATOSIS TYPE 1 GENE, Interference No. 104,030, final judgment adverse to the patentees rendered February 12, 1999, as to claims 1-24.

*(Official Gazette February 15, 2000)*